(12) United States Patent
Hornsperger et al.

(10) Patent No.: US 10,428,108 B2
(45) Date of Patent: Oct. 1, 2019

(54) DIFLUOROKETAMIDE DERIVATIVES

(71) Applicant: Hoffmann-La Roche Inc., Little Falls, NJ (US)

(72) Inventors: Benoit Hornsperger, Altkirch (FR); Roberto Iacone, Basel (CH); Eric A. Kitas, Aesch (CH); Hans P. Maerki, Basel (CH); Michael Reutlinger, Freiburg (DE); Peter Mohr, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/805,521

(22) Filed: Nov. 7, 2017

(65) Prior Publication Data

US 2018/0057526 A1    Mar. 1, 2018

Related U.S. Application Data

(63) Continuation of application No. PCT/EP2016/060270, filed on May 9, 2016.

(30) Foreign Application Priority Data

May 11, 2015  (EP) .................................... 15167151

(51) Int. Cl.
| | | |
|---|---|---|
| C07D 295/13 | (2006.01) | |
| C07K 5/02 | (2006.01) | |
| C07C 323/60 | (2006.01) | |
| C07C 237/22 | (2006.01) | |
| A61K 38/00 | (2006.01) | |

(52) U.S. Cl.
CPC .......... *C07K 5/0205* (2013.01); *C07C 237/22* (2013.01); *C07C 323/60* (2013.01); *C07D 295/13* (2013.01); *A61K 38/00* (2013.01)

(58) Field of Classification Search
CPC .................................................... C07K 5/0205
See application file for complete search history.

(56) References Cited

PUBLICATIONS

ISR for PCT/EP2016/060270 (dated Jun. 7, 2016).
Linda Truebestein et al., "Substrate-induced remodeling of the active site regulates human HTRA1 activity" Nature Structural & Molecular Biology (XP055124206), 18(3):386-388 (Feb 6, 2011).

*Primary Examiner* — Paul V Ward
(74) *Attorney, Agent, or Firm* — Brian L. Buckwalter

(57) ABSTRACT

The invention provides novel compounds having the general formula (I)

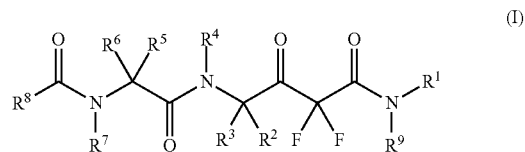

wherein $R^1$, $R^2$, $R^3$, $R^4$, $R^5$, $R^6$, $R^7$, $R^8$ and $R^9$ are as described herein, compositions including the compounds and methods of using the compounds.

24 Claims, No Drawings

DIFLUOROKETAMIDE DERIVATIVES

CROSS REFERENCE TO RELATED APPLICATIONS

This application is a continuation of International Application No. PCT/EP2016/060270 having an international filing date of May 9, 2016 and which claims benefit under 35 U.S.C. § 119 to European Patent Application No. 15167151.8 filed May 11, 2015. The entire contents of both are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

Inhibition of the serine protease HtrA1, which belongs to an evolutionarily conserved family of HtrA proteins, has the potential to protect and treat tissue damage caused by the degeneration of retinal or photoreceptor cells in the human eye. The pathophysiological relevance of HtrA1 in the progression of the age-related macular degeneration has been firmly established by human genetic studies where a SNP in the HtrA1 promoter region results in increased HtrA1 transcript and protein levels. Age-related macular degeneration is the leading cause of severe irreversible central vision loss and blindness in individuals over 65 years of age in developed countries. There are two forms of AMD: dry AMD and wet AMD. Wet AMD (also known as exudative AMD), is associated with pathologic posterior choroidal neovascularization subsequent to the disruption of the delimiting Bruch's membrane. Tissue edema due to the leakage from the abnormal blood vessels damages the macula and impairs vision, eventually leading to blindness. In dry AMD, drusen have been reported in the macula of the eye, the cells in the macula die for the progressive accumulation of the drusen, resulting in progressive vision loss. Dry AMD is clinically described to occur in three stages: 1) early, 2) intermediate, and 3) advanced dry AMD. Dry AMD can also progress into wet AMD during any stage of the disease. Treatment strategies for wet AMD exists and the current standard of care is Lucentis (Genentech/Roche) and Eylea (Regeneron), an anti-VEGF antibody and an anti-VEGF trap injected intravitreally respectively. There are no current treatments for preventing loss of vision for the dry form and for preventing progression of dry AMD to local atrophy of the retinal tissue. As discussed above, HtrA1 risk alleles have been associated, with high statistical significance, with the AMD onsets and the protein has been reported to be present in drusen. These studies and further evidences provide relevance that HtrA1 is a fundamental factor involved in the pathophysiology and progression in AMD. This concept is further confirmed in different AMD disease models, where increased HtrA1 protein levels in the retina tissue have been shown to be responsible for the degradation of extracellular matrix (ECM) proteins like fibronectin, fibulins and aggrecan. The physiological balance between production and disintegration of the ECM components allows for both creation and maintenance of proper retina tissue architecture. Such balance has been reported to be lost in the progression of the age-related macular degeneration. In particular, the fibulins (mainly-3,-5,-6) have been reported to be important components of the Bruch's membrane in maintaining the integrity of elastic lamina and organization of the retina tissue overall. Several variants in fibulin 5 and fibulin 3 were reported to be associated with AMD. Missense mutations of the fibulin 5 gene have been associated with reduced secretion of fibulin 5. Different studies have reported that Htra1 protease activity is directed to the cleavage of the fibulins as substrates. A direct inhibition of HtrA1 protease activity is expected to provide a protection reducing degradation of extracellular matrix proteins, in particular fibulins and fibrionectin, therefore preserving the retina tissue structure. The relevance of HtrA1's role in maintenance of the physiological homeostasis of the ECM components is firmly provided by the identification of human loss-of-function mutations causing familial ischemic cerebral small-vessel disease. The molecular mechanism underlies in the deficient TGFbeta inhibition by HtrA1 resulting in increased signaling levels, which in conjunction with deficient HtrA1-mediated degradation of various extracellular matrix components determine thickening of the intima responsible for the ischemic small-vessels. Given its fundamental role in regulating intracellular signaling pathways (e.g. TGFbeta) and the regulation of ECM proteins turnover, HtrA1 has been involved in several pathologies, as ocular diseases, rheumatoid arthritis, osteoarthritis, Alzheimer's disease, and some types of cancer.

BRIEF SUMMARY OF THE INVENTION

The present invention provides novel compounds of formula (I)

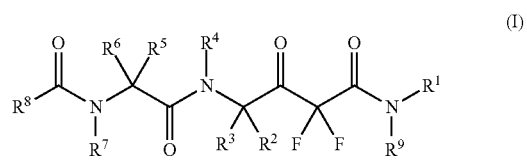

wherein
$R^1$ is alkyl, substituted cycloalkyl, haloalkyl, substituted heterocycloalkylalkyl, substituted aryl alkyl or substituted heteroarylalkyl, wherein substituted cycloalkyl, substituted heterocycloalkylalkyl, substituted arylalkyl and substituted heteroarylalkyl are substituted by $R^{10}$, $R^{11}$ and $R^{12}$;
$R^2$, $R^3$ $R^4$, $R^6$, $R^7$ and $R^9$ are independently selected from H, alkyl and cycloalkyl;
$R^5$ is substituted aryl, substituted aryl alkyl, substituted heteroaryl or substituted heteroaryl alkyl, wherein substituted aryl, substituted arylalkyl, substituted heteroaryl and substituted heteroarylalkyl are substituted by $R^{13}$, $R^{14}$ and $R^{15}$;
$R^8$ is substituted adamantylalkyl, substituted cycloalkyl, substituted cycloalkylalkyl, substituted dicycloalkylalkyl, substituted aryl, substituted arylalkyl, substituted arylalkenyl, substituted diarylalkyl, substituted aryloxyalkyl, substituted diaryloxyalkyl, substituted arylaryloxyalkyl, substituted heteroarylaryloxyalkyl, substituted heteroaryl, substituted heteroarylalkyl, substituted heteroarylalkenyl, substituted arylheteroarylalkyl, substituted arylheteroaryloxyalkyl or substituted aryloxyheteroarylalkyl, wherein substituted adamantylalkyl, substituted cycloalkyl, substituted cycloalkylalkyl, substituted dicycloalkylalkyl, substituted aryl, substituted arylalkyl, substituted arylalkenyl, substituted diarylalkyl, substituted aryloxyalkyl, substituted diaryloxyalkyl, substituted arylaryloxyalkyl, substituted heteroarylaryloxyalkyl, substituted heteroaryl, substituted heteroarylalkyl, substituted heteroarylalkenyl, substituted arylheteroarylalkyl, substituted arylheteroaryloxyalkyl and substituted aryloxyheteroarylalkyl are substituted by $R^{16}$, $R^{17}$ and $R^{18}$; $R^{10}$; $R^{11}$, $R^{12}$; $R^{13}$; $R^{14}$; $R^{15}$; $R^{16}$; $R^{17}$ and $R^{18}$ are independently selected from H, halogen, alkyl, haloalkyl, cycloalkyl, cyano, hydroxyl, alkoxy, haloalkoxy and phenyl;

or pharmaceutically acceptable salts.

The present invention further relates to organic compounds useful for therapy in a mammal, and in particular to serine protease HtrA1 inhibitors for the treatment or prophylaxis of HtrA1-mediated ocular diseases, such as wet or dry age-related macular degeneration, geographic atrophy, diabetic retinopathy, retinopathy of prematurity and polypoidal choroidal vasculopathy.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of HtrA1, particularly in the treatment or prophylaxis of wet or dry age-related macular degeneration, geographic atrophy, diabetic retinopathy, retinopathy of prematurity and polypoidal choroidal vasculopathy.

The term "adamantanylalkyl" denotes an alkyl group wherein one of the hydrogen atoms of the alkyl group has been replaced by an adamantanyl. Particular adamantanylalkyl group is adamantanylmethyl.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl and iso-butenyl. Particular alkenyl group is ethenyl.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular example is methoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, tert-butyl and pentyl. Particular alkyl group is isopropyl.

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "arylalkenyl" denotes an alkenyl group wherein one of the hydrogen atoms of the alkyl group has been replaced by an aryl group. Particular arylalkenyl group is phenylalkenyl. Particular example of arylalkenyl is phenylethylenyl.

The term "arylalkyl" denotes an alkyl group wherein one of the hydrogen atoms of the alkyl group has been replaced by an aryl group. Particular arylalkyl group is phenylalkyl. Particular example of arylalkyl is phenylmethyl.

The term "arylaryloxyalkyl" denotes an alkyl group wherein one of the hydrogen atoms of the alkyl group has been replaced by an aryl group and another one of the hydrogen atoms of the alkyl group has been replaced by an aryloxy group. Particular arylaryloxyalkyl group is phenylphenoxyalkyl. Particular example of arylaryloxyalkyl is phenylphenoxyethyl.

The term "arylheteroarylalkyl" denotes an alkyl group wherein one of the hydrogen atoms of the alkyl group has been replaced by an aryl group and another one of the hydrogen atoms of the alkyl group has been replaced by a heteroaryl group.

The term "aryloxy" denotes a group of the formula —O—R', wherein R' is an aryl group. Particular examples of aryloxy group are groups wherein R' is phenyl.

The term "aryloxyalkyl" denotes an alkyl group wherein one of the hydrogen atoms of the alkyl group has been replaced by an aryloxy group. Particular example of aryloxyalkyl is phenoxyalkyl. Further particular example is phenoxymethyl.

The term "heteroarylaryloxyalkyl" denotes an alkyl group wherein one of the hydrogen atoms of the alkyl group has been replaced by an heteroaryl group and another one of the hydrogen atoms of the alkyl group has been replaced by an aryloxy group. Particular heteroarylaryloxyalkyl group is pyridinylphenoxyalkyl. Particular example of heteroarylaryloxyalkyl is pyridinylphenoxyethyl.

The term "aryloxyheteroarylalkyl" denotes an alkyl group wherein one of the hydrogen atoms of the alkyl group has been replaced by an aryloxy group and another one of the hydrogen atoms of the alkyl group has been replaced by a heteroaryl group. The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cyano" denotes a —C≡N group.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More particular monocyclic cycloalkyl group is cyclohexyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Further particular examples cycloalkylalkyl is cyclohexylethyl.

The term "diarylalkyl" denotes an alkyl group wherein two of the hydrogen atoms of the alkyl group have been replaced by two independently selected aryl groups. Particular diarylalkyl group is diphenylalkyl. Examples of diarylalkyl are diphenylmethyl and diphenylethyl. Particular example of diarylalkyl is phenylethyl. Further particular example is 2,2,-diphenylethyl.

The term "diaryloxyalkyl" denotes an alkyl group wherein two of the hydrogen atoms of the alkyl group have been replaced by two independently selected aryloxy groups. Particular diaryloxyalkyl group is diphenoxyalkyl. Particular example of diaryloxyethyl is 1,2-diphenoxyethyl.

The term "dicycloalkylalkyl" denotes an alkyl group wherein two of the hydrogen atoms of the alkyl group have been replaced by two independently selected cycloalkyl groups.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups is trifluoromethoxy.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "halogen" and "halo" are used interchangeably herein and denote fluoro, chloro, bromo or iodo. Particular halogen is chloro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, and benzothiophenyl.

The term "arylheteroaryloxyalkyl" denotes an alkyl group wherein one of the hydrogen atoms of the alkyl group has been replaced by an aryl group and another one of the hydrogen atoms of the alkyl group has been replaced by an heteroaryloxy group. Particular arylheteroaryloxyalkyl group is phenylpyridinyloxyalkyl. Particular example of arylheteroaryloxyalkyl is phenylpyridinyloxyethyl.

The term "heteroarylalkenyl" denotes an alkenyl group wherein one of the hydrogen atoms of the alkyl group has been replaced by a heteroaryl group.

The term "heteroarylalkyl" denotes an alkyl group wherein one of the hydrogen atoms of the alkyl group has been replaced by a heteroaryl group.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl. Particular example of heterocycloalkyl group is morpholinyl.

The term "heterocycloalkylalkyl" denotes an alkyl group wherein one of the hydrogen atoms of the alkyl group has been replaced by a heterocycloalkyl group. Particular example of heterocycloalkyl group is morpholinylethyl.

The term "phenoxy" denotes a group of the formula —O—R', wherein R' is a phenyl.

The term "phenoxyalkyl" denotes an alkyl group wherein one of the hydrogen atoms of the alkyl group has been replaced by a phenoxy group. Particular example of phenoxyalkyl group is phenoxymethyl.

The term "phenylphenoxyalkyl" denotes an alkyl group wherein one of the hydrogen atoms of the alkyl group has been replaced by a phenoxy group and another of the hydrogen atoms of the alkyl group has been replaced by a phenyl group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

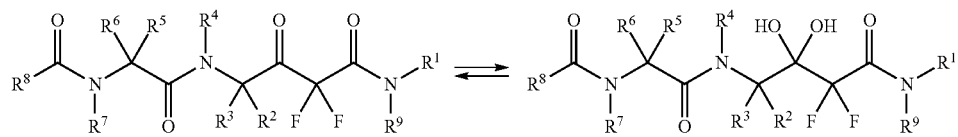

Depending on the individual compound and the conditions it has been exposed to, the $CF_2$-ketone moieties in compounds I exist in part, mainly or totally in form of its hydrate. Thus, any description of a $CF_2$-ketone moiety always describes both ketone and hydrate form.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Also an embodiment of the present invention are compounds according to formula (I) as described herein, wherein $R^1$ is alkyl, substituted cycloalkyl, haloalkyl, substituted heterocycloalkylalkyl, substituted arylalkyl or substituted heteroarylalkyl, wherein substituted cycloalkyl, substituted heterocycloalkylalkyl, substituted arylalkyl and substituted heteroarylalkyl are substituted by $R^{10}$, $R^{11}$ and $R^{12}$;

$R^2$, $R^3$, $R^4$, $R^6$, $R^7$ and $R^9$ are independently selected from H, alkyl and cycloalkyl;

$R^5$ is substituted aryl, substituted arylalkyl, substituted heteroaryl or substituted heteroarylalkyl, wherein substituted aryl, substituted arylalkyl, substituted heteroaryl and substituted heteroarylalkyl are substituted by $R^{13}$, $R^{14}$ and $R^{15}$;

$R^8$ is substituted adamantylalkyl, substituted cycloalkyl, substituted cycloalkylalkyl, substituted dicycloalkylalkyl, substituted aryl, substituted arylalkyl, substituted arylalkenyl, substituted diarylalkyl, substituted aryloxyalkyl, substituted diaryloxyalkyl, substituted arylaryloxyalkyl, substituted heteroaryl, substituted heteroarylalkyl, substituted heteroarylalkenyl, substituted arylheteroarylalkyl or substituted aryloxyheteroarylalkyl, wherein substituted adamantylalkyl, substituted cycloalkyl, substituted cycloalkylalkyl, substituted dicycloalkylalkyl, substituted aryl, substituted arylalkyl, substituted arylalkenyl, substituted diarylalkyl, substituted aryloxyalkyl, substituted diaryloxyalkyl, substituted arylaryloxyalkyl, substituted heteroaryl, substituted heteroarylalkyl, substituted heteroarylalkenyl, substituted arylheteroarylalkyl and substituted aryloxyheteroarylalkyl are substituted by $R^{16}$, $R^{17}$ and $R^{18}$;

$R^{10}$, $R^{11}$, $R^{12}$, $R^{13}$, $R^{14}$, $R^{15}$, $R^{16}$, $R^{17}$ and $R^{18}$ are independently selected from H, halogen, alkyl, haloalkyl, cycloalkyl, cyano, hydroxyl, alkoxy, haloalkoxy and phenyl;

or pharmaceutically acceptable salts.

Another embodiment of the invention is a compound according to formula (I) wherein:

$R^1$ is alkyl, optionally substituted cycloalkyl, haloalkyl, optionally substituted heterocycloalkylalkyl, optionally substituted arylalkyl or optionally substituted heteroarylalkyl, wherein each moiety is optionally substituted by one to three substituents independently selected from halogen, alkyl, haloalkyl, cycloalkyl, cyano, hydroxyl, alkoxy, haloalkoxy or phenyl;

$R^2$, $R^3$, $R^4$, $R^6$, $R^7$ and $R^9$ are independently selected from hydrogen, alkyl or cycloalkyl;

$R^5$ is optionally substituted aryl, optionally substituted arylalkyl, optionally substituted heteroaryl or optionally substituted heteroarylalkyl, wherein each moiety is optionally substituted by one to three substituents independently selected from halogen, alkyl, haloalkyl, cycloalkyl, cyano, hydroxyl, alkoxy, haloalkoxy or phenyl;

$R^8$ is optionally substituted adamantylalkyl, optionally substituted cycloalkyl, optionally substituted cycloalkylalkyl, optionally substituted dicycloalkylalkyl, optionally substituted aryl, optionally substituted arylalkyl, optionally substituted arylalkenyl, optionally substituted diarylalkyl, optionally substituted aryloxyalkyl, optionally substituted diaryloxyalkyl, optionally substituted arylaryloxyalkyl, optionally substituted heteroarylaryloxyalkyl, optionally substituted heteroaryl, optionally substituted heteroarylalkyl, optionally substituted heteroarylalkenyl, optionally substituted arylheteroarylalkyl, optionally substituted arylheteroaryloxyalkyl or optionally substituted aryloxyheteroarylalkyl, wherein each moiety is optionally substituted by one to three substituents independently from selected halogen, alkyl, haloalkyl, cycloalkyl, cyano, hydroxyl, alkoxy, haloalkoxy or phenyl;

or, a pharmaceutically acceptable salt thereof.

Another embodiment of the present invention are compounds according to formula (I) as described herein, wherein $R^1$ is alkyl, haloalkyl, substituted heterocycloalkylalkyl or substituted phenylalkyl, wherein substituted heterocycloalkylalkyl and substituted phenylalkyl are substituted by $R^{10}$, $R^{11}$ and $R^{12}$.

A particular embodiment of the present invention are compounds according to formula (I) as described herein, wherein $R^1$ is haloalkyl.

Also an embodiment of the present invention are compounds according to formula (I) as described herein, wherein $R^{10}$, $R^{11}$, and $R^{12}$ are H.

Another embodiment of the present invention are compounds according to formula (I) as described herein, wherein $R^9$ is H.

A particular embodiment of the present invention are compounds according to formula (I) as described herein, wherein $R^2$ is alkyl.

Another particular embodiment of the present invention are compounds according to formula (I) as described herein, wherein $R^3$ is H.

Also an embodiment of the present invention are compounds according to formula (I) as described herein, wherein $R^4$ is H.

The present invention also relates to compounds according to formula (I) as described herein, wherein $R^5$ is substituted phenyl or substituted phenylalkyl, wherein substituted phenyl and substituted phenylalkyl are substituted by $R^{13}$, $R^{14}$ and $R^{15}$.

A embodiment of the present invention are compounds according to formula (I) as described herein, wherein $R^{13}$, $R^{14}$ and $R^{15}$ are independently selected from H, halogen and alkoxy.

A particular embodiment of the present invention are compounds according to formula (I) as described herein, wherein $R^{13}$, $R^{14}$ and $R^{15}$ are independently selected from H and halogen.

Also an embodiment of the present invention are compounds according to formula (I) as described herein, wherein $R^8$ is substituted phenylalkyl, substituted phenylalkenyl, substituted diphenylalkyl, substituted phenoxyalkyl, substituted pyridinylphenoxyalkyl, substituted phenylpyridinyloxyalkyl or substituted phenylphenoxyalkyl, wherein substituted phenylalkyl, substituted phenylalkenyl, substituted diphenylalkyl, substituted phenoxyalkyl and substituted phenylphenoxyalkyl are substituted by $R^{16}$, $R^{17}$ and $R^{18}$.

Also an embodiment of the present invention are compounds according to formula (I) as described herein, wherein $R^8$ is substituted phenylalkyl, substituted phenylalkenyl, substituted diphenylalkyl, substituted phenoxyalkyl or substituted phenylphenoxyalkyl, wherein substituted phenylalkyl, substituted phenylalkenyl, substituted diphenylalkyl, substituted phenoxyalkyl and substituted phenylphenoxyalkyl are substituted by $R^{16}$, $R^{17}$ and $R^{18}$.

A particular embodiment of the present invention are compounds according to formula (I) as described herein, wherein $R^8$ is substituted phenoxyalkyl or substituted phenylphenoxyalkyl, wherein substituted phenoxyalkyl and substituted phenylphenoxyalkyl are substituted by $R^{18}$, $R^{17}$ and $R^{18}$.

Another embodiment of the present invention are compounds according to formula (I) as described herein, wherein $R^{16}$, $R^{17}$ and $R^{18}$ are independently selected from H and halogen.

A more particular embodiment of the present invention are compounds according to formula (I) as described herein, wherein the compound is of formula (Ia).

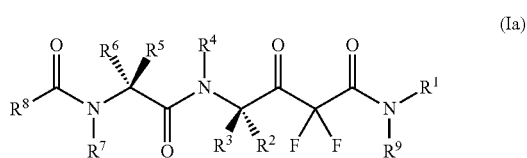

(Ia)

A furthermore embodiment of the present invention are compounds according to formula (I) as described herein, wherein $R^1$ is haloalkyl;
$R^2$ is alkyl;
$R^3$ $R^4$, $R^6$, $R^7$ and $R^9$ are H;
$R^5$ is substituted phenyl or substituted phenylalkyl, wherein substituted phenyl and substituted phenylalkyl are substituted by $R^{13}$, $R^{14}$ and $R^{15}$;
$R^8$ is substituted phenoxyalkyl or substituted phenylphenoxyalkyl, wherein substituted phenoxyalkyl and substituted phenylphenoxyalkyl are substituted by $R^{16}$, $R^{17}$ and $R^{18}$;
$R^{13}$, $R^{14}$, $R^{15}$, $R^{16}$, $R^{17}$ and $R^{18}$ are independently selected from H and halogen;

or pharmaceutically acceptable salts.

Particular examples of compounds of formula (I) as described herein are selected from (4S)-4-[[(2S)-2-[3-(3-chlorophenyl)propanoylamino]-3-phenylpropanoyl]amino]-2,2-difluoro-5-methyl-N-(2-morpholin-4-ylethyl)-3-oxohexanamide;

(S)-4-((S)-2-((E)-3-(3,5-dichlorophenyl)acrylamido)-2-phenylacetamido)-2,2-difluoro-5-methyl-3-oxo-N-(2,2,2-trifluoroethyl)hexanamide;

(S)-4-((S)-2-(3-(3-chlorophenyl)propanamido)-3-phenylpropanamido)-2,2-difluoro-5-methyl-3-oxo-N-phenethylhexanamide;

(S)-4-((S)-2-(3-(3-chlorophenyl)propanamido)-3-phenylpropanamido)-2,2-difluoro-5-methyl-3-oxo-N-(3,3,3-trifluoropropyl)hexanamide;

(S)-4-((S)-2-(3-(3,4-dichlorophenyl)propanamido)-3-phenylpropanamido)-2,2-difluoro-5-methyl-3-oxo-N-(2,2,2-trifluoroethyl)hexanamide;

(S)-4-((S)-2-(2-(3-chlorophenoxy)acetamido)-3-phenylpropanamido)-2,2-difluoro-5-methyl-3-oxo-N-(2,2,2-trifluoroethyl)hexanamide;

(S)-4-((S)-2-(2-(3,4-dichlorophenoxy)acetamido)-3-phenylpropanamido)-2,2-difluoro-5-methyl-3-oxo-N-(2,2,2-trifluoroethyl)hexanamide;

(S)-4-((S)-2-(3-(3,5-dichlorophenyl)propanamido)-3-phenylpropanamido)-2,2-difluoro-5-methyl-3-oxo-N-(2,2,2-trifluoroethyl)hexanamide;

(S)-4-((S)-2-(2-(3,5-dichlorophenoxy)acetamido)-3-phenylpropanamido)-2,2-difluoro-5-methyl-3-oxo-N-(2,2,2-trifluoroethyl)hexanamide;

(S)-4-((S)-2-(3-(3-chlorophenyl)propanamido)-3-phenylpropanamido)-2,2-difluoro-5-methyl-3-oxo-N-(2,2,2-trifluoroethyl)hexanamide;
(S)-4-((S)-2-(2-(3,4-dichlorophenoxy)acetamido)-3-phenylpropanamido)-2,2-difluoro-5-methyl-N-(2-morpholinoethyl)-3-oxohexanamide;
(S)-4-((S)-2-(2-(3-chlorophenoxy)acetamido)-3-phenylpropanamido)-2,2-difluoro-5-methyl-N-(2-morpholinoethyl)-3-oxohexanamide;
(S)-4-((S)-2-(2-(3,5-dichlorophenoxy)acetamido)-3-phenylpropanamido)-2,2-difluoro-5-methyl-N-(2-morpholinoethyl)-3-oxohexanamide;
(S)-4-((S)-2-(3-(3,5-dichlorophenyl)propanamido)-3-phenylpropanamido)-2,2-difluoro-5-methyl-N-(2-morpholinoethyl)-3-oxohexanamide;
(S)-4-((S)-2-(3-(3,4-dichlorophenyl)propanamido)-3-phenylpropanamido)-2,2-difluoro-5-methyl-N-(2-morpholinoethyl)-3-oxohexanamide;
(S)-4-((S)-2-(3-(3,4-dichlorophenyl)propanamido)-3-phenylpropanamido)-2,2-difluoro-5-methyl-3-oxo-N-phenethylhexanamide;
(S)-4-((S)-2-(2-(3-chlorophenoxy)acetamido)-3-phenylpropanamido)-2,2-difluoro-5-methyl-3-oxo-N-phenethylhexanamide;
(S)-4-((S)-2-(3-(3,4-dichlorophenyl)propanamido)-3-phenylpropanamido)-2,2-difluoro-5-methyl-3-oxo-N-(3,3,3-trifluoropropyl)hexanamide;
(S)-4-((S)-2-(2-(3,5-dichlorophenoxy)acetamido)-3-phenylpropanamido)-2,2-difluoro-5-methyl-3-oxo-N-(3,3,3-trifluoropropyl)hexanamide;
(S)-4-((S)-2-(2-(3-chlorophenoxy)acetamido)-3-phenylpropanamido)-2,2-difluoro-5-methyl-3-oxo-N-(3,3,3-trifluoropropyl)hexanamide;
(S)-4-((S)-2-(3-(3,5-dichlorophenyl)propanamido)-3-phenylpropanamido)-2,2-difluoro-5-methyl-3-oxo-N-(3,3,3-trifluoropropyl)hexanamide;
(S)-4-((S)-2-(2-(3,4-dichlorophenoxy)acetamido)-3-phenylpropanamido)-2,2-difluoro-5-methyl-3-oxo-N-(3,3,3-trifluoropropyl)hexanamide;
(S)-4-((S)-3-(4-chlorophenyl)-2-(3-(3,4-dichlorophenyl)propanamido)propanamido)-2,2-difluoro-5-methyl-3-oxo-N-phenethylhexanamide;
(S)-4-((S)-2-(3-(3,4-dichlorophenyl)propanamido)-3-(3,4-dimethoxyphenyl)propanamido)-2,2-difluoro-5-methyl-3-oxo-N-phenethylhexanamide;
(S)-4-((S)-2-(3-(3,4-dichlorophenyl)propanamido)-3-(3,4-dimethoxyphenyl)propanamido)-2,2-difluoro-5-methyl-3-oxo-N-(2,2,2-trifluoroethyl)hexanamide;
(S)-4-((S)-3-(3,4-dichlorophenyl)-2-(3-(3,4-dichlorophenyl)propanamido)propanamido)-2,2-difluoro-5-methyl-3-oxo-N-phenethylhexanamide;
(S)-4-((S)-3-(4-chlorophenyl)-2-(2-(3,5-dichlorophenoxy)acetamido)propanamido)-2,2-difluoro-5-methyl-3-oxo-N-(2,2,2-trifluoroethyl)hexanamide;
(S)-4-((S)-2-(2-(3,5-dichlorophenoxy)acetamido)-3-(3,4-dichlorophenyl)propanamido)-2,2-difluoro-5-methyl-3-oxo-N-(2,2,2-trifluoroethyl)hexanamide;
(S)-4-((S)-2-(2-(3,5-dichlorophenoxy)acetamido)-3-phenylpropanamido)-N-ethyl-2,2-difluoro-5-methyl-3-oxohexanamide;
(S)-4-((S)-2-(2-(3,5-dichlorophenoxy)acetamido)-3-phenylpropanamido)-2,2-difluoro-N-isobutyl-5-methyl-3-oxohexanamide;
(S)-4-((S)-2-(2-(3,5-dichlorophenoxy)acetamido)-3-(3,4-dichlorophenyl)propanamido)-N-ethyl-2,2-difluoro-5-methyl-3-oxohexanamide;
(S)-4-((S)-2-(2-(3,5-dichlorophenoxy)acetamido)-3-(3,4-dichlorophenyl)propanamido)-2,2-difluoro-N-isobutyl-5-methyl-3-oxohexanamide;
(S)-4-((S)-2-(2-(3,5-dichlorophenoxy)acetamido)-3-(3,4-difluorophenyl)propanamido)-2,2-difluoro-N-isobutyl-5-methyl-3-oxohexanamide;
(S)-4-((S)-3-(4-chlorophenyl)-2-(2-(3,5-dichlorophenoxy)acetamido)propanamido)-2,2-difluoro-5-methyl-3-oxo-N-(3,3,3-trifluoropropyl)hexanamide;
(S)-4-((S)-2-(2-(3,5-dichlorophenoxy)acetamido)-3-(3,4-dichlorophenyl)propanamido)-2,2-difluoro-5-methyl-3-oxo-N-(3,3,3-trifluoropropyl)hexanamide;
(S)-4-((S)-2-(2-(3,5-dichlorophenoxy)acetamido)-3-(3,4-difluorophenyl)propanamido)-2,2-difluoro-5-methyl-3-oxo-N-(3,3,3-trifluoropropyl)hexanamide;
(S)-4-((S)-2-(2-(3,5-dichlorophenoxy)acetamido)-3-(3,4-dimethoxyphenyl)propanamido)-2,2-difluoro-5-methyl-3-oxo-N-(3,3,3-trifluoropropyl)hexanamide;
(S)-4-((S)-2-(2-(3,5-dichlorophenoxy)acetamido)-3-phenylpropanamido)-2,2-difluoro-5-methyl-3-oxo-N-propylhexanamide;
(S)-4-((S)-2-(2-(3,5-dichlorophenoxy)acetamido)-3-phenylpropanamido)-2,2-difluoro-5-methyl-N-neopentyl-3-oxohexanamide;
(4S)-4-((2S)-2-(3-(3,4-dichlorophenyl)-3-phenylpropanamido)-3-phenylpropanamido)-2,2-difluoro-5-methyl-3-oxo-N-(2,2,2-trifluoroethyl)hexanamide;
(S)-4-((S)-3-(4-chlorophenyl)-2-(2-(3,5-dichlorophenoxy)acetamido)propanamido)-2,2-difluoro-5-methyl-3-oxo-N-propylhexanamide;
(S)-4-((S)-2-(2-(3,5-dichlorophenoxy)acetamido)-3-(3,4-difluorophenyl)propanamido)-2,2-difluoro-5-methyl-N-neopentyl-3-oxohexanamide;
(S)-4-((S)-2-(2-(3,5-dichlorophenoxy)acetamido)-3-(3,4-difluorophenyl)propanamido)-2,2-difluoro-5-methyl-3-oxo-N-(2,2,2-trifluoroethyl)hexanamide;
(S)-4-((S)-2-(2-(3,5-dichlorophenoxy)acetamido)-3-(3,4-dimethoxyphenyl)propanamido)-2,2-difluoro-5-methyl-3-oxo-N-(2,2,2-trifluoroethyl)hexanamide;
(4S)-4-((2S)-2-(3-(3,4-dichlorophenyl)-3-(4-methoxyphenyl)propanamido)-3-phenylpropanamido)-2,2-difluoro-5-methyl-3-oxo-N-(2,2,2-trifluoroethyl)hexanamide;
(S)-4-((S)-2-((E)-3-(3,4-dichlorophenyl)acrylamido)-3-phenylpropanamido)-2,2-difluoro-5-methyl-3-oxo-N-propylhexanamide;
(S)-4-((S)-2-((E)-3-(3,4-dichlorophenyl)acrylamido)-3-phenylpropanamido)-2,2-difluoro-5-methyl-N-neopentyl-3-oxohexanamide;
(S)-4-((S)-2-((E)-3-(3,4-dichlorophenyl)acrylamido)-3-phenylpropanamido)-2,2-difluoro-5-methyl-3-oxo-N-(2,2,2-trifluoroethyl)hexanamide;
(S)-4-((S)-2-((E)-3-(3,5-dichlorophenyl)acrylamido)-3-phenylpropanamido)-2,2-difluoro-5-methyl-3-oxo-N-(2,2,2-trifluoroethyl)hexanamide;
(S)-4-((S)-2-(4-chlorophenyl)-2-(2-(3,5-dichlorophenoxy)acetamido)acetamido)-2,2-difluoro-5-methyl-3-oxo-N-(2,2,2-trifluoroethyl)hexanamide;
(S)-4-((S)-2-(3,3-diphenylpropanamido)-3-phenylpropanamido)-2,2-difluoro-5-methyl-3-oxo-N-(2,2,2-trifluoroethyl)hexanamide;
(4S)-4-((2S)-2-(3-(3,5-dichlorophenyl)-3-(4-methoxyphenyl)propanamido)-3-phenylpropanamido)-2,2-difluoro-5-methyl-3-oxo-N-(2,2,2-trifluoroethyl)hexanamide;
(4S)-4-((2S)-3-(4-chlorophenyl)-2-(3-(3,4-dichlorophenyl)-3-phenylpropanamido)propanamido)-2,2-difluoro-5-methyl-3-oxo-N-(2,2,2-trifluoroethyl)hexanamide;

(4S)-4-((2S)-2-(3-(3,4-dichlorophenyl)-3-phenylpropanamido)-3-(4-methoxyphenyl)propanamido)-2,2-difluoro-5-methyl-3-oxo-N-(2,2,2-trifluoroethyl)hexanamide;

(4#S!)-4-[[(2#S!)-2-[[2-(3,5-dichlorophenoxy)acetyl]amino]-2-phenyl acetyl]amino]-2,2-difluoro-5-methyl-3-oxo-#N!-(2,2,2-trifluoroethyl)hexanamide;

(S)-4-((S)-2-(2-(3,5-dichlorophenoxy)acetamido)-2-(4-fluorophenyl)acetamido)-2,2-difluoro-5-methyl-3-oxo-N-(2,2,2-trifluoroethyl)hexanamide;

(4S)-4-((2S)-2-(3-(3,4-dichlorophenyl)-3-phenylpropanamido)-2-phenylacetamido)-2,2-difluoro-5-methyl-3-oxo-N-(2,2,2-trifluoroethyl)hexanamide;

(4S)-4-((2S)-2-(4-chlorophenyl)-2-(3-(3,4-dichlorophenyl)-3-phenylpropanamido)acetamido)-2,2-difluoro-5-methyl-3-oxo-N-(2,2,2-trifluoroethyl)hexanamide;

(S)-4-((S)-2-(3-(3,4-dichlorophenyl)propanamido)-2-phenylacetamido)-2,2-difluoro-5-methyl-3-oxo-N-(2,2,2-trifluoroethyl)hexanamide;

(4S)-4-((2S)-2-(3-(4-bromophenyl)-3-phenylpropanamido)-3-phenylpropanamido)-2,2-difluoro-5-methyl-3-oxo-N-(2,2,2-trifluoroethyl)hexanamide;

(4S)-4-((2S)-2-(3-(4-bromophenyl)-3-phenylpropanamido)-3-(4-chlorophenyl)propanamido)-2,2-difluoro-5-methyl-3-oxo-N-(2,2,2-trifluoroethyl)hexanamide;

(S)-4-((S)-2-((E)-3-(3,4-dichlorophenyl)acrylamido)-2-phenylacetamido)-2,2-difluoro-5-methyl-3-oxo-N-(2,2,2-trifluoroethyl)hexanamide;

(S)-4-((S)-2-((E)-3-(3-chlorophenyl)acrylamido)-2-phenylacetamido)-2,2-difluoro-5-methyl-3-oxo-N-(2,2,2-trifluoroethyl)hexanamide;

(S)-4-((S)-2-((E)-3-(4-chlorophenyl)acrylamido)-2-phenylacetamido)-2,2-difluoro-5-methyl-3-oxo-N-(2,2,2-trifluoroethyl)hexanamide;

(4S)-4-((2S)-2-(3-(3,5-dichlorophenyl)-3-phenylpropanamido)-2-phenylacetamido)-2,2-difluoro-5-methyl-3-oxo-N-(2,2,2-trifluoroethyl)hexanamide;

(S)-4-((S)-2-(4-chlorophenyl)-2-((E)-3-(3,4-dichlorophenyl)acrylamido)acetamido)-2,2-difluoro-5-methyl-3-oxo-N-(2,2,2-trifluoroethyl)hexanamide;

(S)-4-((S)-2-(4-chlorophenyl)-2-((E)-3-(3,5-dichlorophenyl)acrylamido)acetamido)-2,2-difluoro-5-methyl-3-oxo-N-(2,2,2-trifluoroethyl)hexanamide;

(S)-4-((S)-2-(4-chlorophenyl)-2-((E)-3-(3-chlorophenyl)acrylamido)acetamido)-2,2-difluoro-5-methyl-3-oxo-N-(2,2,2-trifluoroethyl)hexanamide;

(S)-4-((S)-2-(4-chlorophenyl)-2-((E)-3-(4-chlorophenyl)acrylamido)acetamido)-2,2-difluoro-5-methyl-3-oxo-N-(2,2,2-trifluoroethyl)hexanamide;

(4S)-4-((2S)-2-(3-(3,4-dichlorophenyl)-3-phenoxypropanamido)-2-phenylacetamido)-2,2-difluoro-5-methyl-3-oxo-N-(2,2,2-trifluoroethyl)hexanamide;

(4S)-4-((2S)-2-(3-(3,4-dichlorophenyl)-3-phenoxypropanamido)-3-phenylpropanamido)-2,2-difluoro-5-methyl-3-oxo-N-(2,2,2-trifluoroethyl)hexanamide;

(4S)-4-((2S)-2-(3-(4-chlorophenoxy)-3-(3,4-dichlorophenyl)propanamido)-2-phenylacetamido)-2,2-difluoro-5-methyl-3-oxo-N-(2,2,2-trifluoroethyl)hexanamide;

(4S)-4-((2S)-2-(3-(4-chlorophenoxy)-3-(3,4-dichlorophenyl)propanamido)-3-phenylpropanamido)-2,2-difluoro-5-methyl-3-oxo-N-(2,2,2-trifluoroethyl)hexanamide;

(S)-4-((S)-2-((S)-3-(3,5-dichlorophenyl)-3-phenylpropanamido)-2-phenylacetamido)-2,2-difluoro-5-methyl-3-oxo-N-(2,2,2-trifluoroethyl)hexanamide;

(4S)-4-((2S)-2-(3-(3,5-difluorophenyl)-3-(4-methoxyphenyl)propanamido)-2-phenylacetamido)-2,2-difluoro-5-methyl-3-oxo-N-(2,2,2-trifluoroethyl)hexanamide;

(4S)-4-((2S)-2-(3-(3,5-difluorophenyl)-3-(4-methoxyphenyl)propanamido)-3-phenylpropanamido)-2,2-difluoro-5-methyl-3-oxo-N-(2,2,2-trifluoroethyl)hexanamide;

(S)-4-((S)-2-(4-chlorophenyl)-2-((S)-3-(3,5-dichlorophenyl)-3-phenylpropanamido)acetamido)-2,2-difluoro-5-methyl-3-oxo-N-(2,2,2-trifluoroethyl)hexanamide;

(S)-4-((S)-2-((R)-3-(3,5-dichlorophenyl)-3-phenylpropanamido)-2-phenylacetamido)-2,2-difluoro-5-methyl-3-oxo-N-(2,2,2-trifluoroethyl)hexanamide;

(S)-4-((S)-2-(4-chlorophenyl)-2-((R)-3-(3,5-dichlorophenyl)-3-phenylpropanamido)acetamido)-2,2-difluoro-5-methyl-3-oxo-N-(2,2,2-trifluoroethyl)hexanamide;

and pharmaceutically acceptable salts thereof.

Also particular examples of compounds of formula (I) as described herein are selected from (4S)-4-[[(2S)-2-[[(3S)-3-(3-chlorophenoxy)-3-phenylpropanoyl]amino]-2-(4-chlorophenyl)acetyl]amino]-2,2-difluoro-5-methyl-3-oxo-N-(2,2,2-trifluoroethyl)hexanamide;

(4S)-4-[[(2S)-2-[[(3S)-3-(3-chlorophenoxy)-3-phenylpropanoyl]amino]-2-phenylacetyl]amino]-2,2-difluoro-5-methyl-3-oxo-N-(2,2,2-trifluoroethyl)hexanamide;

(4S)-4-[[(2S)-2-[3-(3,4-dichlorophenyl)propanoylamino]-3-(4-methoxyphenyl)propanoyl]amino]-2,2-difluoro-5-methyl-3-oxo-N-(2,2,2-trifluoroethyl)hexanamide;

(4S)-4-[[(2S)-2-[[2-(3,5-dichlorophenoxy)acetyl]amino]-2-(4-methoxyphenyl)acetyl]amino]-2,2-difluoro-5-methyl-3-oxo-N-(2,2,2-trifluoroethyl)hexanamide;

(4S)-4-[[(2S)-2-[[3-(3-chlorophenyl)-3-phenylpropanoyl]amino]-2-phenylacetyl]amino]-2,2-difluoro-5-methyl-3-oxo-N-(2,2,2-trifluoroethyl)hexanamide;

(4S)-4-[[(2S)-2-(4-chlorophenyl)-2-[[3-(3-chlorophenyl)-3-phenylpropanoyl]amino]acetyl]amino]-2,2-difluoro-5-methyl-3-oxo-N-(2,2,2-trifluoroethyl)hexanamide;

(4S)-4-[[(2S)-2-[[(E)-3-(4-chlorophenyl)prop-2-enoyl]amino]-2-(4-methoxyphenyl)acetyl]amino]-2,2-difluoro-5-methyl-3-oxo-N-(2,2,2-trifluoroethyl)hexanamide;

(4S)-4-[[(2S)-2-[[3-(3,4-dichlorophenyl)-3-phenylpropanoyl]amino]-2-(4-methoxyphenyl)acetyl]amino]-2,2-difluoro-5-methyl-3-oxo-N-(2,2,2-trifluoroethyl)hexanamide;

(4S)-4-[[(2S)-2-[[3-(3-chlorophenoxy)-3-(3,4-dichlorophenyl)propanoyl]amino]-2-phenylacetyl]amino]-2,2-difluoro-5-methyl-3-oxo-N-(2,2,2-trifluoroethyl)hexanamide;

(4S)-4-[[(2S)-2-[[3-(3-chlorophenoxy)-3-(3,4-dichlorophenyl)propanoyl]amino]-2-(4-chlorophenyl)acetyl]amino]-2,2-difluoro-5-methyl-3-oxo-N-(2,2,2-trifluoroethyl)hexanamide;

(4S)-4-[[(2S)-2-[[(3R)-3-(3-chlorophenoxy)-3-phenylpropanoyl]amino]-2-phenylacetyl]amino]-2,2-difluoro-5-methyl-3-oxo-N-(2,2,2-trifluoroethyl)hexanamide;

(4S)-4-[[(2S)-2-[[(3R)-3-(3-chlorophenoxy)-3-phenylpropanoyl]amino]-2-(4-chlorophenyl)acetyl]amino]-2,2-difluoro-5-methyl-3-oxo-N-(2,2,2-trifluoroethyl)hexanamide;

(4S)-4-[[(2S)-2-[[(3S)-3-(4-chlorophenoxy)-3-(3,4-dichlorophenyl)propanoyl]amino]-2-(4-chlorophenyl)acetyl]amino]-2,2-difluoro-5-methyl-3-oxo-N-(2,2,2-trifluoroethyl)hexanamide;

(4S)-4-[[(2S)-2-[[3-(4-chlorophenoxy)-3-(3,4-dichlorophenyl)propanoyl]amino]-2-phenylacetyl]amino]-2,2-difluoro-5-methyl-N-(2-morpholin-4-ylethyl)-3-oxohexanamide;

(4S)-4-[[(2S)-2-[[(E)-3-(3,4-dichlorophenyl)prop-2-enoyl]amino]-2-phenyl acetyl]amino]-2,2-difluoro-5-methyl-N-(2-morpholin-4-ylethyl)-3-oxohexanamide;

(4S)-4-[[(2S)-2-[[2-(3,5-dichlorophenyl)sulfanylacetyl]amino]-3-phenylpropanoyl]amino]-2,2-difluoro-5-methyl-3-oxo-N-(2,2,2-trifluoroethyl)hexanamide;

(4S)-4-[[(2S)-2-[[3-(3-chlorophenoxy)-3-(5-chloropyridin-3-yl)propanoyl]amino]-2-phenylacetyl]amino]-2,2-difluoro-5-methyl-3-oxo-N-(2,2,2-trifluoroethyl)hexanamide;

(4S)-4-[[(2S)-2-[[3-(3-chlorophenyl)-3-pyridin-3-yloxypropanoyl]amino]-2-phenylacetyl]amino]-2,2-difluoro-5-methyl-3-oxo-N-(2,2,2-trifluoroethyl)hexanamide;

(4S)-4-[[(2S)-2-[[3-(3-chlorophenyl)-3-(5-chloropyridin-3-yl)oxypropanoyl]amino]-2-(4-methoxyphenyl)acetyl]amino]-2,2-difluoro-5-methyl-3-oxo-N-(2,2,2-trifluoroethyl)hexanamide;

and pharmaceutically acceptable salts thereof.

Further particular examples of compounds of formula (I) as described herein are selected from (4S)-4-[[(2S)-2-[[2-(3,5-dichlorophenoxy)acetyl]amino]-3-phenylpropanoyl]amino]-2,2-difluoro-5-methyl-3-oxo-N-(2,2,2-trifluoroethyl)hexanamide;

(4S)-4-[[(2S)-3-(4-chlorophenyl)-2-[[2-(3,5-dichlorophenoxy)acetyl]amino]propanoyl]amino]-2,2-difluoro-5-methyl-3-oxo-N-(2,2,2-trifluoroethyl)hexanamide;

(4S)-4-[[(2S)-2-(4-chlorophenyl)-2-[[2-(3,5-dichlorophenoxy)acetyl]amino]acetyl]amino]-2,2-difluoro-5-methyl-3-oxo-N-(2,2,2-trifluoroethyl)hexanamide;

(4S)-4-[[(2S)-2-[[2-(3,5-dichlorophenoxy)acetyl]amino]-2-phenylacetyl]amino]-2,2-difluoro-5-methyl-3-oxo-N-(2,2,2-trifluoroethyl)hexanamide;

(4S)-4-[[(2S)-2-[[3-(3,4-dichlorophenyl)-3-phenoxypropanoyl]amino]-3-phenylpropanoyl]amino]-2,2-difluoro-5-methyl-3-oxo-N-(2,2,2-trifluoroethyl)hexanamide;

(4S)-4-[[(2S)-2-[[3-(4-chlorophenoxy)-3-(3,4-dichlorophenyl)propanoyl]amino]-3-phenylpropanoyl]amino]-2,2-difluoro-5-methyl-3-oxo-N-(2,2,2-trifluoroethyl)hexanamide;

(4S)-4-[[(2S)-2-[[3-(4-chlorophenoxy)-3-(3,4-dichlorophenyl)propanoyl]amino]-2-phenylacetyl]amino]-2,2-difluoro-5-methyl-3-oxo-N-(2,2,2-trifluoroethyl)hexanamide;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

The following abbreviations are used in the present text: BOC=t-butyloxycarbonyl, BuLi=butyllithium, CDI=1,1-carbonyldiimidazole, DBU=2,3,4,6,7,8,9,10-octahydro-pyrimido[1,2-a]azepine, DCE=1,2-dichloroethane, DCM=dichloromethane, DIAD=diisopropyl-azodicarboxylate, DIBALH=di-i-butylaluminum hydride, DCC=N,N'-dicyclohexyl-carbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, eq.=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=iPr$_2$NEt=N-ethyl diisopropylamine, LAH=lithium aluminum hydride, LDA=lithium diisopropylamide, NHS=N-hydroxy-succinimide, PG=protecting group, Red-Al=sodium bis(2-methoxyethoxy) aluminium hydride, RT=room temperature, TBME=t-butyl methyl ether, TBTU=O-benzotriazol-1-yl-N,N,N',N'-tetramethyl-uronium tetrafluoroborate, TEA=Et$_3$N= triethylamine, TFA=trifluoroacetic acid, THF=tetrahy- drofuran, quant.=quantitative.

The synthesis of compounds of the general formula I can be accomplished according to Scheme 1. Appropriately protected (e.g., with a BOC-group) α-amino-aldehyde 1 is reacted with the Reformatsky reagent derived from ethyl 2-bromo-2,2-difluoroacetate 2 to provide, under chelation control, amino-hydroxy-ester 3 (scheme 1, step a). The latter is transformed into amide 5 by treatment with the necessary amine 4 at elevated temperature, typically in boiling methanol (scheme 1, step b). Conventional deprotection, in the case of a BOC group with, e.g. TFA or anhydrous HCl in dioxane, delivers free amine 6 (scheme 1, step c), which can then be coupled with the building block 7 (for its synthesis, see below) under standard peptide coupling conditions, e.g., with HATU or TBTU, and an appropriate base, e.g., Huenig's base or TEA, in an inert solvent like DMF, to furnish intermediate 8 (scheme 1, step d). Alternatively, amine 6 is coupled with NHS-ester 7' under Schotten Baumann-conditions in a mixture of, e.g., THF, DME, and water, in the presence of a mild base like NaHCO3, to generate the very same intermediate 8 (scheme 1, step d). Eventually, oxidation, e.g., with Dess Martin periodinane, in an inert solvent like DCM generates the final target molecule I. Starting aldehyde 1 which is prone to racemization—in case one of R$^2$ or R$^3$ is hydrogen—is prepared as described in literature from the corresponding Weinreb amide by reduction with LAH and used immediately for the next step (J. Med. Chem. 1992,35, 4795-4808).

Scheme 1

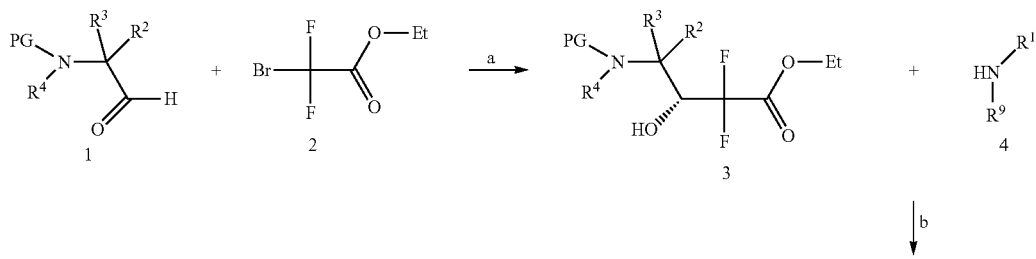

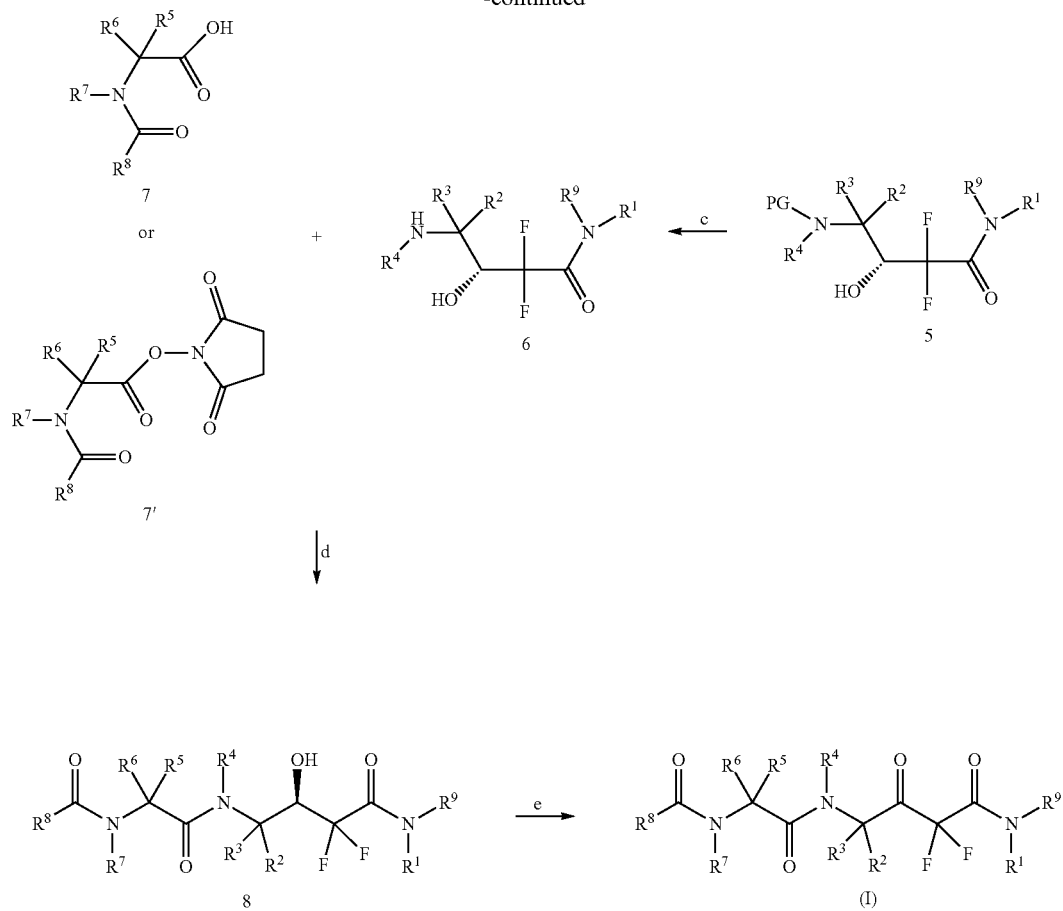

Building block 7 used in scheme 1 can be synthesized as summarized in scheme 2. The appropriate, commercially available amino acid 1 is transformed into the corresponding bis-silylated derivative 2 by treatment with two equivalents of trimethylsilyl chloride and a tertiary amine, e.g., TEA or Huenig's base (scheme 2, step a); or, if R7 unequal hydrogen, with one equivalent of trimethylsilyl chloride. The nitrogen of the latter is then acylated by treatment with the acid 3 and a conventional coupling reagent like HATU or TBTU and an appropriate base, e.g., Huenig's base, in an inert solvent like DCM, to give the anticipated intermediate (scheme 2, step b).

NETS-ester 7' of scheme 1 can be obtained from 7 by treatment with 1-hydroxypyrrolidine-2,5-dione, EDC, and pyridine in DCM at ambient temperature.

Scheme 2

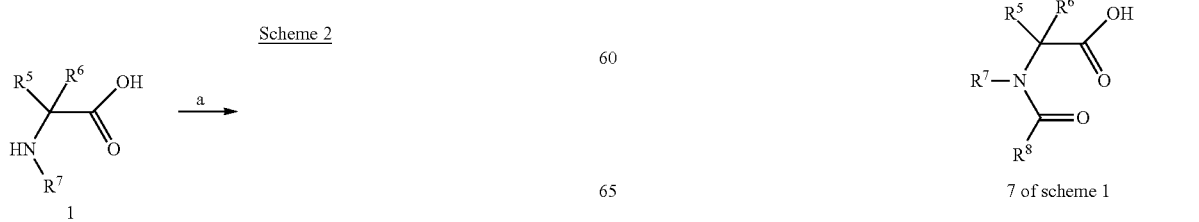

In another synthetic variant, as outlined in scheme 3, intermediate 6 of scheme 1 is first elongated with an appropriately protected, e.g., with the BOC-group, amino acid 1 under standard conditions by treatment with a coupling reagent such as TBTU, HATU, EDCI/HOBT, etc., and a base like Huenig's base or TEA in an inert solvent like N,N-dimethylformamide to yield 2 (scheme 3, step a). After deprotection to 3, e.g. by treatment with TFA or anhydrous HCl in dioxane (scheme 3, step b), the latter is coupled with NETS-ester 4 under Schotten Baumann-conditions in a mixture of, e.g., THF, DME, and water, in the presence of a mild base like NaHCO3, to generate the penultimate intermediate 5 (scheme 3, step c). Oxidation of the free alcohol, e.g., with Dess Martin periodinane, in an inert solvent like DCM, delivers finally the target molecule I. In still another embodiment, 3 can also be coupled with free acid 4' under classical peptide coupling conditions as described above.

Scheme 3

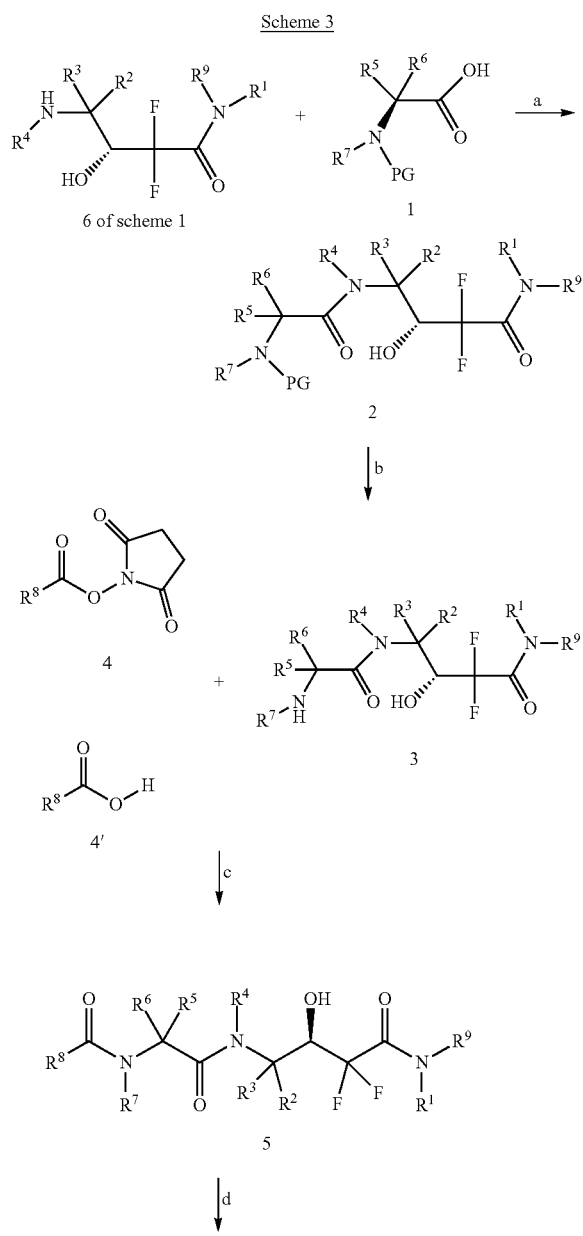

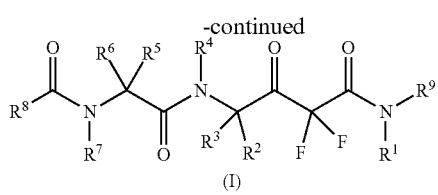

Acid 3 in scheme 2, identical to acid 4' in scheme 3, is either commercial available or can be prepared as follows:

In case these carboxylic acid derivatives belong to the family of beta-phenylsubstituted phenylpropanoic acid derivatives, these intermediates can be prepared by a variety of conditions which may be exemplified by the general synthetic procedures below, named here "Grignard route" and "Friedel-Crafts route" (scheme 4) and the preferred "Michael condensation route" (scheme 5). The person skilled in the art will appreciate that these compounds can also be prepared by variations of these procedures.

The optionally substituted phenyl cinnamic acids 1 react with phenyl-Grignard derivatives 2, optionally in the presence of catalytic amounts of CuI, in a solvent like diethylether and/or THF, and in a temperature range preferably between −10° C. and 0° C., to yield beta-phenylsubstituted phenylpropanoic acid compounds 3 (scheme 4, step a). However, the yields are often low and purification cumbersome. Alternatively, the very same substituted phenyl cinnamic acids 1 react with anisol 4 in the presence of a Brönstedt acid, such as para-toluene sulfonic acid, in a temperature range between about 50° C. and 150° C., preferably around 80° C., to produce beta-phenylsubstituted methoxyphenylpropanoic acid derivatives 5 (scheme 4, step b).

Scheme 4

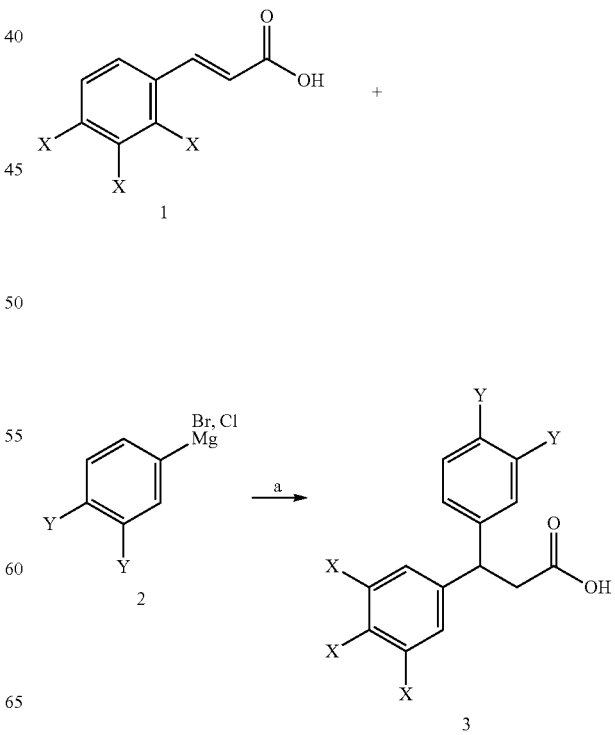

-continued

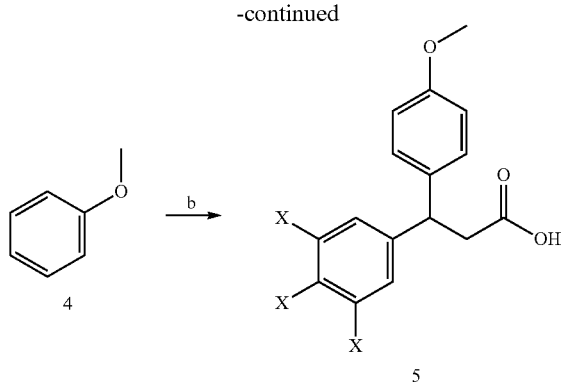

X is H, Cl or F
Y is H or OMe

In the preferred alternative (scheme 5), aromatic aldehyde derivatives 1 are condensed with alkyl-, preferred ethyl-2-cyanoacetate 2 in presence of a base such as sodium or potassium hydroxide pellets, in a solvent like EtOH, and around 0° C. to room temperature, to provide cyano-phenyl-cinnamic esters 3 (scheme 5, step a); only one stereoisomer is formed which is, however, irrelevant for the outcome of the synthesis. Subsequent Grignard reaction with phenyl magnesium derivatives 4 in the presence of catalytic amounts of CuI, in a solvent like $Et_2O$ and/or THF, and in a temperature range preferably between −10° C. and 0° C., produces compounds 5 (scheme 5, step b). Finally, exhaustive hydrolysis and decarboxylation under acidic conditions using, e.g., a mixture of acetic acid and sulfuric acid in water, in a temperature range between 100° C. and 120° C., preferably around reflux, gives the desired racemic beta-phenylsubstituted phenylpropanoic acid derivatives 6 (scheme 5, step c). Separation into the respective enantiomers can be accomplished by transforming them into NETS-ester 7 by treatment with 1-hydroxypyrrolidine-2,5-dione, EDC, and pyridine in DCM at ambient temperature (scheme 5, step d), followed by chiral HPLC. These active esters 4, either in homochiral or racemic form, are also used as reagents 4 in scheme 3.

Scheme 5

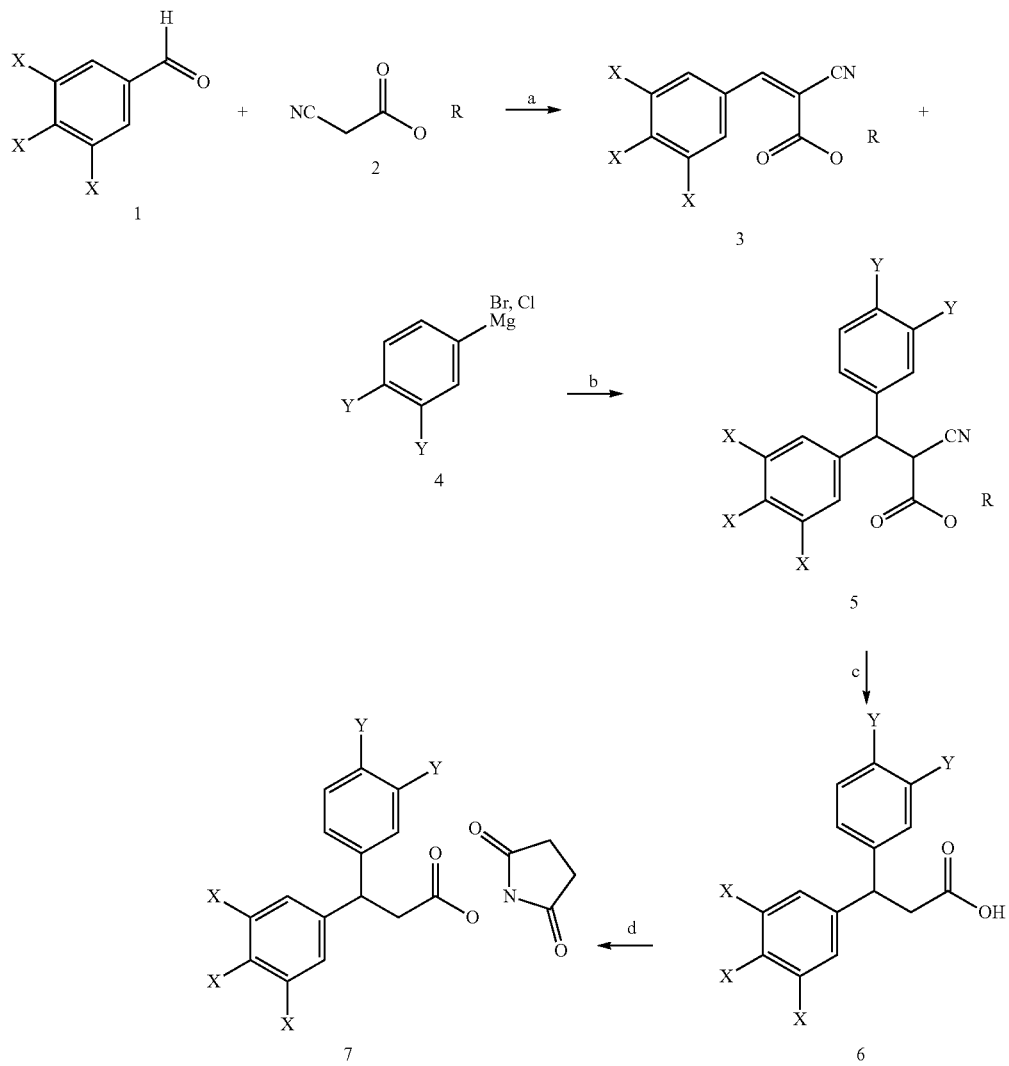

X is H, Cl, F, or OMe
Y is H, Cl, F, or OMe

In case the carboxylic acids 3 in scheme 2, identical to acid 4' in scheme 3, belong to the family of beta-phenoxy phenylpropanoic acid derivatives, these intermediates can be prepared by a variety of conditions, which may be exemplified by the general synthetic procedure summarized below (scheme 6): Commercially available allyl Grignard reagent is added to an appropriately substituted benzaldehyde 1 under standard conditions in THF in a temperature range preferably between −78° C. and 0° C. to yield benzylic alcohol 2 (scheme 6, step a). Ensuing Mitsunobu reaction between the latter and a suitable phenol derivative 3, using, e.g., DIAD and triphenylphosphine as reagents, in a solvent like THF and in a temperature range between 0° C. and room temperature, provides ether 4 (scheme 6, step b). Oxidative cleavage of the terminal alkene by means of, e.g., a mixture of sodium periodate and potassium permanganate in presence of a base such as potassium carbonate, in a solvent mixture like t-BuOH/water, and in a temperature range preferably between 0° C. and room temperature, eventually gives the desired beta substituted phenoxy phenylpropanoic acid derivative 5 (scheme 6, step c).

Scheme 6

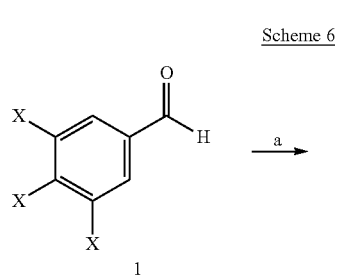

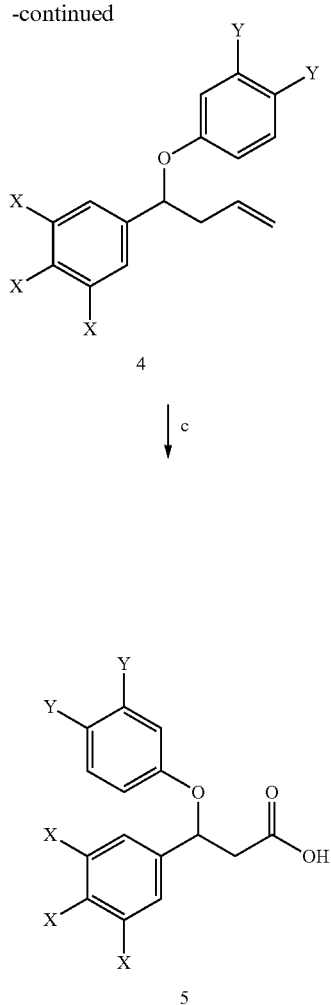

X is H, Cl, F, or MeO
Y is H, Cl, F, or OMe

Beta-aryloxy-carboxylic acids 5 of scheme 6 can be prepared in optically pure form in an analogous manner by using homochiral benzylic alcohol 2 in the Mitsunobu process which is well known to proceed by clean inversion. This building block can readily be prepared as outlined in scheme 7: Weinreb amide 1 is reacted with commercially available allyl Grignard reagent in THF/Et$_2$O in a temperature range preferably between −20° C. and ambient temperature to give ketone 2 (scheme 7, step a). Enantioselective reduction with (+)-diisopino-campheyl-chloroborane 3 in THF at a temperature range between −50° C. and ambient temperature provides (R)-benzylic alcohol 4 (scheme 7, step b, J. Org. Chem. 2002, 67, 9192-9199). Mitsunobu reaction as above with phenol 5 generates (S)-aryl-ether 6 (scheme 7, step c) which is again, as described above, oxidatively cleaved to (S)-acid 7 (scheme 7, step d). By relying on (−)-diisopino-campheyl-chloroborane ent-3, the other enantiomer is readily available as well.

Scheme 7

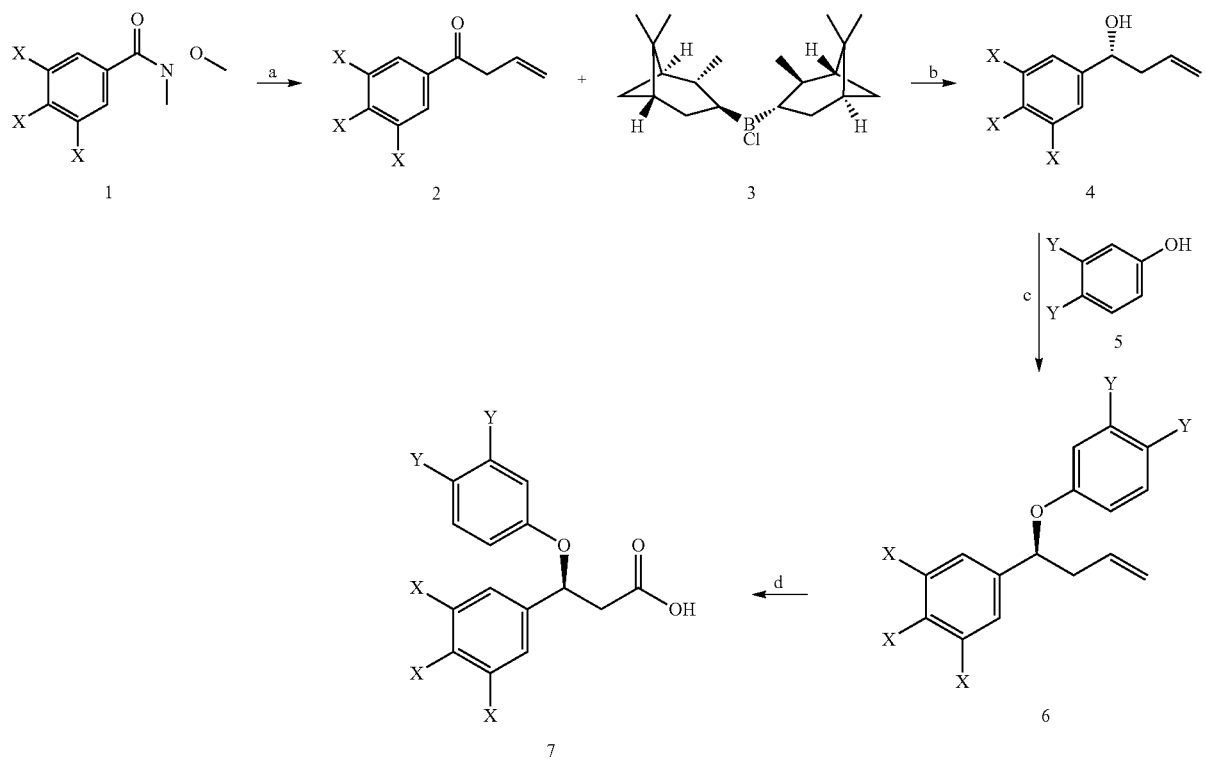

X is H, Cl, F, or MeO
Y is H, Cl, F, or OMe

Also an embodiment of the present invention is a process to prepare a compound of formula (I) as defined above comprising a) the reaction of a compound of formula (III) with a compound of formula (IV)

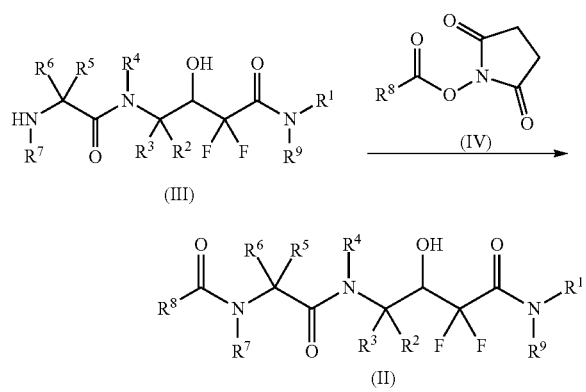

In particular, in the presence of a base, more particularly sodium carbonate, in a solvent like DME, THF and water or a mixture thereof between 0° C. and room temperature, particularly at room temperature.

then b) the reaction of a compound of formula (II) in oxidative conditions

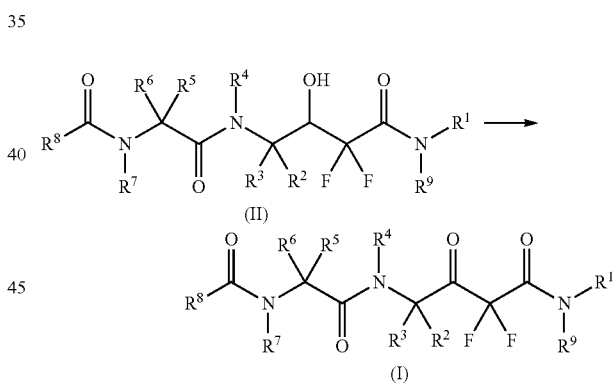

In particular, in the presence of 1,1,1-Triacetoxy-1,1-dihydro-1,2-benziodoxol-3(1H)-one (Dess-Martin periodane), in a solvent like DCM between 0° C. and room temperature.

wherein $R^1$, $R^2$, $R^3$, $R^4$, $R^5$, $R^6$, $R^7$, $R^8$ and $R^9$ are as defined herein.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of ocular diseases, in particular HtrA1-mediated ocular diseases, more particularly wet or dry age-related macular degeneration, geographic atrophy, diabetic retinopathy, retinopathy of prematurity or polypoidal choroidal vasculopathy.

In a particular embodiment, the compounds of formula (I) or their pharmaceutically acceptable salts and esters can be used for the treatment or prophylaxis of wet or dry age-related macular degeneration, geographic atrophy, diabetic retinopathy, retinopathy of prematurity or polypoidal choroidal vasculopathy.

The present invention also relates to the use of a compound according to formula (I) as described herein for the preparation of a medicament for the treatment or prophylaxis of wet or dry age-related macular degeneration, geographic atrophy, diabetic retinopathy, retinopathy of prematurity and polypoidal choroidal vasculopathy.

Also an object of the invention is a method for the treatment or prophylaxis of wet or dry age-related macular degeneration, geographic atrophy, diabetic retinopathy, retinopathy of prematurity and polypoidal choroidal vasculopathy, which method comprises administering an effective amount of a compound according to formula (I) as described herein.

Also an embodiment of the present invention are compounds of formula (I) as described herein, when manufactured according to any one of the described processes.

Assay Procedures

Protein Purification for Use in Enzymatic Assays

Human HtrA1 protein comprising the catalytic and the PDZ domain from amino acid Asp161 up to Pro480 of was expressed in BL21(DE3) cells as an N-terminal fusion protein with a 6×His-SUMO tag. The transformed cells were grown in LB medium at 37° C. until the optical density at 600 nm was between 0.6 and 0.8. Then, the temperature was decreased to 18° C. and the recombinant protein production induced by adding IPTG to a final concentration of 250 mM. Fermentation was performed over night at 18° C.

The protein was purified to homogeneity following a four-step procedure. 40 g of cells were suspended in 50 mM HEPES pH 7.8, 250 mM NaCl, 10 mM MgCl2, 0.35% CHAPS, 10% glycerol containing 20 tabs per liter of EDTA-free cOmplete Protease Inhibitor (Roche) as well as 30 mg/l DNAse and Rnase. The cells were broken by a single passage through a homogenizer at 750 bar and then centrifuged at 20,000×g for 30 minutes. The clear supernatant was applied on a triple 5 ml HisTrap column (GE Healthcare) equilibrated in 50 mM HEPES pH 7.8, 500 mM NaCl, 0.35% CHAPS, 10% glycerol. After washing with stepwise increasing concentrations of imidazole (20 mM, 40 mM, 50 mM) HtrA1 fusion protein was eluted within a linear gradient from 10 to 100% of the same buffer containing 500 mM imidazole. HtrA1 containing fractions were pooled, concentrated and then applied to a Superdex S200 prep grade (XK26/100-GE Healthcare) column equilibrated in 50 mM ethanolamine pH 9.6, 500 mM NaCl, 0.35% CHAPS, 10% glycerol, 0.02% sodium azide. In order to cleave the SUMO fusion protein and to release active HtrA1, the pooled fractions from the size exclusion chromatography were blended with SUMO protease (Life Technologies) and incubated ca. 20 hours at RT. HtrA1 was isolated out of the reaction solution by chromatography on a Superdex S200 prep grade (XK26/100-GE Healthcare) column equilibrated 50 mM ethanolamine pH 9.6, 500 mM NaCl, 0.35% CHAPS, 10% glycerol, 0.02% sodium azide. Fractions containing active HtrA1 were pooled and concentrated. Following the above strategy 150 mg of the HtrA1 (catalytical domain/PDZ construct) could be purified. As shown by RP-HPLC and SDS-PAGE, >98% pure protein was obtained.

HtrA1 Enzyme Inhibition Assay

Enzyme activity is measured by observing the increase in fluorescence intensity caused by cleavage of a peptide substrate containing a fluorophore, whose emission is quenched in the intact peptide.

Assay buffer: 500 mM Tris pH 8.0, 200 mM NaCl, 0.025% CHAPS, 0.005% BSG

Enzyme: human HtrA1 Cat-PDZ, final concentration 1 nM

Substrate: Mca-Ile-Arg-Arg-Val-Ser-Tyr-Ser-Phe-Lys (Dnp)-Lys, final concentration 500 nM (from Innovagen Cat: SP-5076-1, Lot: 89584.02)

Mca=(7-Methoxycoumarin-4-yl)acetyl

Dnp=2,4-Dinitrophenyl

Final volume: 51 µl

Excitation 320 nm, emission 390 nm

After a pre-incubation of the HtrA1 protease for 30 min with compounds, substrate is added to the wells and initial RFU is measured. Upon incubation for 2 hours at RT, the enzymatic activity cleaved the substrate releasing fluorescent Mca-peptide conjugate and the final RFU value is measured. The presence of inhibitors leads to a decreased final RFU.

For the analysis $\Delta$RFU is calculated as $RFU_{end} - RFU_{start}$ and then percent inhibition is calculated with the following formula:

$$PCT\_Inhibition = 100 - 100 * (xRFU_{compound} - \Delta RFU_{blank})/(\Delta RFU_{negctrl} - \Delta RFU_{blank})$$

where neg.ctrl is protease with substrate and DMSO blank is as neg. ctrl without protease compound is as neg. ctrl with test compounds at desired concentration The $IC_{50}$ is determined using a 4-point Hill-fit equation where x=concentration of test compound A=extrapolated value of the curve at effector concentration equals 0

B=extrapolated value of the curve at effector concentration equals infinite

C=concentration at the inflection point of the sigmoidal curve ($IC_{50}$)

D=Hill coefficient of slope at the inflection point of the fitted curve $$Y(x) = A + \frac{B - A}{1 + \left(\frac{C}{x}\right)^D}$$

As a counter screen the compounds are added to the protease-substrate reaction mix only after 2 h incubation, when all the substrate is turned over, to identify autofluorescent or absorbing compounds giving false positive hits.

| Example | IC50 (µM) |
|---------|-----------|
| 1 | 1.37 |
| 2 | 0.04 |
| 3 | 0.89 |

-continued

| Example | IC50 (μM) |
|---|---|
| 4 | 0.42 |
| 5 | 0.128 |
| 6 | 0.16 |
| 7 | 0.14 |
| 8 | 0.13 |
| 9 | 0.033 |
| 10 | 0.21 |
| 11 | 0.22 |
| 12 | 0.4 |
| 13 | 0.14 |
| 14 | 1.91 |
| 15 | 0.63 |
| 16 | 0.41 |
| 17 | 0.39 |
| 18 | 0.31 |
| 19 | 0.15 |
| 20 | 0.32 |
| 21 | 0.32 |
| 22 | 0.49 |
| 23 | 0.21 |
| 24 | 0.09 |
| 25 | 0.045 |
| 26 | 0.05 |
| 27 | 0.02 |
| 28 | 0.025 |
| 29 | 0.36 |
| 30 | 0.27 |
| 31 | 0.06 |
| 32 | 0.31 |
| 33 | 0.37 |
| 34 | 0.22 |
| 35 | 0.17 |
| 36 | 0.17 |
| 37 | 0.13 |
| 38 | 0.1 |
| 39 | 0.43 |
| 40 | 0.03 |
| 41 | 0.55 |
| 42 | 1.7 |
| 43 | 0.05 |
| 44 | 0.14 |
| 45 | 0.13 |
| 46 | 0.07 |
| 47 | 0.44 |
| 48 | 0.04 |
| 49 | 0.03 |
| 50 | 0.01 |
| 51 | 0.04 |
| 52 | 0.03 |
| 53 | 0.02 |
| 54 | 0.015 |
| 55 | 0.01 |
| 56 | 0.01 |
| 57 | 0.02 |
| 58 | 0.01 |
| 59 | 0.01 |
| 60 | 0.04 |
| 61 | 0.04 |
| 62 | 0.01 |
| 63 | 0.03 |
| 64 | 0.02 |
| 65 | 0.015 |
| 66 | 0.03 |
| 67 | 0.09 |
| 68 | 0.04 |
| 69 | 0.003 |
| 70 | 0.01 |
| 71 | 0.003 |
| 72 | 0.002 |
| 73 | 0.008 |
| 74 | 0.019 |
| 75 | 0.007 |
| 76 | 0.032 |
| 77 | 0.01 |
| 78 | 0.008 |
| 79 | 0.008 |
| 80 | 0.009 |

-continued

| Example | IC50 (μM) |
|---|---|
| 81 | 0.004 |
| 82 | 0.059 |
| 83 | 0.010 |
| 84 | 0.034 |
| 85 | 0.038 |
| 86 | 0.021 |
| 87 | 0.016 |
| 88 | 0.002 |
| 89 | 0.004 |
| 90 | 0.050 |
| 91 | 0.065 |
| 92 | 0.003 |
| 93 | 0.036 |
| 94 | 0.065 |
| 95 | 0.040 |
| 96 | 0.016 |
| 97 | 0.025 |
| 98 | 0.007 |

Compounds of formula (I) and their pharmaceutically acceptable salts or esters thereof as described herein have $IC_{50}$ values between 0.00001 μM and 1000 μM, particular compounds have $IC_{50}$ values between 0.0005 μM and 500 μM, further particular compounds have $IC_{50}$ values between 0.0005 μM and 50 μM, more particular compounds have $IC_{50}$ values between 0.0005 μM and 5 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations; lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg, can be administered either by single dose per day or per week, or by multiple doses (2 to 4) per day, or by multiple doses per week. In case of parenteral application, such as intramuscularly, intravenously, or intraocularly, the formulation can contain 0.001% to 15% by weight of medicament and the required dose, which can be between 0.01 and 25 mg, can be administered either by single dose per day, per week or per month, or by multiple doses (2 to 4) per day, or by multiple doses per week or per month. It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Intermediate Ia 3-(3,5-Dichlorophenyl)-3-(4-methoxyphenyl)propanoic Acid

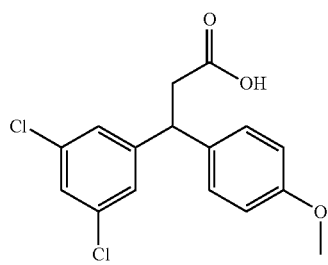 [SMILES: COc1ccc(C(CC(=O)O)c2cc(Cl)cc(Cl)c2)cc1]

[A] Ethyl (Z)-2-cyano-3-(3,5-dichlorophenyl)prop-2-enoate

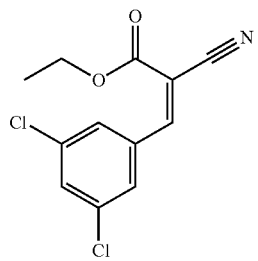 [SMILES: CCOC(=O)/C(C#N)=C\c1cc(Cl)cc(Cl)c1]

In a 50 mL pear-shaped flask, 3,5-dichlorobenzaldehyde (1.5 g, 8.57 mmol, Eq: 1) and ethyl 2-cyanoacetate (2.91 g, 2.74 ml, 25.7 mmol, Eq: 3) were combined with EtOH (10 ml) to give a colorless solution with some residual aldehyde (oversaturated); sodium hydroxide (171 mg, 4.29 mmol, Eq: 0.5) was added as pellets and the mixture stirred at ambient temperature and protected from water; TLC after 1.5 h indicated that the starting aldehyde had completely disappeared! The reaction mixture was poured onto crashed ice/2N HCl after 2 h; over night the product solidified; it was washed with water and recrystallized from EtOH to yield 0.785 g of the title compound as white solid; the NMR spectrum indicated the presence of only one double bond isomer, to which Z-configuration was assigned without proof. If desired, more product can be isolated from the mother liquor by column chromatography.

[B] Ethyl 2-cyano-3-(3,5-dichlorophenyl)-3-(4-methoxyphenyl)propanoate

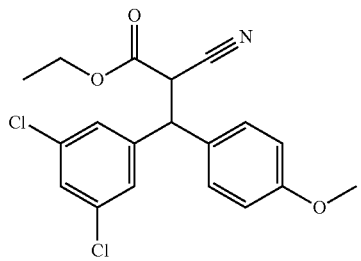 [SMILES: CCOC(=O)C(C#N)C(c1ccc(OC)cc1)c1cc(Cl)cc(Cl)c1]

In a 25 mL three-necked flask, copper (I) iodide (10.6 mg, 55.5 μmol, Eq: 0.1) was combined with diethyl ether (5 ml) to give a off-white suspension. At 0° C., (4-methoxyphenyl)magnesium bromide 0.5M in THF (2.22 ml, 1.11 mmol, Eq: 2) was added and after 10 min, a solution of the above prepared (Z)-ethyl 2-cyano-3-(3,5-dichlorophenyl)acrylate (150 mg, 555 μmol, Eq: 1) in tetrahydrofuran (4 ml) was added dropwise. The reaction mixture was stirred at 0° C. TLC after 1 h showed the reaction to be complete.

The reaction mixture (brown solution) was cooled to −75° C. and quenched with 5 ml sat. NH4Cl sol. The cooling bath was removed after 5 min and the mixture was allowed to warm to room temperature. EtOAc extraction, washing with H$_2$O/NaCl sol., drying and concentration in vacuo, followed by flash chromatography (silica gel, 20 g, 17% EtOAc in heptane) yielded 168 mg of the title compound as colorless oil; MS: 376.2 (M–H)$^-$.

[C] 3-(3,5-Dichlorophenyl)-3-(4-methoxyphenyl) propanoic Acid

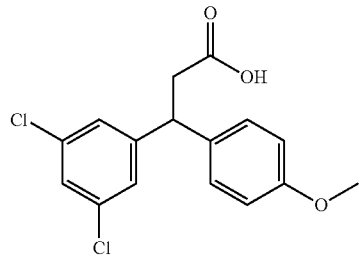 [SMILES: COc1ccc(C(CC(=O)O)c2cc(Cl)cc(Cl)c2)cc1]

To a mixture of ethyl 2-cyano-3-(3,5-dichlorophenyl)-3-(4-methoxyphenyl)propanoate (162 mg, 428 µmol, Eq: 1), acetic acid (2 ml) and $H_2O$ (1 ml) was added under ice-bath cooling $H_2SO_4$ conc (1 ml). The reaction mixture was stirred for 23 hr at 105° C. Heating was stopped and the reaction mixture was allowed to cool down to rt, poured onto crashed ice and extracted with AcOEt (2×). The organic layers were washed with $H_2O$/NaCl sol., dried over $Na_2SO_4$ and concentrated in vacuo. The crude material was purified by flash chromatography (silica gel, 20 g, 30% to 80% EtOAc in heptane) to give 113 mg of the title product as colorless oil; MS: 649.3 (2M−H)⁻.

In close analogy can be prepared:

Intermediate Ib 3-(3,4-dichlorophenyl)-3-(4-methoxyphenyl)propanoic Acid

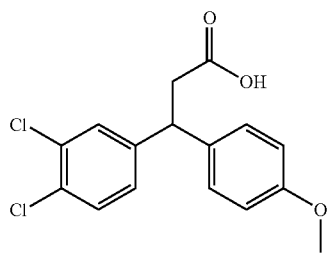 [SMILES: COc1ccc(C(CC(=O)O)c2ccc(Cl)c(Cl)c2)cc1]

As colorless oil, MS: 323.1 (M−H).

Intermediate Ic 3-(3,4-Dichlorophenyl)-3-phenylpropanoic Acid

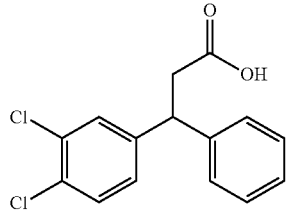 [SMILES: O=C(O)CC(c1ccccc1)c1ccc(Cl)c(Cl)c1]

As light brown oil, MS: 589.2 (2M−H)⁻.

Intermediate Id 3-(3,5-dichlorophenyl)-3-phenylpropanoic Acid

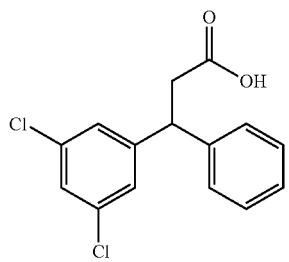 [SMILES: O=C(O)CC(c1ccccc1)c1cc(Cl)cc(Cl)c1]

As white semisolid; MS: 589.2 (M−H)⁻.

Intermediate Ie 3-(4-Bromophenyl)-3-phenylpropanoic Acid

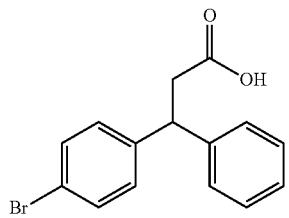 [SMILES: O=C(O)CC(c1ccccc1)c1ccc(Br)cc1]

As off-white semisolid; MS: 609.2 (2M−H)⁻.

Intermediate If 3-(3,5-Difluorophenyl)-3-(4-methoxyphenyl)propanoic acid

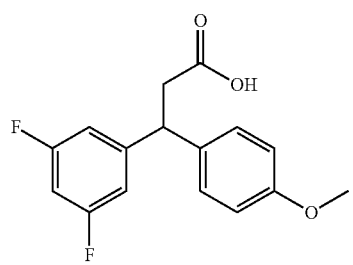 [SMILES: COc1ccc(C(CC(=O)O)c2cc(F)cc(F)c2)cc1]

As light yellow oil; MS: 291.1 (M−H)⁻.

Intermediate Ig 3-(3-chlorophenyl)-3-phenylpropanoic Acid

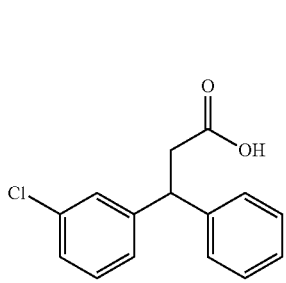 [SMILES: O=C(O)CC(c1ccccc1)c1cccc(Cl)c1]

As colorless oil, MS: 259.1 (M–H).

Intermediate IIa 3-(3,4-Dichlorophenyl)-3-phenoxypropanoic Acid

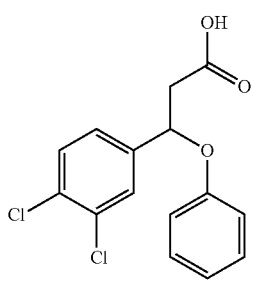

[A] 1,2-Dichloro-4-(1-phenoxybut-3-enyl)benzene

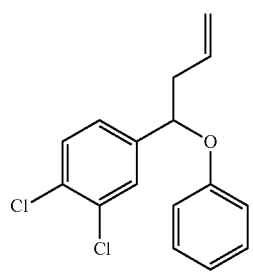 [SMILES: C=CCC(Oc1ccccc1)c1ccc(Cl)c(Cl)c1]

In a 25 mL three-necked flask, 1-(3,4-dichlorophenyl)but-3-en-1-ol (267 mg, 1.23 mmol, Eq: 1) was combined with DCM (12 ml) to give a colorless solution. Phenol (127 mg, 1.35 mmol, Eq: 1.1) and triphenylphosphine (419 mg, 1.6 mmol, Eq: 1.3) were added and the reaction mixture was cooled to 0° C. DIAD (323 mg, 311 µl, 1.6 mmol, Eq: 1.3) was added at +1.5<T° C.>+3° C. within 20 min. The reaction mixture was stirred for 30 min at 0° C., then for 1 hr at rt. The crude reaction mixture was concentrated in vacuo and directly purified by flash chromatography (silica gel, 50 g, 1% to 10% EtOAc in heptane) to provide 263 mg of the title compound as colorless liquid; MS: 291.1 (M–H)⁻.

[B] 3-(3,4-Dichlorophenyl)-3-phenoxypropanoic Acid

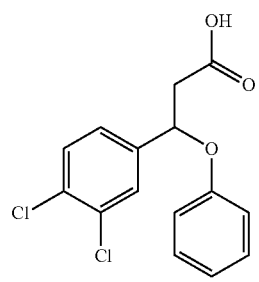 [SMILES: O=C(O)CC(Oc1ccccc1)c1ccc(Cl)c(Cl)c1]

A solution of sodium periodate (1.69 g, 7.92 mmol, Eq: 9) in water (35 ml) was treated with potassium permanganate (55.6 mg, 352 µmol, Eq: 0.4), potassium carbonate (1.82 g, 13.2 mmol, Eq: 15) and tBuOH (4 ml). To this mixture, a solution of the above prepared 1,2-dichloro-4-(1-phenoxybut-3-en-1-yl)benzene (258 mg, 880 µmol, Eq: 1) in tBuOH (9 ml) was slowly added at ~+5° C. and the resulting mixture was stirred at rt for 3 h when LC-MS and TLC indicated some remaining starting material. A solution of potassium permanganate (55.6 mg, 352 µmol, Eq: 0.4) in 5 ml H$_2$O was added and the reaction mixture was again stirred at rt for additional 1 hr. LC-MS and TLC now showed the reaction to be finished. The mixture was treated with ethylene glycol (1.11 g, 1 ml, 17.9 mmol, Eq: 20.4), stirred for 1 hr and acidified to pH 2 with 25% HCl at 0° C.

The resulting brown solid was filtered off and the filtrate was extracted with AcOEt (2×). The organic layer was washed with brine, then dried over Na$_2$SO$_4$, and concentrated under reduced pressure. The crude material was purified by flash chromatography (silica gel, 20 g, 20% to 100% EtOAc in heptane) to provide 146 mg of the title acid as light yellow oil; MS: 621.2 (2M–H)⁻.

In close analogy, using the appropriate, commercially available building block, was prepared:

Intermediate IIb 3-(4-Chlorophenoxy)-3-(3,4-dichlorophenyl)propanoic Acid

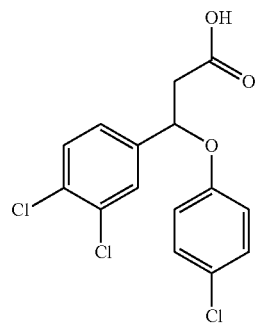 [SMILES: O=C(O)CC(Oc1ccc(Cl)cc1)c1ccc(Cl)c(Cl)c1]

As yellow gum, MS: 689.1 (2M–H)⁻.

Intermediate IIc

(3S)-3-(3-Chlorophenoxy)-3-phenylpropanoic Acid

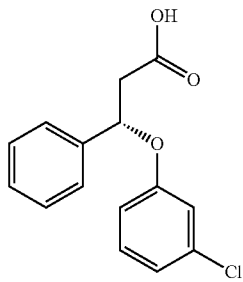 [SMILES: O=C(O)C[C@H](Oc1cccc(Cl)c1)c1ccccc1]

[A] (1R)-1-Phenylbut-3-en-1-ol

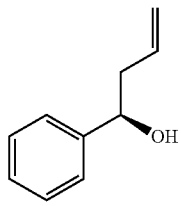

In a 50 mL four-necked flask, (+)-Diisopinocampheylchloroborane (3.79 g, 11.8 mmol, Eq: 1.2) was combined with Tetrahydrofuran (10 ml) to give a colorless solution. At ~−50° C. a solution of 1-phenylbut-3-en-1-one (1.8 g, 9.85 mmol, Eq: 1) in Tetrahydrofuran (5 ml) was added dropwise. The reaction mixture was allowed to slowly warm to rt over a week-end. The crude reaction mixture was concentrated in vacuo and then 10 min on hv at 40° C. to remove the (−) alpha-pinene formed during the reacion. The remaining residue was dissolved in TBME (50 ml) and treated with 3M aqueous HCl (50 ml). The mixture was stirred 5 min at rt and transferred into a separation funnel. The aqueous layer was back-extracted with tBuOMe, the organic layers were washed with brine, combined, dried over Na2SO4 and concentrated in vacuo. The crude material was purified by flash chromatography (silica gel, 100 g, 5% to 30% EtOAc in heptane) to yield 1.206 g of the title compound as light yellow liquid; chiral HPLC (Chiralcel OD, heptane/ethanol/isopropanol) confirmed the optical purity to be >>95%.

[B] 1-Chloro-3-[(1S)-1-phenylbut-3-enoxy]benzene

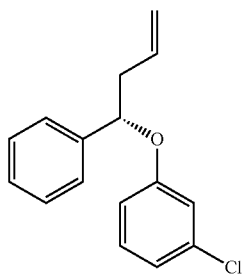 [SMILES: C=CC[C@H](Oc1cccc(Cl)c1)c1ccccc1]

In a 50 mL three-necked flask, the above prepared (R)-1-phenylbut-3-en-1-ol (300 mg, 2.02 mmol, Eq: 1) was combined with Dichloromethane (20 ml) to give a colorless solution. 3-Chlorophenol (286 mg, 230 µl, 2.23 mmol, Eq: 1.1) and triphenylphosphine (690 mg, 2.63 mmol, Eq: 1.3) were added successively. The reaction mixture was cooled to 0° C. and DIAD (532 mg, 512 µl, 2.63 mmol, Eq: 1.3) was added while keeping the temperature below 5° C. within 10 min, and the reaction was allowed to proceed for 30 min at 0° C. and 1 hr at rt. The crude reaction mixture was then concentrated in vacuo and directly purified by flash chromatography (silica gel, 50 g, 1% to 5% EtOAc in heptane) to afford 226 mg of the title compound as colorless liquid.

[C] (3S)-3-(3-Chlorophenoxy)-3-phenylpropanoic Acid

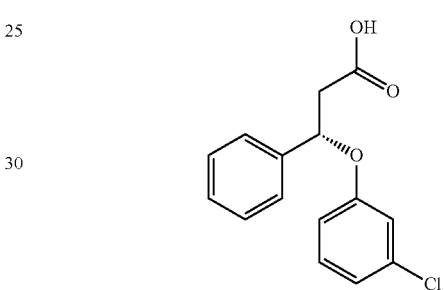

A solution of sodium periodate (1.65 g, 7.72 mmol, Eq: 9) in Water (30 ml) was treated with potassium permanganate (54.2 mg, 343 µmol, Eq: 0.4), potassium carbonate (1.78 g, 12.9 mmol, Eq: 15) and tBuOH (4 ml). To this mixture, a solution of the above prepared (S)-1-chloro-3-((1-phenylbut-3-en-1-yl)oxy)benzene (222 mg, 858 µmol, Eq: 1) in tBuOH (9 ml) was slowly added at ~+5° C. and the resulting mixture was stirred at rt for 3 h when LC-MS and TLC showed some starting material still to be present. Therefore, another solution of potassium permanganate (54.2 mg, 343 µmol, Eq: 0.4) in 5 ml $H_2O$ was added and the reaction mixture was stirred at rt for 1 additional hr; LC-MS and TLC indicated now the reaction to be finished. The reaction mixture was treated with ethylene glycol (1.11 g, 1 ml, 17.9 mmol, Eq: 20.9), stirred for 1 hr and acidified to pH 2 with 25% HCl at 0° C. (3 ml). The resulting brown solid was filtered off, and the filtrate was extracted with AcOEt (2×). The organic layer was washed with brine, then dried over $Na_2SO_4$ and concentrated under reduced pressure. The crude material was purified by flash chromatography (silica gel, 50 g, 20% to 100% EtOAc in heptane) to give 151 mg of the title acid as light yellow oil; MS: 275.1 (M−H)⁻.

Intermediate IId 3-(3-Chlorophenoxy)-3-(3,4-dichlorophenyl)propanoic acid

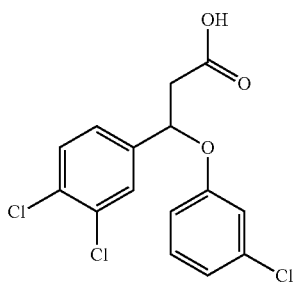 [SMILES: O=C(O)CC(Oc1cccc(Cl)c1)c1ccc(Cl)c(Cl)c1]

Was prepared in analogy to Intermediate IIb, using 3-chlorophenol instead of 4-chlorophenol as building block, as light yellow waxy solid; MS: 687.0 (2M−H)⁻.

Intermediate IIe (3R)-3-(3-Chlorophenoxy)-3-phenylpropanoic Acid

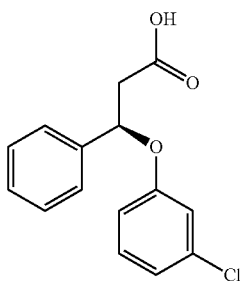 [SMILES: O=C(O)C[C@@H](Oc1cccc(Cl)c1)c1ccccc1]

Was prepared in analogy to Intermediate IIc, but using (−)-Diisopinocampheylchloroborane as reducing agent, as colorless oil; MS: 275.1 (M−H)⁻.

Intermediate IIf (3S)-3-(4-Chlorophenoxy)-3-(3,4-dichlorophenyl)propanoic acid

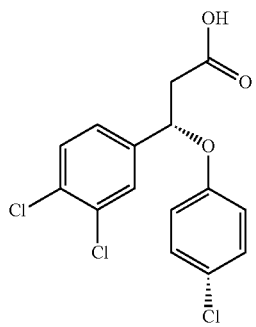

Was prepared in analogy to Intermediate IIc, but starting the reaction sequence with 1-(3,4-dichlorophenyl)but-3-en-1-one and using for the Mitsunobu reaction 4-chlorophenol as building block, as off-white semisolid; MS: 687.1 (2M−H)⁻.

Intermediate IIg 3-(3-Chlorophenoxy)-3-(5-chloropyridin-3-yl)propanoic Acid

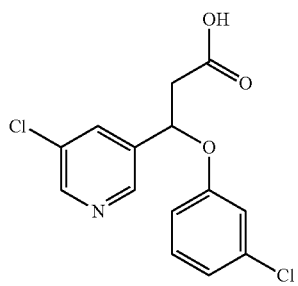 [SMILES: O=C(O)CC(Oc1cccc(Cl)c1)c1cncc(Cl)c1]

Was prepared in analogy to Intermediate IIb, but using 1-(5-chloropyridin-3-yl)but-3-en-1-ol and 3-chlorophenol as building block, respectively, as yellow oil; MS: 310.1 (M−H)⁻.

Intermediate IIh 3-(3-chlorophenyl)-3-pyridin-3-yloxypropanoic acid

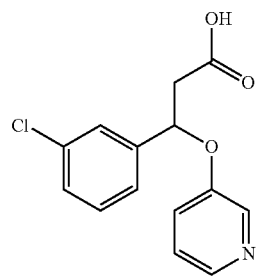 [SMILES: O=C(O)CC(Oc1cccnc1)c1cccc(Cl)c1]

Was prepared in analogy to Intermediate IIb, but using 1-(3-chlorophenyl)but-3-en-1-ol and pyridin-3-ol as building block, respectively, as white solid; MS: 276.2 (M−H)⁻.

Intermediate IIi 3-(3-chlorophenyl)-3-(5-chloropyridin-3-yl)oxypropanoic Acid

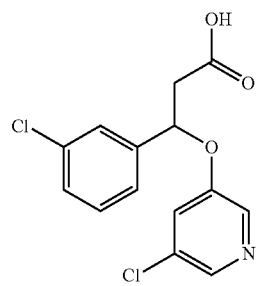 [SMILES: O=C(O)CC(Oc1cncc(Cl)c1)c1cccc(Cl)c1]

Was prepared in analogy to Intermediate IIb, but using 1-(3-chlorophenyl)but-3-en-1-ol and 5-chloropyridin-3-ol as building block, respectively, as yellow foam; MS: 312.0 (M–H)⁻.

Intermediate IIIa tert-Butyl N-[(3S,4R)-5,5-difluoro-4-hydroxy-2-methyl-6-oxo-6-(2,2,2-trifluoroethylamino)hexan-3-yl]carbamate

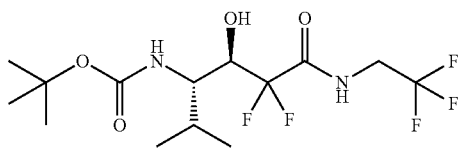 [SMILES: CC(C)[C@H](NC(=O)OC(C)(C)C)[C@@H](O)C(F)(F)C(=O)NCC(F)(F)F]

[A] Ethyl (3R,4S)-4-amino-2,2-difluoro-3-hydroxy-5-methylhexanoate

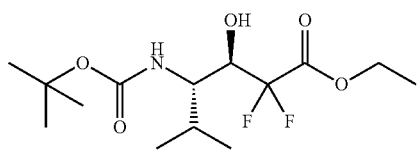 [SMILES: CCOC(=O)C(F)(F)[C@H](O)[C@@H](NC(=O)OC(C)(C)C)C(C)C]

A solution of (S)-tert-butyl (3-methyl-1-oxobutan-2-yl)carbamate (2.01 g, 9.99 mmol, Eq: 1) and ethyl 2-bromo-2,2-difluoroacetate (6.08 g, 3.84 ml, 30 mmol, Eq: 3) in THF (15 ml) was added dropwise to a suspension of activated zinc (1.96 g, 30 mmol, Eq: 3) in THF (65 ml). Afterwards, the reaction was brought to reflux for 2 hours. The heat source was removed and the reaction was allowed to cool to ambient temperature. The reaction mixture was poured into 15 mL 1N KHSO₄ and extracted with EtOAc (2×25 mL). The organic layers were combined, washed with brine, dried over Na₂SO₄ and concentrated in vacuo. The crude material was purified by flash chromatography (silica gel, 120 g, 20% EtOAc in heptane) to deliver 1.41 g of the title compound as colorless oil.

[B] tert-butyl N-[(3S,4R)-5,5-difluoro-4-hydroxy-2-methyl-6-oxo-6-(2,2,2-trifluoroethylamino)hexan-3-yl]carbamate

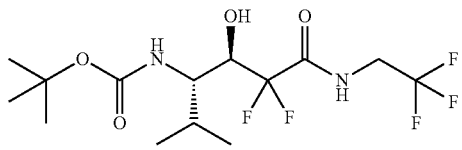 [SMILES: CC(C)[C@H](NC(=O)OC(C)(C)C)[C@@H](O)C(F)(F)C(=O)NCC(F)(F)F]

A mixture of the above prepared ethyl (3R,4S)-4-amino-2,2-difluoro-3-hydroxy-5-methylhexanoate (191.4 mg, 588 µmol, Eq: 1),3,3,3-trifluoropropan-1-amine (333 mg, 2.94 mmol, Eq: 5) and N,N-diisopropylethylamine (380 mg, 514 µl, 2.94 mmol, Eq: 5) was refluxed in 5 mL of MeOH overnight. TLC after 17 hours showed the reaction to be complete. The reaction volume was reduced in vacuo and to the residue was added EtOAc. The organic layer was washed with brine (3×), dried over Na₂SO₄ and concentrated in vacuo. The crude material was purified by flash chromatography (silica gel, 20 g, 15% to 50% EtOAc in heptane) to produce 180 mg of the title compound as white foam; MS: 391.4 (M–H)⁻.

[C] (3R,4S)-4-Amino-2,2-difluoro-3-hydroxy-5-methyl-N-(2,2,2-trifluoroethyl)hexanamide

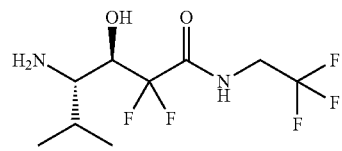 [SMILES: CC(C)[C@H](N)[C@@H](O)C(F)(F)C(=O)NCC(F)(F)F]

In a 25 mL round-bottomed flask, the above prepared tert-butyl N-[(3S,4R)-5,5-difluoro-4-hydroxy-2-methyl-6-oxo-6-(2,2,2-trifluoroethylamino)hexan-3-yl]carbamate (177 mg, 451 µmol, Eq: 1) was combined with 1,4-dioxane (6 ml) to give a colorless solution.

HCl 4M in dioxane (2.25 ml, 9 mmol, Eq: 20) was added at 0° C. and the reaction mixture was stirred overnight at rt. The crude reaction mixture was concentrated in vacuo and scrupulously dried on hv and then used directly for the next step.

In close analogy, using the appropriate, commercially available amine component, was prepared:

Intermediate IIIb (3R,4S)-4-Amino-2,2-difluoro-3-hydroxy-5-methyl-N-(3,3,3-trifluoropropyl)hexanamide

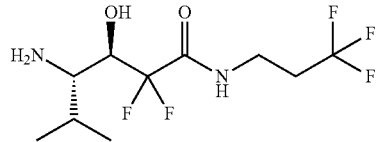 [SMILES: CC(C)[C@H](N)[C@@H](O)C(F)(F)C(=O)NCCC(F)(F)F]

As colorless oil, MS: 293.2 (M+H)⁺.

Intermediate IIIc (3R,4S)-4-Amino-2,2-difluoro-3-hydroxy-5-methyl-N-(2-morpholin-4-ylethyl)hexanamide

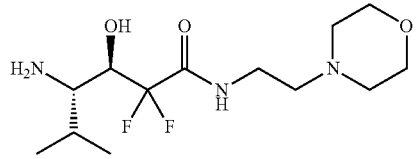 [SMILES: CC(C)[C@H](N)[C@@H](O)C(F)(F)C(=O)NCCN1CCOCC1]

As white foam, MS: 310.3 (M+H)⁺.

Intermediate IIId (3R,4S)-4-Amino-2,2-difluoro-3-hydroxy-5-methyl-N-(2-phenylethyl)hexanamide

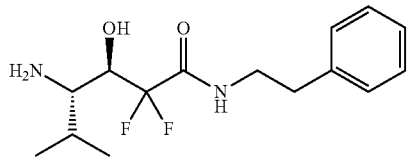 [SMILES: CC(C)[C@H](N)[C@@H](O)C(F)(F)C(=O)NCCc1ccccc1]

As light yellow oil, MS: 301.3 (M+H)$^+$.

Intermediate IIIe (3R,4S)-4-Amino-N-ethyl-2,2-difluoro-3-hydroxy-5-methylhexanamide

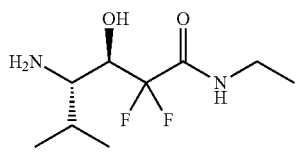

As colorless oil.

Intermediate IIIf (3R,4S)-4-Amino-2,2-difluoro-3-hydroxy-5-methyl-N-propylhexanamide

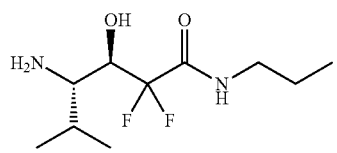 [SMILES: CCCNC(=O)C(F)(F)[C@H](O)[C@@H](N)C(C)C]

As colorless oil.

Intermediate IIIg (3R,4S)-4-Amino-2,2-difluoro-3-hydroxy-5-methyl-N-(2-methylpropyl)hexanamide

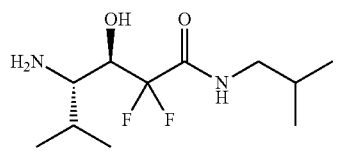 [SMILES: CC(C)CNC(=O)C(F)(F)[C@H](O)[C@@H](N)C(C)C]

As white foam.

Intermediate IIIh (3R,4S)-4-Amino-N-(2,2-dimethylpropyl)-2,2-difluoro-3-hydroxy-5-methylhexanamide

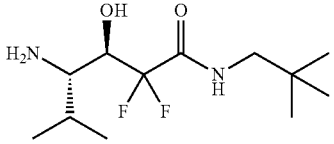 [SMILES: CC(C)[C@H](N)[C@@H](O)C(F)(F)C(=O)NCC(C)(C)C]

As white foam.

Intermediate IVa (2S)-2-[3-(3-Chlorophenyl)propanoylamino]-3-phenylpropanoic acid

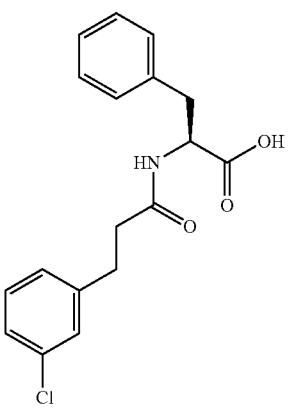 [SMILES: O=C(CCc1cccc(Cl)c1)N[C@@H](Cc1ccccc1)C(=O)O]

In a 50 mL round-bottomed flask, (S)-2-amino-3-phenyl-propanoic acid (1 g, 6.05 mmol, Eq: 1) was combined with DCM (30 ml) to give a white suspension; N,N-diisopropylethylamine (2.35 g, 3.17 ml, 18.2 mmol, Eq: 3) and trimethylchlorosilane (1.38 g, 1.62 ml, 12.7 mmol, Eq: 2.1) were added at 0° C. and the reaction stirred for 15 minutes at rt to give a colorless solution.

In a second, 250 mL round-bottomed flask, 3-(3-chlorophenyl)propanoic acid (1.12 g, 6.05 mmol, Eq: 1) was combined with DMF (30 ml) to give a colorless solution; N,N-diisopropylethylamine (939 mg, 1.27 ml, 7.26 mmol, Eq: 1.2) and TBTU were added and the mixture was stirred for 20 minutes. The above prepared solution from "flask 1" was added and the reaction was allowed to proceed for another 3 hours.

It was then poured into H$_2$O and extracted with DCM (2×). The organic layers were combined, washed with KHSO$_4$ sol and brine, dried over Na$_2$SO$_4$, and concentrated in vacuo.

Purification by flash chromatography (silica gel, 100 g, 2% to 10% MeOH in DCM), followed by trituration from AcOEt/heptane, afforded the pure title product as pink powder; MS: 332.2 (M+H)$^+$.

In close analogy, using commercially available building blocks or the appropriate intermediates I, was prepared:

Intermediate IVb (2S)-2-[3-(3,5-Dichlorophenyl)propanoylamino]-3-phenylpropanoic Acid

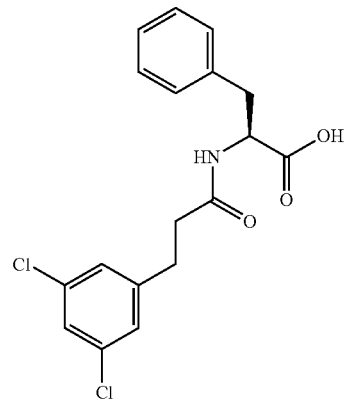 [SMILES: O=C(CCc1cc(Cl)cc(Cl)c1)N[C@@H](Cc1ccccc1)C(=O)O]

As off-white solid; MS: 366.1 (M+H)+.

Intermediate IVc (2S)-2-[[2-(3-Chlorophenoxy)acetyl]amino]-3-phenylpropanoic Acid

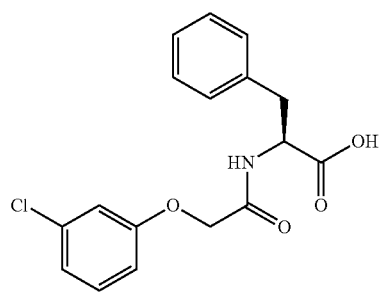 [SMILES: O=C(COc1cccc(Cl)c1)N[C@@H](Cc1ccccc1)C(=O)O]

As white solid; MS: 334.2 (M+H)+.

Intermediate IVd (2S)-2-[[2-(3,4-Dichlorophenoxy)acetyl]amino]-3-phenylpropanoic acid

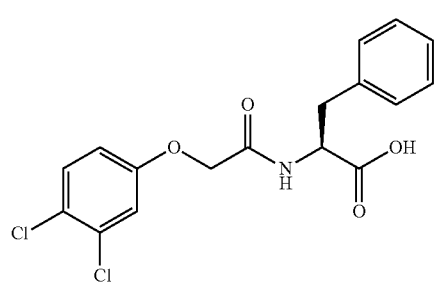 [SMILES: O=C(COc1ccc(Cl)c(Cl)c1)N[C@@H](Cc1ccccc1)C(=O)O]

As white solid; MS: 368.1 (M+H)+.

Intermediate IVe (2S)-2-[3-(3,4-Dichlorophenyl)propanoylamino]-3-phenylpropanoic Acid

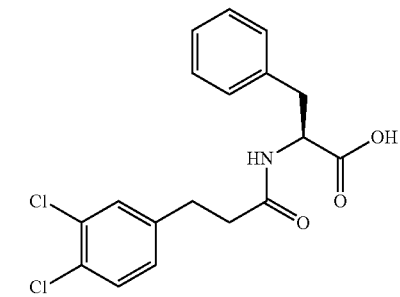 [SMILES: O=C(CCc1ccc(Cl)c(Cl)c1)N[C@@H](Cc1ccccc1)C(=O)O]

As off-white solid; MS: 366.1 (M+H)+.

Intermediate IVf (2S)-3-(4-Chlorophenyl)-2-[3-(3,4-dichlorophenyl)propanoylamino]propanoic acid

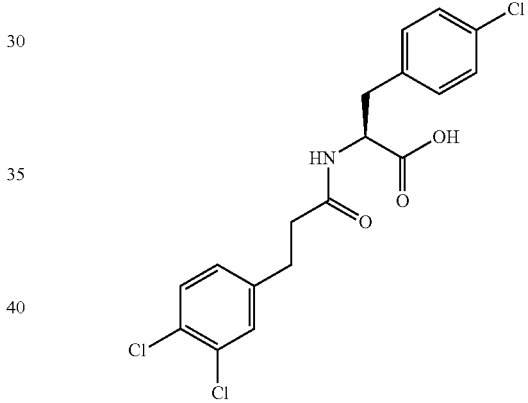

As off-white solid; MS: 400.1 (M+H)+.

Intermediate IVg (2S)-2-[3-(3,4-Dichlorophenyl)propanoylamino]-3-(3,4-dimethoxyphenyl)propanoic Acid

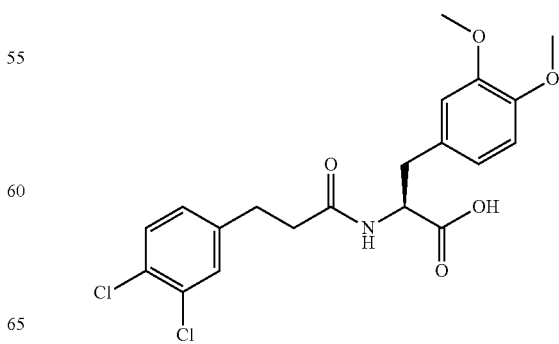

As off-white solid; MS: 426.2 (M+H)+.

47

Intermediate IVh (2S)-3-(3,4-Dichlorophenyl)-2-[3-(3,4-dichlorophenyl)propanoylamino]propanoic acid

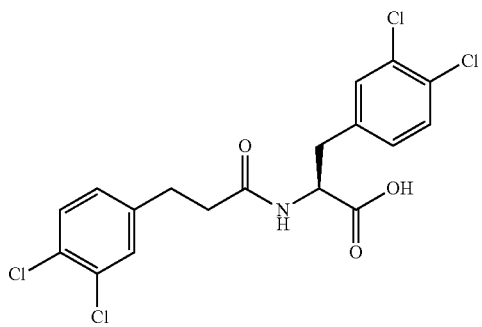 [SMILES: O=C(CCc1ccc(Cl)c(Cl)c1)N[C@@H](Cc1ccc(Cl)c(Cl)c1)C(=O)O]

As off-white solid; MS: 434.1 (M+H)+.

Intermediate IVi (2S)-2-[[2-(3,5-Dichlorophenoxy)acetyl]amino]-3-(3,4-dichlorophenyl)propanoic Acid

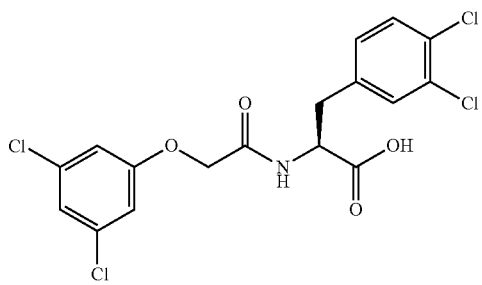 [SMILES: O=C(COc1cc(Cl)cc(Cl)c1)N[C@@H](Cc1ccc(Cl)c(Cl)c1)C(=O)O]

As off-white solid; MS: 434.1 (M−H).

Intermediate IVj (2S)-3-(4-Chlorophenyl)-2-[[2-(3,5-dichlorophenoxy)acetyl]amino]propanoic acid

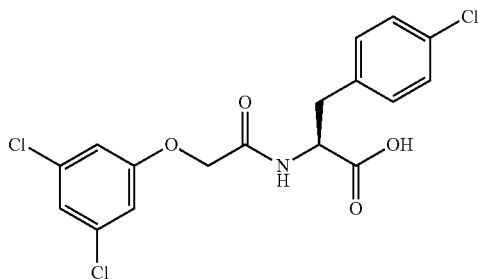 [SMILES: O=C(COc1cc(Cl)cc(Cl)c1)N[C@@H](Cc1ccc(Cl)cc1)C(=O)O]

As off-white solid; MS: 402.2 (M+H)+.

48

Intermediate IVk (2S)-2-[[2-(3,5-Dichlorophenoxy)acetyl]amino]-3-(3,4-difluorophenyl)propanoic Acid

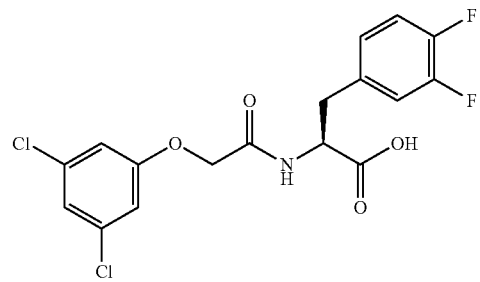 [SMILES: O=C(COc1cc(Cl)cc(Cl)c1)N[C@@H](Cc1ccc(F)c(F)c1)C(=O)O]

As off-white solid; MS: 402.2 (M−H).

Intermediate IVl (2S)-2-[[2-(3,5-Dichlorophenoxy)acetyl]amino]-3-(3,4-dimethoxyphenyl)propanoic acid

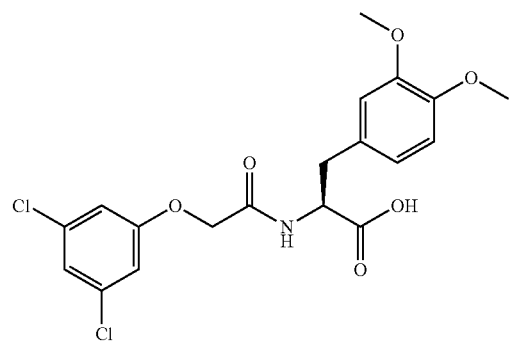 [SMILES: COc1ccc(C[C@H](NC(=O)COc2cc(Cl)cc(Cl)c2)C(=O)O)cc1OC]

As off-white solid; MS: 428.2 (M+H)+.

Intermediate IVm (2S)-2-[[2-(3,5-Dichlorophenoxy)acetyl]]-3-phenyl-propanoic Acid

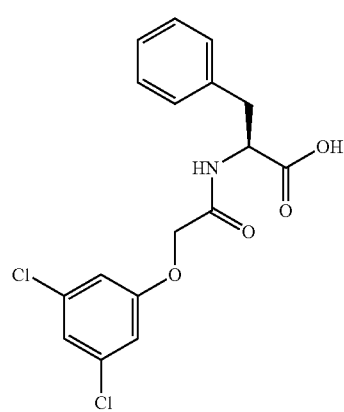

As off-white solid; MS: 368.1 (M+H)+.

49

Intermediate IVn (2S)-2-[[2-(3,5-dichlorophenoxy)acetyl]amino]-2-phenylacetic acid

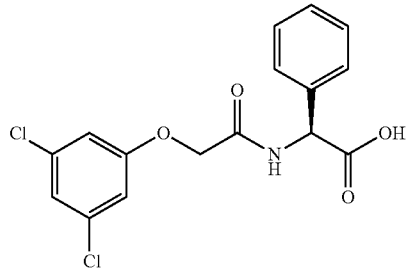 [SMILES: O=C(COc1cc(Cl)cc(Cl)c1)N[C@H](C(=O)O)c1ccccc1]

As off-white solid; MS: 354.0 (M+H)$^+$.

Intermediate IVo (2S)-2-[[2-(3,5-dichlorophenoxy)acetyl]amino]-2-(4-fluorophenyl)acetic Acid

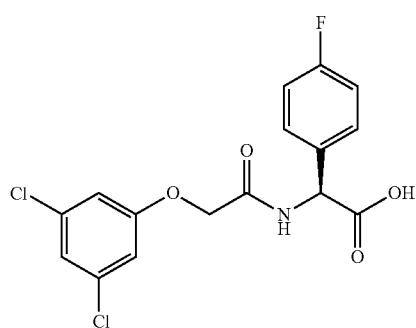

As off-white solid; MS: 354.0 (M+H)$^+$.

Intermediate IVp (2S)-2-[[3-(3,4-Dichlorophenyl)-3-phenylpropanoyl]amino]-3-phenylpropanoic acid

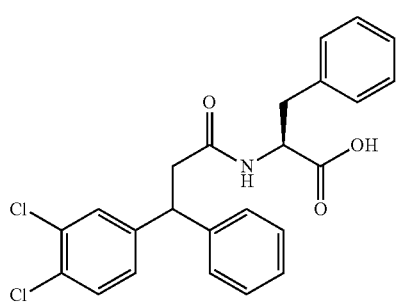 [SMILES: O=C(CC(c1ccccc1)c1ccc(Cl)c(Cl)c1)N[C@@H](Cc1ccccc1)C(=O)O]

As white foam; MS: 442.3 (M+H)$^+$.

50

Intermediate IVq (2S)-2-[[3-(3,4-Dichlorophenyl)-3-(4-methoxyphenyl)propanoyl]amino]-3-phenylpropanoic acid

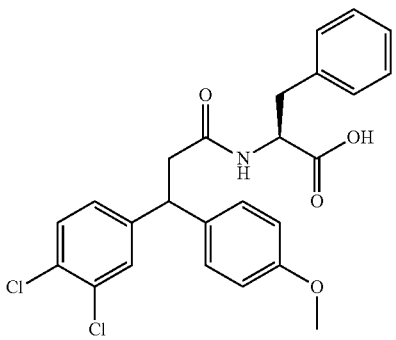 [SMILES: COc1ccc(C(CC(=O)N[C@@H](Cc2ccccc2)C(=O)O)c2ccc(Cl)c(Cl)c2)cc1]

As light yellow oil; MS: 472.2 (M+H)$^+$.

Intermediate IVr (2S)-2-[[(E)-3-(3,4-Dichlorophenyl)prop-2-enoyl]amino]-3-phenylpropanoic acid

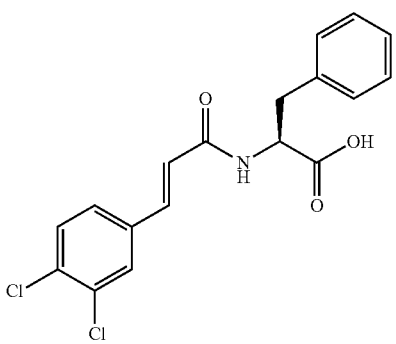 [SMILES: O=C(/C=C/c1ccc(Cl)c(Cl)c1)N[C@@H](Cc1ccccc1)C(=O)O]

As yellow foam; MS: 364.1 (M+H)$^+$.

Intermediate IVs (2S)-2-[[(E)-3-(3,5-Dichlorophenyl)prop-2-enoyl]amino]-3-phenylpropanoic Acid

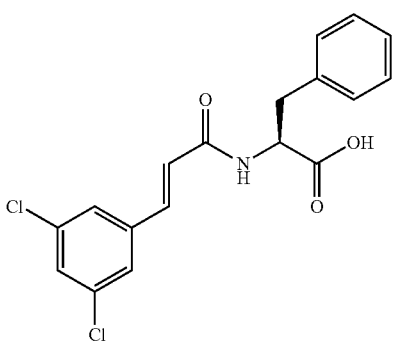 [SMILES: O=C(/C=C/c1cc(Cl)cc(Cl)c1)N[C@@H](Cc1ccccc1)C(=O)O]

As yellow oil; MS: 364.1 (M+H)$^+$.

Intermediate Va (2S)-2-[3-(3,4-Dichlorophenyl)propanoylamino]-3-(4-methoxyphenyl)propanoic acid

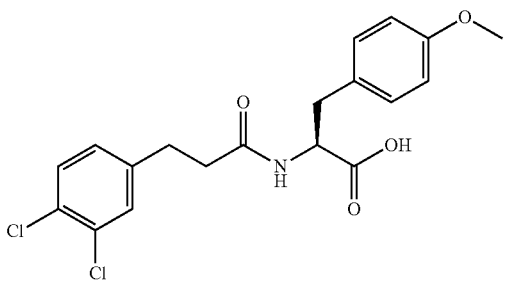 [SMILES: COc1ccc(C[C@H](NC(=O)CCc2ccc(Cl)c(Cl)c2)C(=O)O)cc1]

A] (2,5-Dioxopyrrolidin-1-yl) 3-(3,4-dichlorophenyl)propanoate

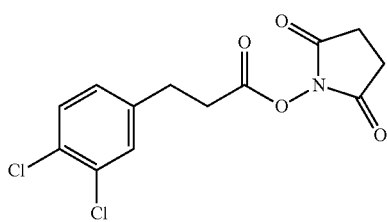 [SMILES: O=C(CCc1ccc(Cl)c(Cl)c1)ON1C(=O)CCC1=O]

In a 50 mL round-bottomed flask, 3-(3,4-dichlorophenyl) propanoic acid (704 mg, 3.21 mmol, Eq: 1) was combined with DCM (15 ml) to give a colorless solution; pyridine (763 mg, 780 µl, 9.64 mmol, Eq: 3), EDC (862 mg, 4.5 mmol, Eq: 1.4) and 1-hydroxypyrrolidine-2,5-dione (481 mg, 4.18 mmol, Eq: 1.3) were subsequently added at 0° C. and the reaction mixture was stirred overnight at RT, when LC-MS indicated the reaction to be complete.

The reaction mixture was quenched with $KHSO_4$ and extracted with DCM (2×). The organic layers were combined, washed with sat $NaHCO_3$, brine, dried over $Na_2SO_4$, and concentrated in vacuo. The crude material was purified by flash chromatography (silica gel, 70 g, 10% to 50% EtOAc in heptane) to afford 957 mg of the title compound as white solid; MS: 217.1 (M-succinimidyl)⁻.

B] (2,5-Dioxopyrrolidin-1-yl) 3-(3,4-dichlorophenyl)propanoate

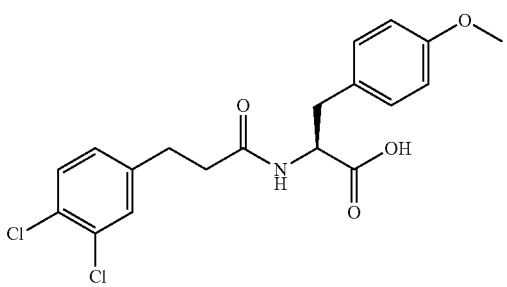 [SMILES: COc1ccc(C[C@H](NC(=O)CCc2ccc(Cl)c(Cl)c2)C(=O)O)cc1]

In a 10 mL round-bottomed flask, (S)-2-amino-3-(4-methoxyphenyl)propanoic acid (74.1 mg, 380 µmol, Eq: 1) was combined with THF (1 ml) to give a white suspension; the above prepared 2,5-dioxopyrrolidin-1-yl 3-(3,4-dichlorophenyl)propanoate (120 mg, 380 µmol, Eq: 1) in DME (2 ml) and $NaHCO_3$ (31.9 mg, 14.8 µl, 380 µmol, Eq: 1) in water (2 ml) were added, and the heterogeneous mixture was vigorously stirred. LC-MS after 5 hours showed the reaction to be complete.

The mixture was poured into $KHSO_4$ and extracted with EtOAc (2×). The organic layers were combined, washed with brine, dried over $Na_2SO_4$, and concentrated in vacuo. The crude material was purified by flash chromatography (silica gel, 20 g, 1% to 10% MeOH in DCM) to yield 107 mg of the title product as off-white solid; MS: 396.1 (M+H)⁺.

In close analogy, using the appropriate, commercially available reagents and the necessary intermediates I or II, were prepared:

Intermediate Vb (2S)-2-[[2-(3,5-Dichlorophenoxy)acetyl]amino]-2-(4-fluorophenyl)acetic acid

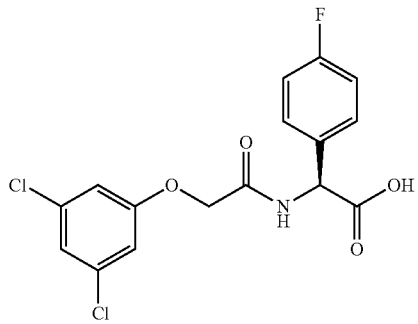 [SMILES: O=C(COc1cc(Cl)cc(Cl)c1)N[C@H](C(=O)O)c1ccc(F)cc1]

As white solid; MS: 370.1 (M–H).

Intermediate Vc (2S)-2-[3-(3,4-Dichlorophenyl)propanoylamino]-2-phenylacetic Acid

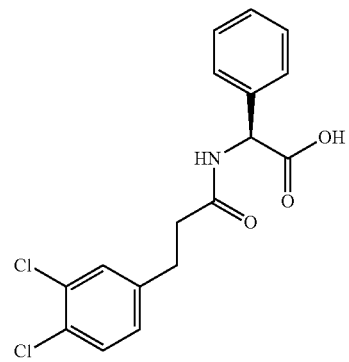 [SMILES: O=C(CCc1ccc(Cl)c(Cl)c1)N[C@H](C(=O)O)c1ccccc1]

As white solid; MS: 352.0 (M+H)⁺.

Intermediate Vd (2S)-2-[[3-(3,4-Dichlorophenyl)-3-phenylpropanoyl]amino]-2-phenylacetic acid

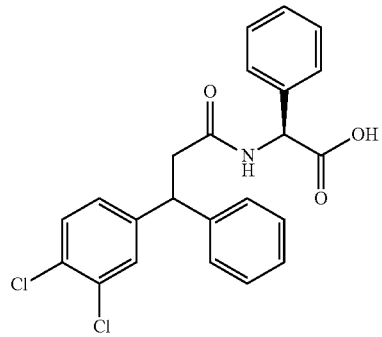 [SMILES: O=C(CC(c1ccccc1)c1ccc(Cl)c(Cl)c1)N[C@H](C(=O)O)c1ccccc1]

As white foam; MS: 428.1 (M+H)+.

Intermediate Ve (2S)-2-(4-Chlorophenyl)-2-[[2-(3,5-dichlorophenoxy)acetyl]amino]acetic Acid

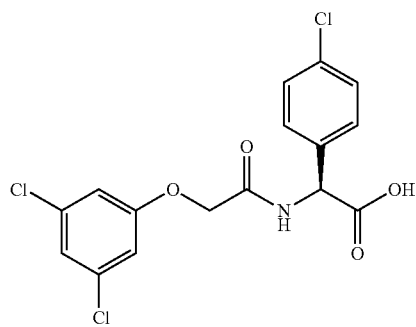 [SMILES: O=C(COc1cc(Cl)cc(Cl)c1)N[C@H](C(=O)O)c1ccc(Cl)cc1]

As white solid; MS: 388.0 (M+H)+.

Intermediate Vf (2S)-2-(4-Chlorophenyl)-2-[[3-(3,4-dichlorophenyl)-3-phenylpropanoyl]amino]acetic acid

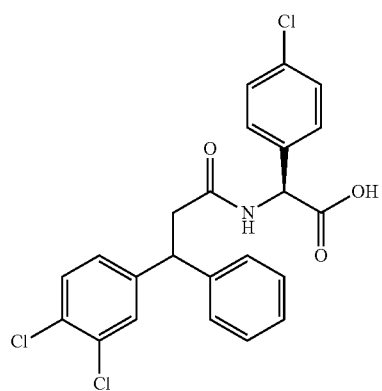 [SMILES: O=C(CC(c1ccccc1)c1ccc(Cl)c(Cl)c1)N[C@H](C(=O)O)c1ccc(Cl)cc1]

As white foam; MS: 462.0 (M+H)+.

Intermediate Vg (2S)-2-[[3-(3,5-dichlorophenyl)-3-(4-methoxyphenyl)propanoyl]amino]-3-phenylpropanoic acid

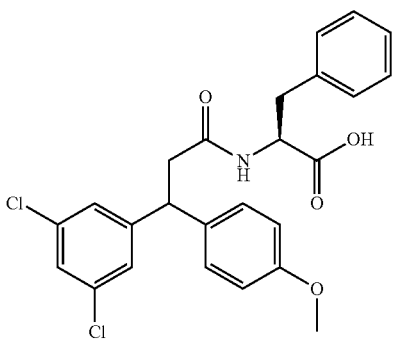 [SMILES: COc1ccc(C(CC(=O)N[C@@H](Cc2ccccc2)C(=O)O)c2cc(Cl)cc(Cl)c2)cc1]

As white foam; MS: 472.2 (M+H)+.

Intermediate Vh (2S)-3-(4-chlorophenyl)-2-[[3-(3,4-dichlorophenyl)-3-phenylpropanoyl]amino]propanoic acid

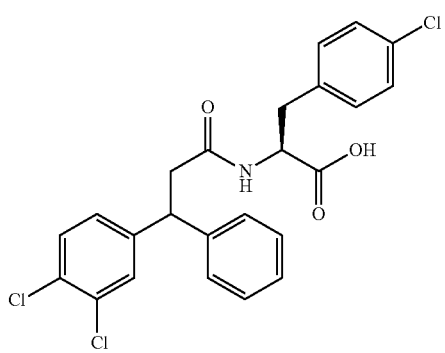 [SMILES: O=C(CC(c1ccccc1)c1ccc(Cl)c(Cl)c1)N[C@@H](Cc1ccc(Cl)cc1)C(=O)O]

As white foam; MS: 476.1 (M+H)+.

Intermediate Vi (2S)-2-[[3-(4-bromophenyl)-3-phenylpropanoyl]amino]-3-phenylpropanoic Acid

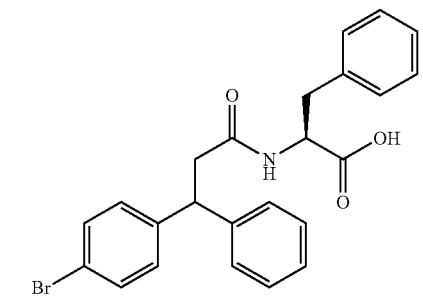 [SMILES: O=C(CC(c1ccccc1)c1ccc(Br)cc1)N[C@@H](Cc1ccccc1)C(=O)O]

As white foam; MS: 452.2 (M+H)+.

Intermediate Vj (2S)-2-[[3-(4-bromophenyl)-3-phenylpropanoyl]amino]-3-(4-chlorophenyl)propanoic acid

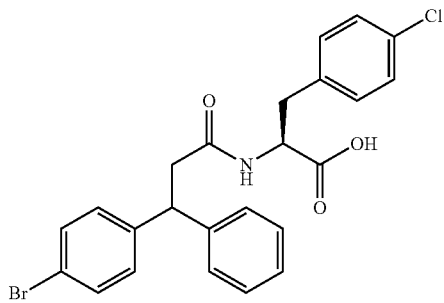 [SMILES: O=C(CC(c1ccccc1)c1ccc(Br)cc1)N[C@@H](Cc1ccc(Cl)cc1)C(=O)O]

As white foam; MS: 486.1 (M+H)+.

Intermediate Vk (2S)-2-[[3-(3,4-dichlorophenyl)-3-phenoxypropanoyl]amino]-3-phenylpropanoic Acid

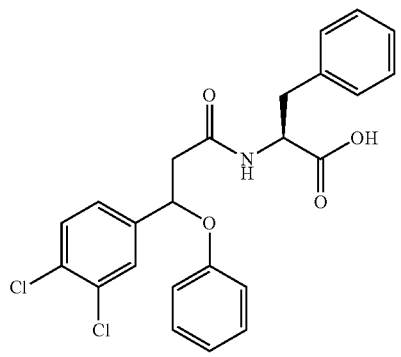 [SMILES: O=C(CC(Oc1ccccc1)c1ccc(Cl)c(Cl)c1)N[C@@H](Cc1ccccc1)C(=O)O]

As white foam; MS: 458.0 (M+H)+.

Intermediate Vl (2S)-2-[[3-(4-chlorophenoxy)-3-(3,4-dichlorophenyl)propanoyl]amino]-3-phenylpropanoic acid

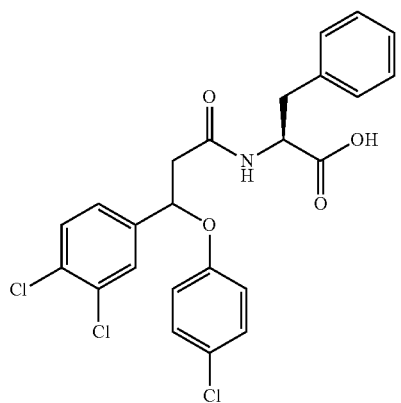 [SMILES: O=C(CC(Oc1ccc(Cl)cc1)c1ccc(Cl)c(Cl)c1)N[C@@H](Cc1ccccc1)C(=O)O]

As white foam; MS: 490.1 (M–H).

Intermediate Vm (2S)-2-(3,3-Diphenylpropanoylamino)-3-phenylpropanoic Acid

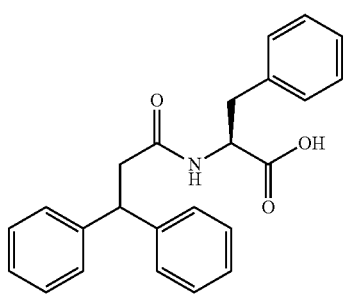 [SMILES: O=C(CC(c1ccccc1)c1ccccc1)N[C@@H](Cc1ccccc1)C(=O)O]

As white foam; MS: 374.2 (M+H)+.

Intermediate Vn (2S)-2-[[3-(3,4-Dichlorophenyl)-3-phenylpropanoyl]amino]-3-(4-methoxyphenyl)propanoic acid

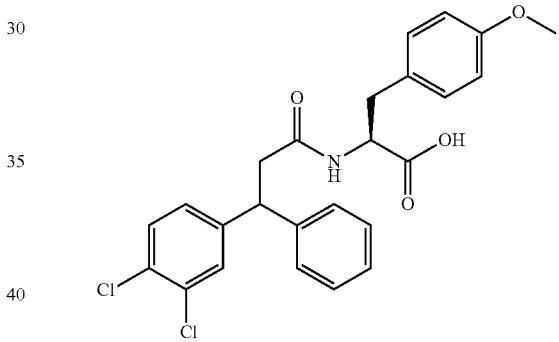

As white foam; MS: 472.2 (M+H)+.

Intermediate Vo (2S)-2-[[3-(3,5-Difluorophenyl)-3-(4-methoxyphenyl)propanoyl]amino]-3-phenylpropanoic acid

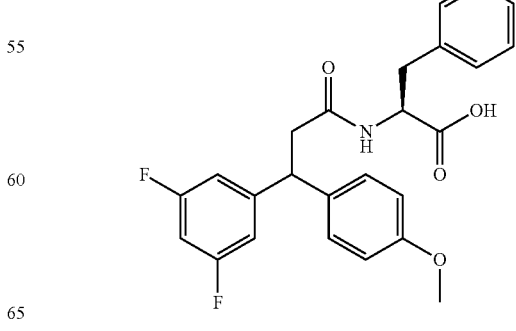

As white foam; MS: 440.2 (M+H)+.

Intermediate VIa (3R,4S)-4-[[(2S)-2-Amino-2-phenylacetyl]amino]-2,2-difluoro-3-hydroxy-5-methyl-N-(2,2,2-trifluoroethyl)hexanamide

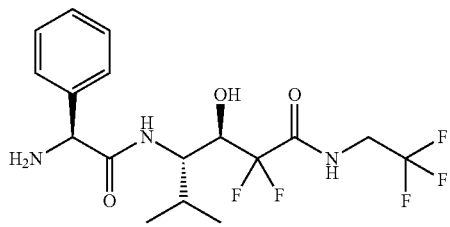 [SMILES: CC(C)[C@H](NC(=O)[C@@H](N)c1ccccc1)[C@@H](O)C(F)(F)C(=O)NCC(F)(F)F]

A] tert-Butyl N-[(1S)-2-[[(3S,4R)-5,5-difluoro-4-hydroxy-2-methyl-6-oxo-6-(2,2,2-trifluoroethylamino)hexan-3-yl]amino]-2-oxo-1-phenylethyl]carbamate

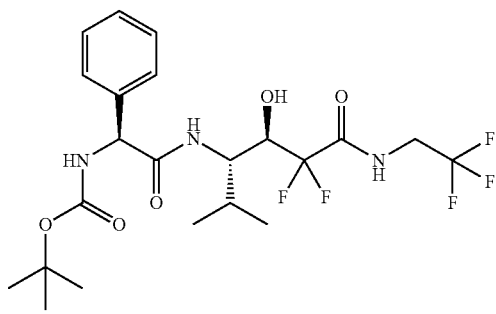 [SMILES: CC(C)[C@H](NC(=O)[C@@H](NC(=O)OC(C)(C)C)c1ccccc1)[C@@H](O)C(F)(F)C(=O)NCC(F)(F)F]

In a 25 ml flask, (4S)-4-amino-2,2-difluoro-3-hydroxy-5-methyl-N-(2,2,2-trifluoroethyl)hexanamide dihydrochloride [0.3M in DMF] (Intermediate Ma, 1.33 ml, 398 µmol, Eq: 1), (S)-2-((tert-butoxycarbonyl)amino)-2-phenylacetic acid (0.100 g, 398 µmol, Eq: 1) and HATU (166 mg, 438 µmol, Eq: 1.1) were mixed in DMF (4 ml). Hunig's base (257 mg, 348 µl, 1.99 mmol, Eq: 5) was then added, and the reaction mixture was stirred at RT for 2 h. It was diluted with EtOAc, poured into 1M KHSO₄, and the aqueous layer was extracted with EtOAc (2×20 ml). The combined organics layers were washed with NaHCO₃, brine, dried over Na₂SO₄, and evaporated. Purification by flash chromatography (silica gel, 20 g, 20% to 100% EtOAc in heptane) generated 124 mg of the title compound as yellow foam; MS: 512.2 (M+H)⁺.

B] (3R,4S)-4-[[(2S)-2-Amino-2-phenylacetyl]amino]-2,2-difluoro-3-hydroxy-5-methyl-N-(2,2,2-trifluoroethyl)hexanamide

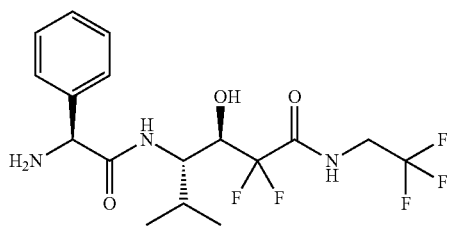 [SMILES: CC(C)[C@H](NC(=O)[C@@H](N)c1ccccc1)[C@@H](O)C(F)(F)C(=O)NCC(F)(F)F]

To a solution of the above prepared tert-butyl N-[(1S)-2-[[(3S,4R)-5,5-difluoro-4-hydroxy-2-methyl-6-oxo-6-(2,2,2-trifluoroethyl amino)hexan-3-yl]amino]-2-oxo-1-phenylethyl]carbamate (0.120 g, 235 µmol, Eq: 1) in MeOH (3 ml) was added HCl 4M in dioxane (293 µl, 1.17 mmol, Eq: 5); the reaction mixture was stirred at RT for 2 hours and at 40° C. for 2 hours. LC-MS indicated the reaction to be complete. The solvent was carefully evaporated to dryness to leave 119 mg of a light purple foam which was used directly for the next step; MS: 412.2 (M+H)⁺.

In close analogy were prepared:

Intermediate VIb (3R,4S)-4-[[(2S)-2-Amino-2-(4-chlorophenyl)acetyl]amino]-2,2-difluoro-3-hydroxy-5-methyl-N-(2,2,2-trifluoroethyl)hexanamide

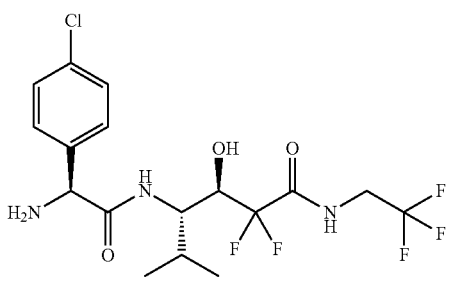 [SMILES: CC(C)[C@H](NC(=O)[C@@H](N)c1ccc(Cl)cc1)[C@@H](O)C(F)(F)C(=O)NCC(F)(F)F]

Using (2S)-2-(4-chlorophenyl)-2-[(2-methylpropan-2-yl)oxycarbonylamino]acetic acid instead of (S)-2-((tert-butoxycarbonyl)amino)-2-phenyl acetic acid as yellow oil; MS: 412.2 (M+H)⁺.

Intermediate VIc (3R,4S)-4-[[(2S)-2-amino-2-(4-methoxyphenyl)acetyl]amino]-2,2-difluoro-3-hydroxy-5-methyl-N-(2,2,2-trifluoroethyl)hexanamide

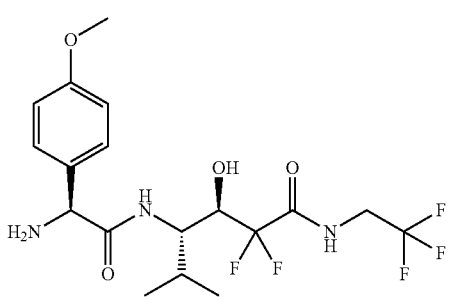 [SMILES: COc1ccc([C@H](N)C(=O)N[C@@H](C(C)C)[C@@H](O)C(F)(F)C(=O)NCC(F)(F)F)cc1]

Using (2S)-2-(4-methoxyphenyl)-2-[(2-methylpropan-2-yl)oxycarbonylamino]acetic acid instead of (S)-2-((tert-butoxycarbonyl)amino)-2-phenylacetic acid as yellow oil; MS: 442.2 (M+H)⁺.

Intermediate VId (3R,4S)-4-[[(2S)-2-amino-2-phenylacetyl]amino]-2,2-difluoro-3-hydroxy-5-methyl-N-(2-morpholin-4-ylethyl)hexanamide

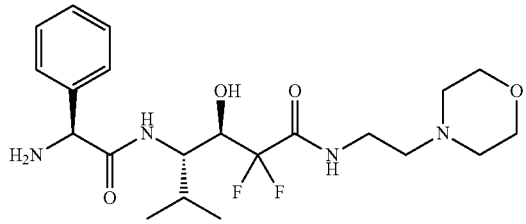 [SMILES: CC(C)[C@H](NC(=O)[C@@H](N)c1ccccc1)[C@@H](O)C(F)(F)C(=O)NCCN1CCOCC1]

Using (3R,4S)-4-amino-2,2-difluoro-3-hydroxy-5-methyl-N-(2-morpholin-4-ylethyl)hexanamide (Intermediate IIIc) instead of (4S)-4-amino-2,2-difluoro-3-hydroxy-5-methyl-N-(2,2,2-trifluoroethyl)hexanamide (Intermediate IIIa) as light yellow foam; MS: 443.3 $(M+H)^+$.

Intermediate VIe (3R,4S)-4-[[(2S)-2-amino-3-phenylpropanoyl]amino]-2,2-difluoro-3-hydroxy-5-methyl-N-(2,2,2-trifluoroethyl)hexanamide

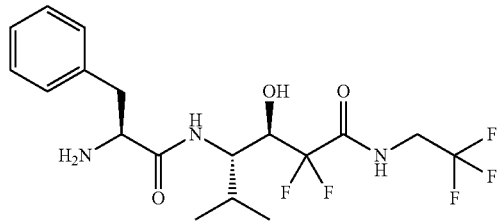 [SMILES: CC(C)[C@H](NC(=O)[C@@H](N)Cc1ccccc1)[C@@H](O)C(F)(F)C(=O)NCC(F)(F)F]

Using (2S)-2-[(2-methylpropan-2-yl)oxycarbonylamino]-3-phenylpropanoic acid instead of (S)-2-((tert-butoxycarbonyl)amino)-2-phenylacetic acid.

Intermediates (+)-VII and (−)-VII (2,5-Dioxopyrrolidin-1-yl) (3R)-3-(3,5-dichlorophenyl)-3-phenylpropanoate and (2,5-dioxopyrrolidin-1-yl) (3S)-3-(3,5-dichlorophenyl)-3-phenylpropanoate

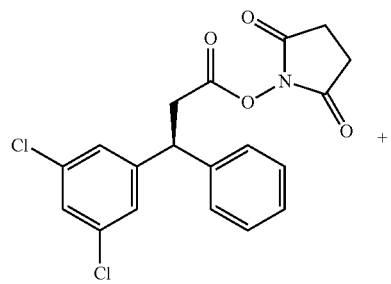

+

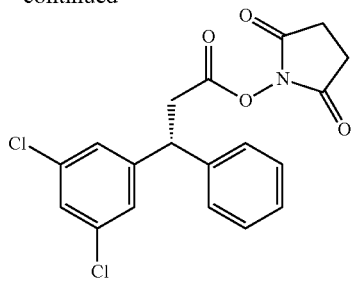

In a 25 mL flask, 3-(3,5-dichlorophenyl)-3-phenylpropanoic acid (572 mg, 1.94 mmol, Eq: 1; Intermediate Id) was combined with DCM (10 ml) to give a colorless solution. At 0° C., pyridine (460 mg, 470 μl, 5.81 mmol, Eq: 3), EDC (520 mg, 2.71 mmol, Eq: 1.4) and 1-hydroxypyrrolidine-2,5-dione (268 mg, 2.33 mmol, Eq: 1.2) were added, the ice-bath was removed, and the reaction allowed to proceed overnight at rt. The reaction mixture was quenched with 0.5M $KHSO_4$ sol. and extracted with DCM (2×20 mL). The organic layers were washed with sat $NaHCO_3$, then with $H_2O$/NaCl sol. The organic layers were combined, dried over $Na_2SO_4$ and concentrated in vacuo. The crude material was purified by flash chromatography (silica gel, 50 g, 10% to 70% EtOAc in heptane) to yield 566 mg of racemic title compound as white solid; MS: 295.1 $(M-Su)^-$.

468 mg thereof were separated into the two enantiomers by chromatography over a Reprosil chiral NR column with heptane/30% iPrOH as eluent, affording as first elution product 165 mg of (+)-(2,5-dioxopyrrolidin-1-yl)-3-(3,5-dichlorophenyl)-3-phenylpropanoate (intermediate (+)-VII) and as second elution product 185 mg of (−)-(2,5-dioxopyrrolidin-1-yl)-3-(3,5-dichlorophenyl)-3-phenylpropanoate (intermediate (−)-VII), respectively. Since both samples were contaminated with some free acid, they were once again purified by flash chromatography (silica gel, 20 g, 10% to 100% AcOEt in heptane) to yield 125 mg pure (+)-isomer and 122 mg pure (−)-isomer.

Example 1

(4S)-4-[[(2S)-2-[3-(3-Chlorophenyl)propanoylamino]-3-phenylpropanoyl]amino]-2,2-difluoro-5-methyl-N-(2-morpholin-4-ylethyl)-3-oxohexanamide

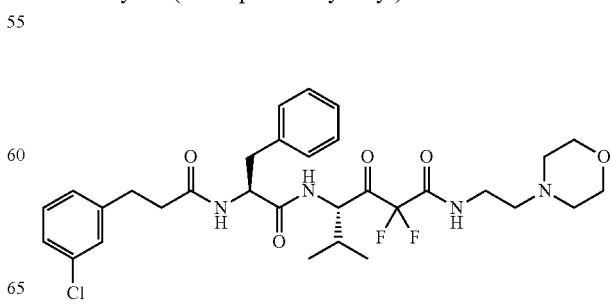

A] (3R,4S)-4-[[(2S)-2-[3-(3-chlorophenyl)propanoylamino]-3-phenylpropanoyl]amino]-2,2-difluoro-3-hydroxy-5-methyl-N-(2-morpholin-4-ylethyl)hexanamide

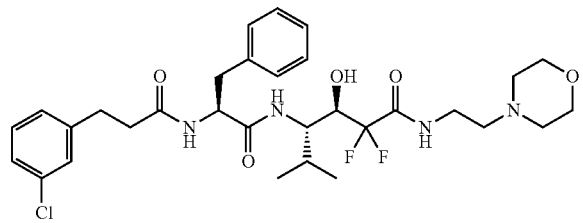 [SMILES: CC(C)[C@H](NC(=O)[C@H](Cc1ccccc1)NC(=O)CCc1cccc(Cl)c1)[C@@H](O)C(F)(F)C(=O)NCCN1CCOCC1]

In a 10 mL two-necked flask, (S)-2-(3-(3-chlorophenyl)propanamido)-3-phenylpropanoic acid (Intermediate IVa, 128 mg, 385 μmol, Eq: 1) was combined with DMF (3 ml) to give a colorless solution; 2-(1H-benzo[d][1,2,3]triazol-1-yl)-1,1,3,3-tetramethylisouronium tetrafluoroborate (148 mg, 461 μmol, Eq: 1.2) and Hunig's base (174 mg, 235 μl, 1.35 mmol, Eq: 3.5) were added and the reaction mixture stirred at RT for 30 min. Subsequently, (3R,4S)-4-amino-2,2-difluoro-3-hydroxy-5-methyl-N-(2-morpholinoethyl)hexanamide hydrochloride (Intermediate IIIc, calculated as dihydrochloride, since last traces of HCl couldn't be removed in spite of scrupulous drying, 0.147 g, 385 μmol, Eq: 1) was then added and the reaction was stirred at RT for 2 hours. LC-MS after 2 h showed the amidation to be complete. The reaction mixture was poured into 5 ml sat NH$_4$Cl and extracted with DCM (2×15 mL). The organic layers were combined, washed with brine, dried over Na$_2$SO$_4$ and concentrated in vacuo. Purification by flash chromatography (silica gel, 20 g, 5% to 10% MeOH in DCM) produced 205 mg of the desired title product as very light brown oil; MS: 623.5 (M+H)$^+$.

B] (4S)-4-[[(2S)-2-[3-(3-Chlorophenyl)propanoylamino]-3-phenylpropanoyl]amino]-2,2-difluoro-5-methyl-N-(2-morpholin-4-ylethyl)-3-oxohexanamide

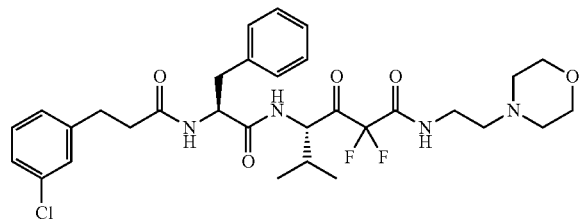 [SMILES: CC(C)[C@H](NC(=O)[C@H](Cc1ccccc1)NC(=O)CCc1cccc(Cl)c1)C(=O)C(F)(F)C(=O)NCCN1CCOCC1]

In a 10 mL two-necked flask, the above prepared (3R,4S)-4-((S)-2-(3-(3-chlorophenyl)propanamido)-3-phenylpropanamido)-2,2-difluoro-3-hydroxy-5-methyl-N-(2-morpholinoethyl)hexanamide (0.100 g, 160 μmol, Eq: 1) was combined with DCM (2 ml) to give a light yellow solution. Dess-Martin periodinane (499 mg, 366 μl, 177 μmol, Eq: 1.1) was added at 0° C. and the reaction mixture was stirred at RT for 5 hours. It was then poured into 5 ml sat NH$_4$Cl and extracted with DCM (2×10 mL). The organic layers were combined, washed with brine, dried over Na$_2$SO$_4$ and concentrated in vacuo. The crude material was purified by flash chromatography (silica gel, 10 g, 0% to 10% MeOH in DCM) to yield 51 mg of the title compound as light yellow oil; MS: 621.4 (M+H)$^+$.

Example 2

(4S)-4-[[(2S)-2-[[(E)-3-(3,5-Dichlorophenyl)prop-2-enoyl]amino]-2-phenylacetyl]amino]-2,2-difluoro-5-methyl-3-oxo-N-(2,2,2-trifluoroethyl)hexanamide

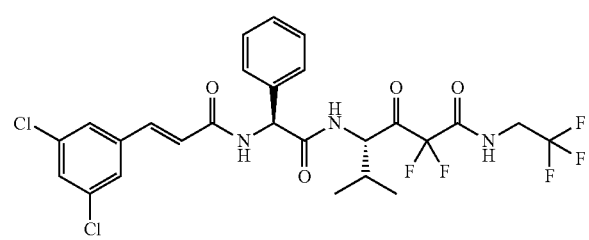 [SMILES: CC(C)[C@H](NC(=O)[C@@H](NC(=O)/C=C/c1cc(Cl)cc(Cl)c1)c1ccccc1)C(=O)C(F)(F)C(=O)NCC(F)(F)F]

A] (2,5-dioxopyrrolidin-1-yl) (E)-3-(3,5-dichlorophenyl)prop-2-enoate

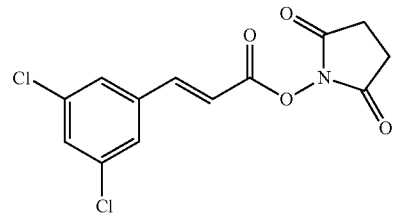 [SMILES: O=C(/C=C/c1cc(Cl)cc(Cl)c1)ON1C(=O)CCC1=O]

In a 100 mL pear-shaped flask, (E)-3-(3,5-dichlorophenyl)acrylic acid (1 g, 4.61 mmol, Eq: 1) was combined with DCM (30 ml) to give a white suspension; pyridine (1.09 g, 1.12 ml, 13.8 mmol, Eq: 3), EDC (1.24 g, 6.45 mmol, Eq: 1.4) and 1-hydroxypyrrolidine-2,5-dione (689 mg, 5.99 mmol, Eq: 1.3) were added at 0° C. The ice-bath was removed and the reaction mixture was stirred at RT overnight (light yellow solution), when TLC indicated the disappearance of the starting acid. The reaction mixture was quenched with 0.5M KHSO$_4$ sol and extracted with DCM (2×50 ml). The organic layers were washed with sat NaHCO$_3$ and with brine, dried over Na$_2$SO$_4$, and concentrated in vacuo. Trituration with tert-butyl methyl ether yielded 1.24 g of the title product as white solid.

B] (3R,4S)-4-[[(2S)-2-[[(E)-3-(3,5-Dichlorophenyl)prop-2-enoyl]amino]-2-phenylacetyl]amino]-2,2-difluoro-3-hydroxy-5-methyl-N-(2,2,2-trifluoroethyl)hexanamide

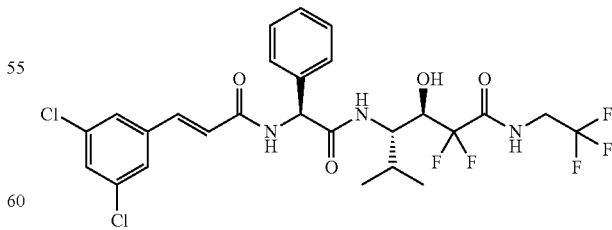

A solution of the above prepared (E)-2,5-dioxopyrrolidin-1-yl 3-(3,5-dichlorophenyl)acrylate (80.7 mg, 257 μmol, Eq: 1) in DME (4 ml) was added to a mixture of (3R,4S)-4-[[(2S)-2-Amino-2-phenylacetyl]amino]-2,2-difluoro-3-hydroxy-5-methyl-N-(2,2,2-trifluoroethyl)hexanamide (Intermediate VIa, 0.085 g, 139 μmol, 54.2% yield) in THF (2 ml)

and sodium bicarbonate (64.7 mg, 770 μmol, Eq: 3) in water (4 ml). The mixture (light purple solution) was vigorously stirred at RT overnight; Work up: The reaction mixture was poured into 1N KHSO₄ sol and extracted with AcOEt (2×). The organic layers were combined, washed with brine, dried over Na₂SO₄ and concentrated in vacuo; ensuing purification by flash chromatography (silica gel, 20 g, 20% to 100% EtOAc in heptane) yielded eventually 85 mg of the title compound as light purple solid; MS: 610.2 (M+H)⁺.

C] (4S)-4-[[(2S)-2-[[(E)-3-(3,5-Dichlorophenyl) prop-2-enoyl]amino]-2-phenylacetyl]amino]-2,2-difluoro-5-methyl-3-oxo-N-(2,2,2-trifluoroethyl) hexanamide

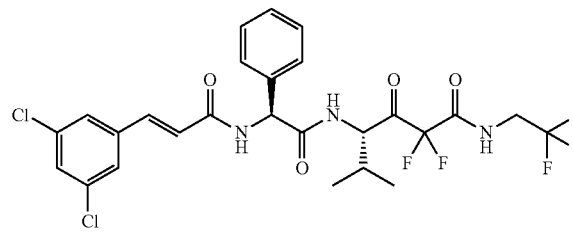

In a 10 mL round-bottomed flask, the above prepared (3R,4S)-4-[[(2S)-2-[[(E)-3-(3,5-dichlorophenyl)prop-2-enoyl]amino]-2-phenylacetyl]amino]-2,2-difluoro-3-hydroxy-5-methyl-N-(2,2,2-trifluoroethyl)hexanamide (0.080 g, 131 μmol, Eq: 1) was combined with DCM (3 ml) to give a colorless solution. Dess-Martin periodinane 15% in dichloromethane (556 mg, 408 μl, 197 μmol, Eq: 1.5) was added at 0° C. and the reaction mixture was stirred at RT. LC-MS after 2 h showed the reaction to be complete. The reaction mixture was treated with sat NaHCO₃ solution and extracted with EtOAc (2×20 mL). The organic layers were washed with brine, dried (Na₂SO₄) and evaporated. Purification of the crude material by flash chromatography (silica gel, 10 g, 30% EtOAc in heptane) generated 10 mg of the title compound as white solid; MS: 608.1 (M+H)⁺.

Examples of Table 1 were prepared by analogy to example 1.

TABLE 1

| Ex | Int. | Aspect | Structure and Name | [MH]⁺ |
|---|---|---|---|---|
| 3 | IIId, IVa | colorless oil | (4S)-4-[[(2S)-2-[3-(3-chlorophenyl)propanoylamino]-3-phenylpropanoyl]amino]-2,2-difluoro-5-methyl-3-oxo-N-(2-phenylethyl)hexanamide | 612.4 |
| 4 | IIIb, IVa | white solid | (4S)-4-[[(2S)-2-[3-(3-chlorophenyl)propanoylamino]-3-phenylpropanoyl]amino]-2,2-difluoro-5-methyl-3-oxo-N-(3,3,3-trifluoropropyl)hexanamide | 604.2 |

TABLE 1-continued

| Ex | Int. | Aspect | Structure and Name | [MH]+ |
|---|---|---|---|---|
| 5 | IIIa, IVe | white semisolid | [(4S)-4-[[(2S)-2-[3-(3,4-dichlorophenyl)propanoylamino]-3-phenylpropanoyl]amino]-2,2-difluoro-5-methyl-3-oxo-N-(2,2,2-trifluoroethyl)hexanamide | 624.3 |
| 6 | IIIa, IVc | white semisolid | (4S)-4-[[(2S)-2-[[2-(3-chlorophenoxy)acetyl]amino]-3-phenylpropanoyl]amino]-2,2-difluoro-5-methyl-3-oxo-N-(2,2,2-trifluoroethyl)hexanamide | 592.3 |
| 7 | IIIa, IVd | white semisolid | [(4S)-4-[[(2S)-2-[[2-(3,4-dichlorophenoxy)acetyl]amino]-3-phenylpropanoyl]amino]-2,2-difluoro-5-methyl-3-oxo-N-(2,2,2-trifluoroethyl)hexanamide | 626.2 |
| 8 | IIIa, IVb | white semisolid | (4S)-4-[[(2S)-2-[3-(3,5-dichlorophenyl)propanoylamino]-3-phenylpropanoyl]amino]-2,2-difluoro-5-methyl-3-oxo-N-(2,2,2-trifluoroethyl)hexanamide | 624.3 |

TABLE 1-continued

| Ex | Int. | Aspect | Structure and Name | [MH]+ |
|---|---|---|---|---|
| 9 | IIIa, IVm | white semisolid | | 626.2 |
| 10 | IIIa, IVa | white foam | (4S)-4-[[(2S)-2-[3-(3-chlorophenyl)propanoylamino]-3-phenylpropanoyl]amino]-2,2-difluoro-5-methyl-3-oxo-N-(2,2,2-trifluoroethyl)hexanamide | 590.3 |
| 11 | IIIc, IVd | white foam | (4S)-4-[[(2S)-2-[[2-(3,4-dichlorophenoxy)acetyl]amino]-3-phenylpropanoyl]amino]-2,2-difluoro-5-methyl-N-(2-morpholin-4-ylethyl)-3-oxohexanamide | 657.4 |
| 12 | IIIc, IVc | light yellow foam | (4S)-4-[[(2S)-2-[[2-(3-chlorophenoxy)acetyl]amino]-3-phenylpropanoyl]amino]-2,2-difluoro-5-methyl-N-(2-morpholin-4-ylethyl)-3-oxohexanamide | 623.4 |

TABLE 1-continued

| Ex | Int. | Aspect | Structure and Name | [MH]+ |
|---|---|---|---|---|
| 13 | IIIc, IVm | light yellow foam | 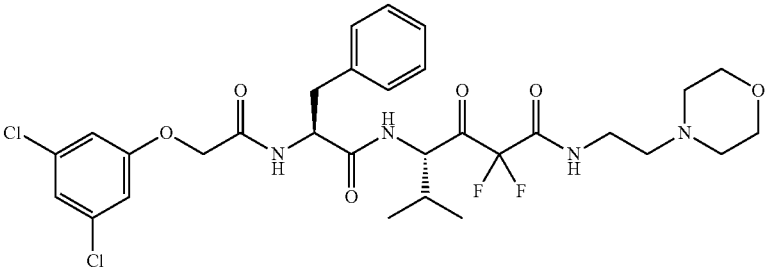 [SMILES: CC(C)[C@H](NC(=O)[C@H](Cc1ccccc1)NC(=O)COc1cc(Cl)cc(Cl)c1)C(=O)C(F)(F)C(=O)NCCN1CCOCC1]<br>(4S)-4-[[(2S)-2-[[2-(3,5-dichlorophenoxy)acetyl]amino]-3-phenylpropanoyl]amino]-2,2-difluoro-5-methyl-N-(2-morpholin-4-ylethyl)-3-oxohexanamide | 657.4 |
| 14 | IIIc, IVb | white foam | 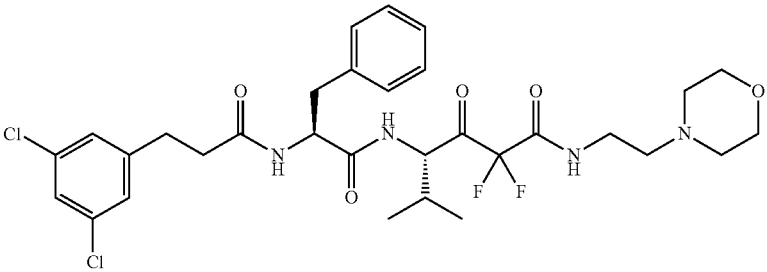 [SMILES: CC(C)[C@H](NC(=O)[C@H](Cc1ccccc1)NC(=O)CCc1cc(Cl)cc(Cl)c1)C(=O)C(F)(F)C(=O)NCCN1CCOCC1]<br>(4S)-4-[[(2S)-2-[3-(3,5-dichlorophenyl)propanoylamino]-3-phenylpropanoyl]amino]-2,2-difluoro-5-methyl-N-(2-morpholin-4-ylethyl)-3-oxohexanamide | 655.5 |
| 15 | IIIc, IVe | light yellow oil | 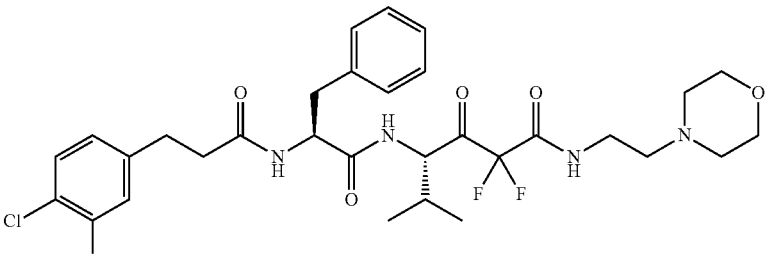<br>(4S)-4-[[(2S)-2-[3-(3,4-dichlorophenyl)propanoylamino]-3-phenylpropanoyl]amino]-2,2-difluoro-5-methyl-N-(2-morpholin-4-ylethyl)-3-oxohexanamide | 655.4 |
| 16 | IIId, IVe | colorless solid | 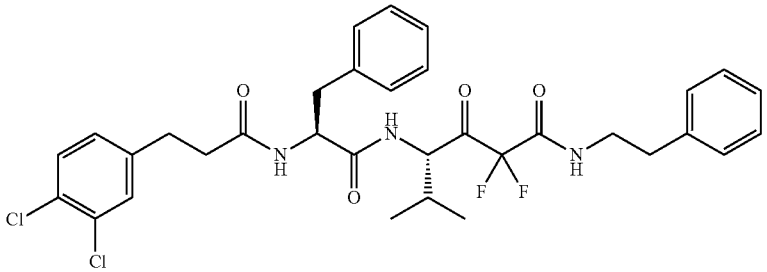 [SMILES: CC(C)[C@H](NC(=O)[C@H](Cc1ccccc1)NC(=O)CCc1ccc(Cl)c(Cl)c1)C(=O)C(F)(F)C(=O)NCCc1ccccc1]<br>(4S)-4-[[(2S)-2-[3-(3,4-dichlorophenyl)propanoylamino]-3-phenylpropanoyl]amino]-2,2-difluoro-5-methyl-3-oxo-N-(2-phenylethyl)hexanamide | 646.4 |

TABLE 1-continued

| Ex | Int. | Aspect | Structure and Name | [MH]+ |
|---|---|---|---|---|
| 17 | IIId, IVc | white solid | (4S)-4-[[(2S)-2-[[2-(3-chlorophenoxy)acetyl]amino]-3-phenylpropanoyl]amino]-2,2-difluoro-5-methyl-3-oxo-N-(2-phenylethyl)hexanamide | 614.3 |
| 18 | IIIb, IVe | white solid | (4S)-4-[[(2S)-2-[3-(3,4-dichlorophenyl)propanoylamino]-3-phenylpropanoyl]amino]-2,2-difluoro-5-methyl-3-oxo-N-(3,3,3-trifluoropropyl)hexanamide | 638.3 |
| 19 | IIIb, IVm | white foam | (4S)-4-[[(2S)-2-[[2-(3,5-dichlorophenoxy)acetyl]amino]-3-phenylpropanoyl]amino]-2,2-difluoro-5-methyl-3-oxo-N-(3,3,3-trifluoropropyl)hexanamide | 640.2 |
| 20 | IIIb, IVc | white solid | (4S)-4-[[(2S)-2-[[2-(3-chlorophenoxy)acetyl]amino]-3-phenylpropanoyl]amino]-2,2-difluoro-5-methyl-3-oxo-N-(3,3,3-trifluoropropyl)hexanamide | 606.3 |

TABLE 1-continued

| Ex | Int. | Aspect | Structure and Name | [MH]+ |
|---|---|---|---|---|
| 21 | IIIb, IVb | white foam | (4S)-4-[[(2S)-2-[3-(3,5-dichlorophenyl)propanoylamino]-3-phenylpropanoyl]amino]-2,2-difluoro-5-methyl-3-oxo-N-(3,3,3-trifluoropropyl)hexanamide | 638.3 |
| 22 | IIIb, IVd | light yellow foam | (4S)-4-[[(2S)-2-[[2-(3,4-dichlorophenoxy)acetyl]amino]-3-phenylpropanoyl]amino]-2,2-difluoro-5-methyl-3-oxo-N-(3,3,3-trifluoropropyl)hexanamide | 640.3 |
| 23 | IIId, IVf | white foam | (4S)-4-[[(2S)-3-(4-chlorophenyl)-2-[3-(3,4-dichlorophenyl)propanoylamino]propanoyl]amino]-2,2-difluoro-5-methyl-3-oxo-N-(2-phenylethyl)hexanamide | 680.4 |
| 24 | IIId, IVg | colorless foam | (4S)-4-[[(2S)-2-[3-(3,4-dichlorophenyl)propanoylamino]-3-(3,4-dimethoxyphenyl)propanoyl]amino]-2,2-difluoro-5-methyl-3-oxo-N-(2-phenylethyl)hexanamide | 706.5 |

TABLE 1-continued

| Ex | Int. | Aspect | Structure and Name | [MH]+ |
|---|---|---|---|---|
| 25 | IIIa, IVg | colorless oil | 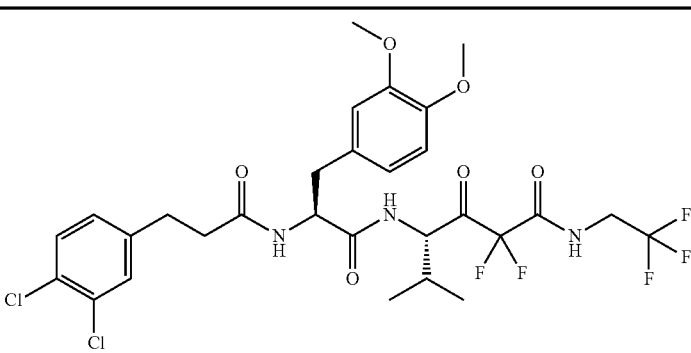<br>(4S)-4-[[(2S)-2-[3-(3,4-dichlorophenyl)propanoylamino]-3-(3,4-dimethoxyphenyl)propanoyl]amino]-2,2-difluoro-5-methyl-3-oxo-N-(2,2,2-trifluoroethyl)hexanamide | 684.3 |
| 26 | IIId, IVh | white foam | 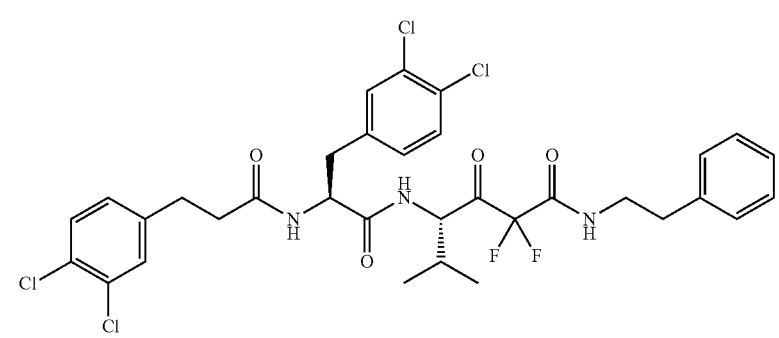 [SMILES: CC(C)[C@H](NC(=O)[C@H](Cc1ccc(Cl)c(Cl)c1)NC(=O)CCc1ccc(Cl)c(Cl)c1)C(=O)C(F)(F)C(=O)NCCc1ccccc1]<br>(4S)-4-[[(2S)-3-(3,4-dichlorophenyl)-2-[3-(3,4-dichlorophenyl)propanoylamino]propanoyl]amino]-2,2-difluoro-5-methyl-3-oxo-N-(2-phenylethyl)hexanamide | 714.4 |
| 27 | IIIa, IVj | white foam | 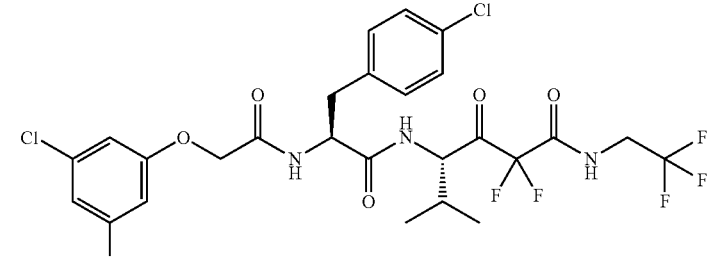<br>(4S)-4-[[(2S)-3-(4-chlorophenyl)-2-[[3-(3,5-dichlorophenoxy)acetyl]amino]propanoyl]amino]-2,2-difluoro-5-methyl-3-oxo-N-(2,2,2-trifluoroethyl)hexanamide | 660.3 |
| 28 | IIIa, IVi | white solid | 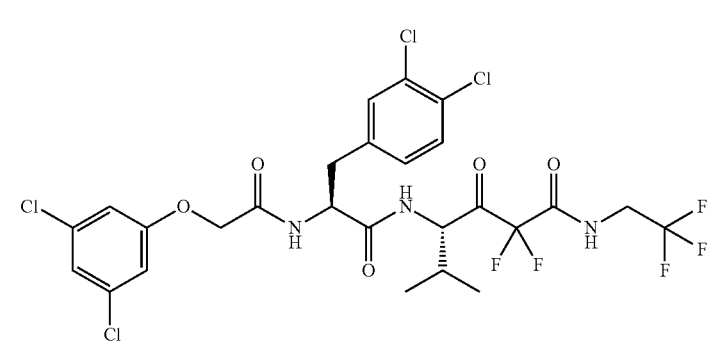<br>(4S)-4-[[(2S)-2-[[2-(3,5-dichlorophenoxy)acetyl]amino]-3-(3,4-dichlorophenyl)propanoyl]amino]-2,2-difluoro-5-methyl-3-oxo-N-(2,2,2-trifluoroethyl)hexanamide | 694.3 |

TABLE 1-continued

| Ex | Int. | Aspect | Structure and Name | [MH]+ |
|---|---|---|---|---|
| 29 | IIIe, IVm | white solid | 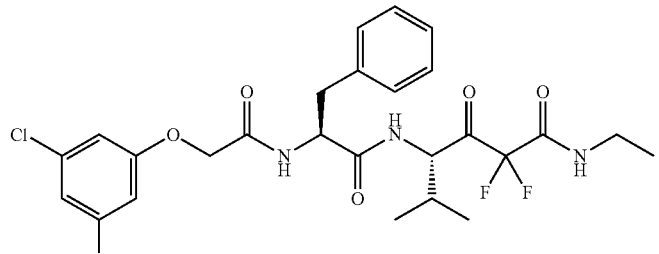<br>(4S)-4-[[(2S)-2-[[2-(3,5-dichlorophenoxy)acetyl]amino]-3-phenylpropanoyl]amino]-N-ethyl-2,2-difluoro-5-methyl-3-oxohexanamide | 572.3 |
| 30 | IIIg, IVm | light yellow solid | 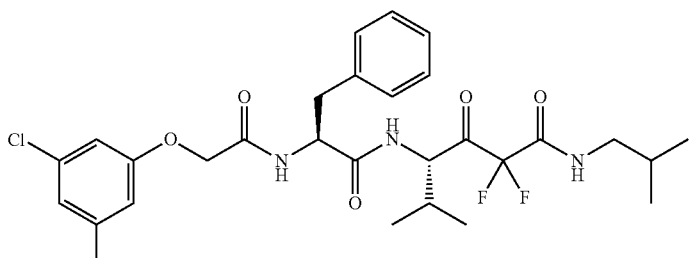<br>(4S)-4-[[(2S)-2-[[2-(3,5-dichlorophenoxy)acetyl]amino]-3-phenylpropanoyl]amino]-2,2-difluoro-5-methyl-N-(2-methylpropyl)-3-oxohexanamide | 600.3 |
| 31 | IIIe, IVi | white solid | 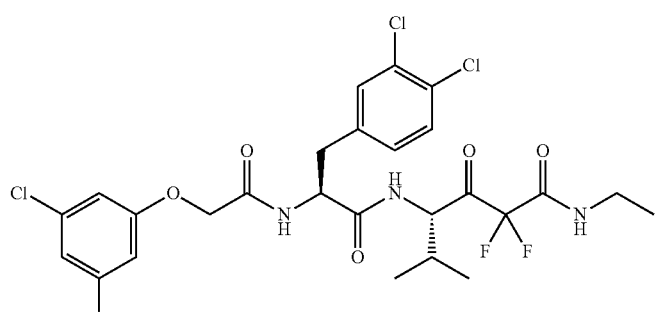<br>(4S)-4-[[(2S)-2-[[2-(3,5-dichlorophenoxy)acetyl]amino]-3-(3,4-dichlorophenyl)propanoyl]amino]-N-ethyl-2,2-difluoro-5-methyl-3-oxohexanamide | 640.2 |
| 32 | IIIg, IVi | white foam | 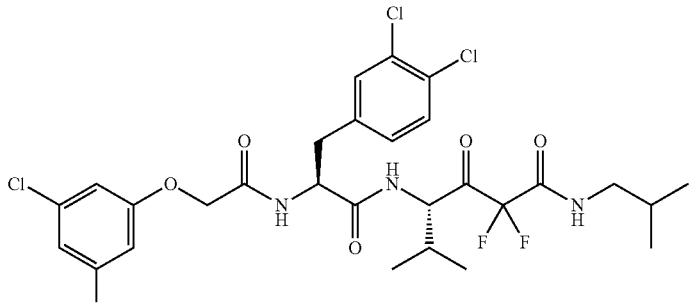<br>(4S)-4-[[(2S)-2-[[2-(3,5-dichlorophenoxy)acetyl]amino]-3-(3,4-dichlorophenyl)propanoyl]amino]-2,2-difluoro-5-methyl-N-(2-methylpropyl)-3-oxohexanamide | 668.3 |

TABLE 1-continued

| Ex | Int. | Aspect | Structure and Name | [MH]+ |
|---|---|---|---|---|
| 33 | IIIg, IVk | white foam | (4S)-4-[[(2S)-2-[[2-(3,5-dichlorophenoxy)acetyl]amino]-3-(3,4-difluorophenyl)propanoyl]amino]-2,2-difluoro-5-methyl-N-(2-methylpropyl)-3-oxohexanamide | 636.2 |
| 34 | IIIb, IVj | white semisolid | (4S)-4-[[(2S)-3-(4-chlorophenyl)-2-[[2-(3,5-dichlorophenoxy)acetyl]amino]propanoyamino]-2,2-difluoro-5-methyl-3-oxo-N-(3,3,3-trifluoropropyl)hexanamide | 674.3 |
| 35 | IIIb, IVi | white semisolid | (4S)-4-[[(2S)-2-[[2-(3,5-dichlorophenoxy)acetyl]amino]-3-(3,4-dichlorophenyl)propanoyl]amino]-2,2-difluoro-5-methyl-3-oxo-N-(3,3,3-trifluoropropyl)hexanamide | 708.2 |
| 36 | IIIb, IVk | white semisolid | (4S)-4-[[(2S)-2-[[2-(3,5-dichlorophenoxy)acetyl]amino]-3-(3,4-difluorophenyl)propanoyl]amino]-2,2-difluoro-5-methyl-3-oxo-N-(3,3,3-trifluoropropyl)hexanamide | 676.3 |

TABLE 1-continued

| Ex | Int. | Aspect | Structure and Name | [MH]+ |
|----|------|--------|--------------------|-------|
| 37 | IIIb, IVl | white semisolid | 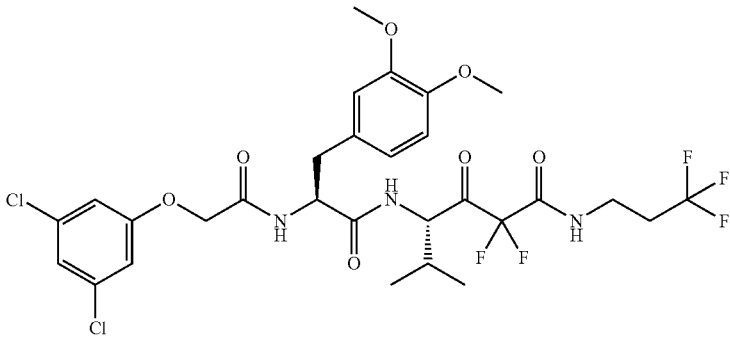 [SMILES: COc1ccc(C[C@H](NC(=O)COc2cc(Cl)cc(Cl)c2)C(=O)N[C@H](C(=O)C(F)(F)C(=O)NCCC(F)(F)F)C(C)C)cc1OC]<br>(4S)-4-[[(2S)-2-[[2-(3,5-dichlorophenoxy)acetyl]amino]-3-(3,4-dimethoxyphenyl)propanoyl]amino]-2,2-difluoro-5-methyl-3-oxo-N-(3,3,3-trifluoropropyl)hexanamide | 700.3 |
| 38 | IIIf, IVm | white solid | 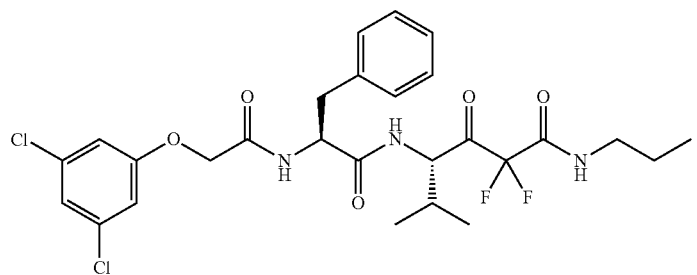 [SMILES: CCCNC(=O)C(F)(F)C(=O)[C@@H](NC(=O)[C@H](Cc1ccccc1)NC(=O)COc1cc(Cl)cc(Cl)c1)C(C)C]<br>(4S)-4-[[(2S)-2-[[2-(3,5-dichlorophenoxy)acetyl]amino]-3-phenylpropanoyl]amino]-2,2-difluoro-5-methyl-3-oxo-N-propylhexanamide | 586.3 |
| 39 | IIIh, IVm | colorless oil | 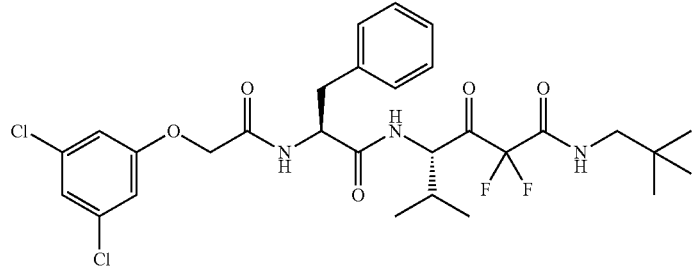 [SMILES: CC(C)[C@H](NC(=O)[C@H](Cc1ccccc1)NC(=O)COc1cc(Cl)cc(Cl)c1)C(=O)C(F)(F)C(=O)NCC(C)(C)C]<br>(4S)-4-[[(2S)-2-[[2-(3,5-dichlorophenoxy)acetyl]amino]-3-phenylpropanoyl]amino]-N-(2,2-dimethylpropyl)-2,2-difluoro-5-methyl-3-oxohexanamide | 614.3 |
| 40 | IIIa, IVp | white foam | 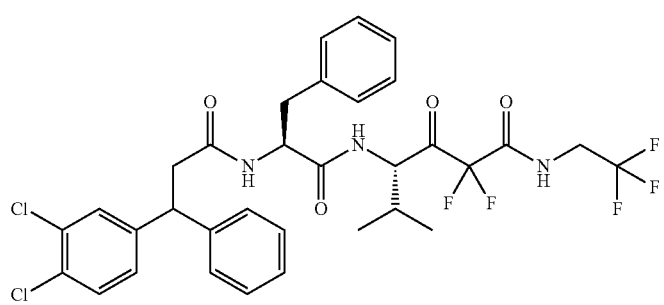 [SMILES: CC(C)[C@H](NC(=O)[C@H](Cc1ccccc1)NC(=O)CC(c1ccccc1)c1ccc(Cl)c(Cl)c1)C(=O)C(F)(F)C(=O)NCC(F)(F)F]<br>(4S)-4-[[(2S)-2-[[3-(3,4-dichlorophenyl)-3-phenylpropanoyl]amino]-3-phenylpropanoyl]amino]-2,2-difluoro-5-methyl-3-oxo-N-(2,2,2-trifluoroethyl)hexanamide | 700.3 |

TABLE 1-continued

| Ex | Int. | Aspect | Structure and Name | [MH]+ |
|---|---|---|---|---|
| 41 | IIIf, IVj | colorless oil | 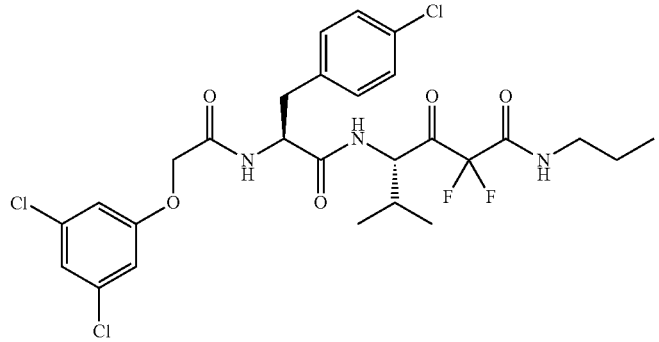 [SMILES: CCCNC(=O)C(F)(F)C(=O)[C@@H](NC(=O)[C@H](Cc1ccc(Cl)cc1)NC(=O)COc1cc(Cl)cc(Cl)c1)C(C)C]<br>(4S)-4-[[(2S)-3-(4-chlorophenyl)-2-[[2-(3,5-dichlorophenoxy)acetyl]amino]propanoyl]amino]-2,2-difluoro-5-methyl-3-oxo-N-propylhexanamide | 620.2 |
| 42 | IIIh, IVk | colorless oil | 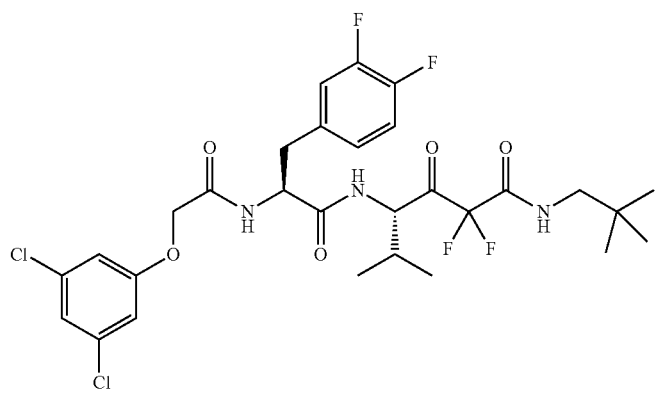 [SMILES: CC(C)[C@H](NC(=O)[C@H](Cc1ccc(F)c(F)c1)NC(=O)COc1cc(Cl)cc(Cl)c1)C(=O)C(F)(F)C(=O)NCC(C)(C)C]<br>(4S)-4-[[(2S)-2-[[2-(3,5-dichlorophenoxy)acetyl]amino]-3-(3,4-difluorophenyl)propanoyl]amino]-N-(2,2-dimethylpropyl)-2,2-difluoro-5-methyl-3-oxohexanamide | 650.3 |
| 43 | IIIa, IVk | off-white solid | 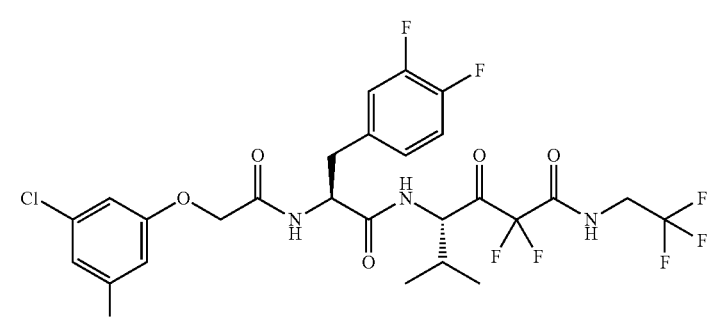<br>(4S)-4-[[(2S)-2-[[2-(3,5-dichlorophenoxy)acetyl]amino]-3-(3,4-difluorophenyl)propanoyl]amino]-2,2-difluoro-5-methyl-3-oxo-N-(2,2,2-trifluoroethyl)hexanamide | 660.3 |

TABLE 1-continued

| Ex | Int. | Aspect | Structure and Name | [MH]+ |
|---|---|---|---|---|
| 44 | IIIa, IVl | off-white solid | (4S)-4-[[(2S)-2-[[2-(3,5-dichlorophenoxy)acetyl]amino]-3-(3,4-dimethoxyphenyl)propanoyl]amino]-2,2-difluoro-5-methyl-3-oxo-N-(2,2,2-trifluoroethyl)hexanamide | 686.3 |
| 45 | IIIa, IVq | white semisolid | (4S)-4-[[(2S)-2-[[3-(3,4-dichlorophenyl)-3-(4-methoxyphenyl)propanoyl]amino]-3-phenylpropanoyl]amino]-2,2-difluoro-5-methyl-3-oxo-N-(2,2,2-trifluoroethyl)hexanamide | 730.3 |
| 46 | IIIf, IVr | colorless oil | (4S)-4-[[(2S)-2-[[(E)-3-(3,4-dichlorophenyl)prop-2-enoyl]amino]-3-phenylpropanoyl]amino]-2,2-difluoro-5-methyl-3-oxo-N-propylhexanamide | 582.2 |
| 47 | IIIh, IVr | colorless oil | (4S)-4-[[(2S)-2-[[(E)-3-(3,4-dichlorophenyl)prop-2-enoyl]amino]-3-phenylpropanoyl]amino]-N-(2,2-dimethylpropyl)-2,2-difluoro-5-methyl-3-oxohexanamide | 610.3 |

TABLE 1-continued

| Ex | Int. | Aspect | Structure and Name | [MH]+ |
|---|---|---|---|---|
| 48 | IIIa, IVr | colorless oil | 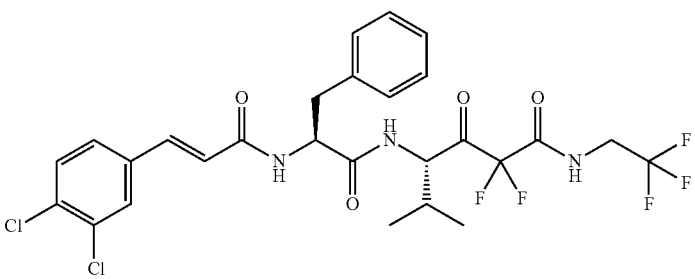 [SMILES: CC(C)[C@H](NC(=O)[C@H](Cc1ccccc1)NC(=O)/C=C/c1ccc(Cl)c(Cl)c1)C(=O)C(F)(F)C(=O)NCC(F)(F)F]<br>(4S)-4-[[(2S)-2-[[(E)-3-(3,4-dichlorophenyl)prop-2-enoyl]amino]-3-phenylpropanoyl]amino]-2,2-difluoro-5-methyl-3-oxo-N-(2,2,2-trifluoroethyl)hexanamide | 622.1 |
| 49 | IIIa, IVs | colorless oil | 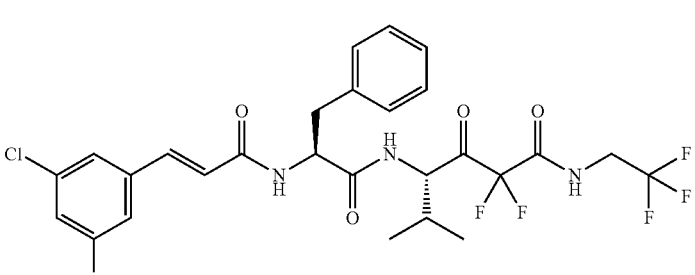<br>(4S)-4-[[(2S)-2-[[(E)-3-(3,5-dichlorophenyl)prop-2-enoyl]amino]-3-phenylpropanoyl]amino]-2,2-difluoro-5-methyl-3-oxo-N-(2,2,2-trifluoroethyl)hexanamide | 622.2 |
| 50 | IIIa, Ve | colorless oil | 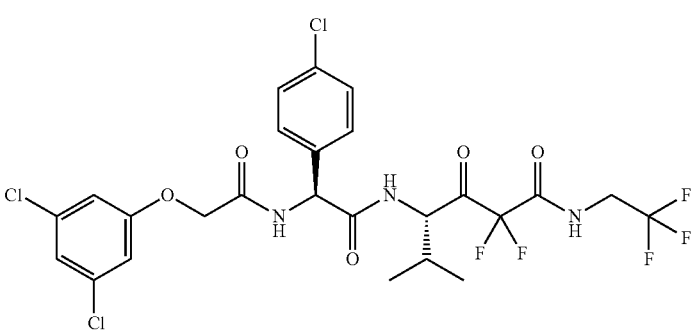 [SMILES: CC(C)[C@H](NC(=O)[C@@H](NC(=O)COc1cc(Cl)cc(Cl)c1)c1ccc(Cl)cc1)C(=O)C(F)(F)C(=O)NCC(F)(F)F]<br>(4S)-4-[[(2S)-2-(4-chlorophenyl)-2-[[2-(3,5-dichlorophenoxy)acetyl]amino]acetyl]amino]-2,2-difluoro-5-methyl-3-oxo-N-(2,2,2-trifluoroethyl)hexanamide | 646.2 |
| 51 | IIIa, Vm | white solid | 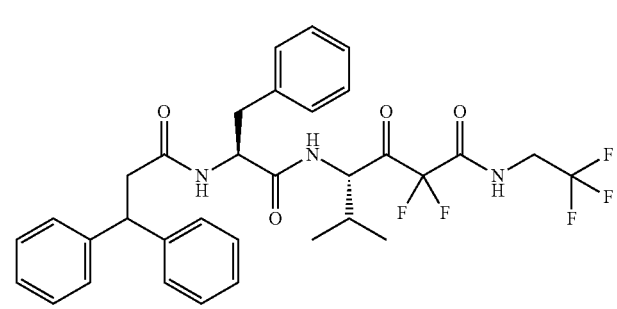 [SMILES: CC(C)[C@H](NC(=O)[C@H](Cc1ccccc1)NC(=O)CC(c1ccccc1)c1ccccc1)C(=O)C(F)(F)C(=O)NCC(F)(F)F]<br>(4S)-4-[[(2S)-2-(3,3-diphenylpropanoylamino)-3-phenylpropanoyl]amino]-2,2-difluoro-5-methyl-3-oxo-N-(2,2,2-trifluoroethyl)hexanamide | 632.3 |

TABLE 1-continued

| Ex | Int. | Aspect | Structure and Name | [MH]+ |
|---|---|---|---|---|
| 52 | IIIa, Vg | white foam | 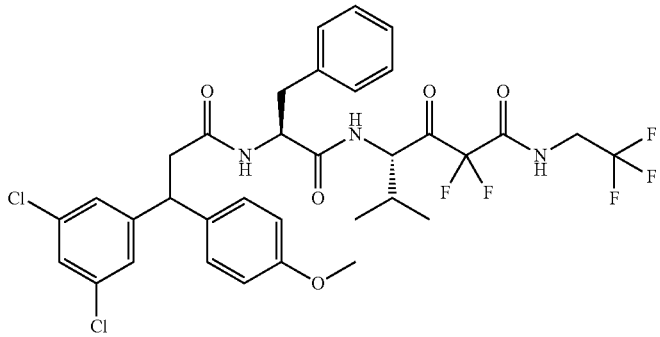 [SMILES: COc1ccc(C(CC(=O)N[C@@H](Cc2ccccc2)C(=O)N[C@H](C(=O)C(F)(F)C(=O)NCC(F)(F)F)C(C)C)c2cc(Cl)cc(Cl)c2)cc1]<br>(4S)-4-[[(2S)-2-[[3-(3,5-dichlorophenyl)-3-(4-methoxyphenyl)propanoyl]amino]-3-phenylpropanoyl]amino]-2,2-difluoro-5-methyl-3-oxo-N-(2,2,2-trifluoroethyl)hexanamide | 730.2 |
| 53 | IIIa, Vh | white solid | 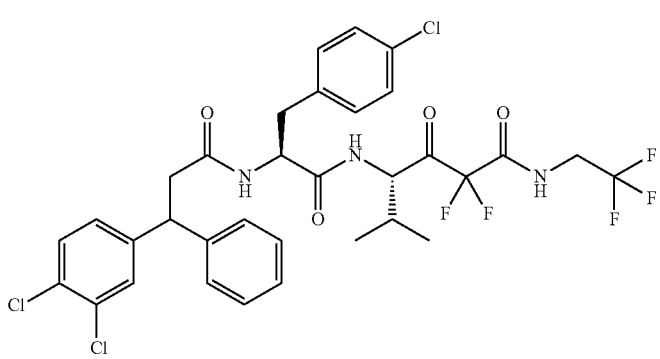<br>(4S)-4-[[(2S)-3-(4-chlorophenyl)-2-[[3-(3,4-dichlorophenyl)-3-phenylpropanoyl]amino]propanoyl]amino]-2,2-difluoro-5-methyl-3-oxo-N-(2,2,2-trifluoroethyl)hexanamide | 734.2 |
| 54 | IIIa, Vn | white solid | 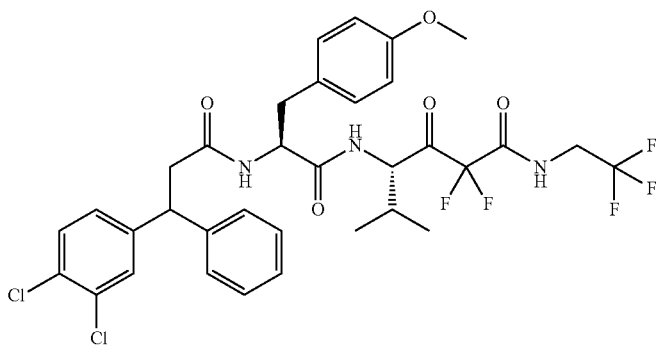 [SMILES: COc1ccc(C[C@H](NC(=O)CC(c2ccccc2)c2ccc(Cl)c(Cl)c2)C(=O)N[C@H](C(=O)C(F)(F)C(=O)NCC(F)(F)F)C(C)C)cc1]<br>(4S)-4-[[(2S)-2-[[3-(3,4-dichlorophenyl)-3-phenylpropanoyl]amino]-3-(4-methoxyphenyl)propanoyl]amino]-2,2-difluoro-5-methyl-3-oxo-N-(2,2,2-trifluoroethyl)hexanamide | 730.2 |

TABLE 1-continued

| Ex | Int. | Aspect | Structure and Name | [MH]+ |
|---|---|---|---|---|
| 55 | IIIa, IVn | white solid | 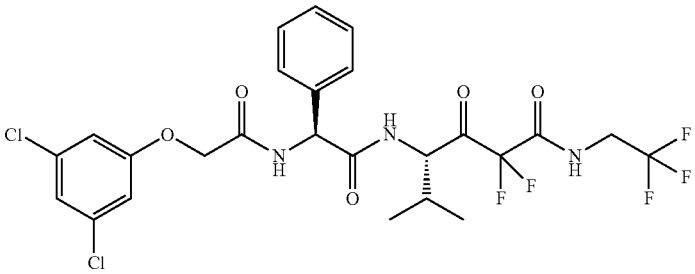 [SMILES: CC(C)[C@H](NC(=O)[C@@H](NC(=O)COc1cc(Cl)cc(Cl)c1)c1ccccc1)C(=O)C(F)(F)C(=O)NCC(F)(F)F](4S)-4-[[(2S)-2-[[2-(3,5-dichlorophenoxy)acetyl]amino]-2-phenylacetyl]amino]-2,2-difluoro-5-methyl-3-oxo-N-(2,2,2-trifluoroethyl)hexanamide | 612.1 |
| 56 | IIIa, Vb | colorless oil | 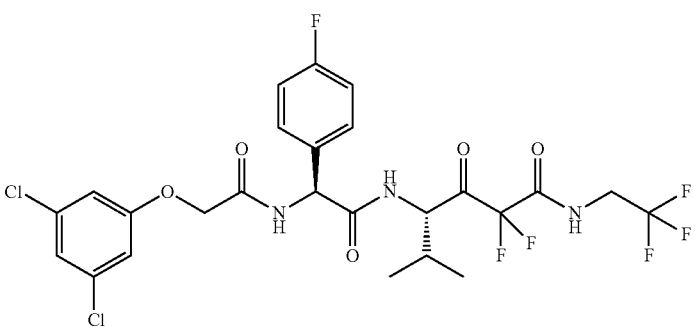 [SMILES: CC(C)[C@H](NC(=O)[C@@H](NC(=O)COc1cc(Cl)cc(Cl)c1)c1ccc(F)cc1)C(=O)C(F)(F)C(=O)NCC(F)(F)F](4S)-4-[[(2S)-2-[[2-(3,5-dichlorophenoxy)acetyl]amino]-2-(4-fluorophenyl)acetyl]amino]-2,2-difluoro-5-methyl-3-oxo-N-(2,2,2-trifluoroethyl)hexanamide | 630.1 |
| 57 | IIa, Vd | white semisolid | 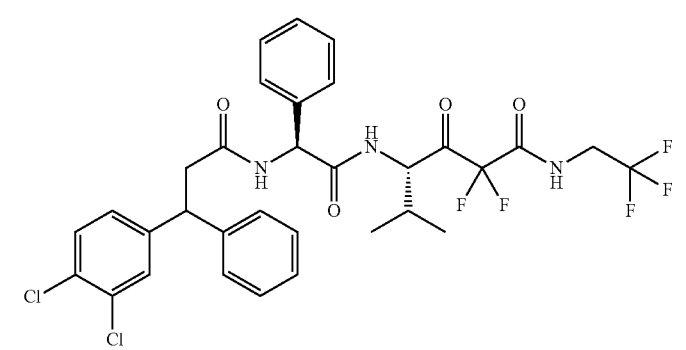 [SMILES: CC(C)[C@H](NC(=O)[C@@H](NC(=O)CC(c1ccccc1)c1ccc(Cl)c(Cl)c1)c1ccccc1)C(=O)C(F)(F)C(=O)NCC(F)(F)F](4S)-4-[[(2S)-2-[[3-(3,4-dichlorophenyl)-3-phenylpropanoyl]amino]-2-phenylacetyl]amino]-2,2-difluoro-5-methyl-3-oxo-N-(2,2,2-trifluoroethyl)hexanamide | 686.2 |

TABLE 1-continued

| Ex | Int. | Aspect | Structure and Name | [MH]⁺ |
|----|------|--------|--------------------|-------|
| 58 | IIIa, Vf | white semisolid | (4S)-4-[[(2S)-2-(4-chlorophenyl)-2-[[3-(3,4-dichlorophenyl)-3-phenylpropanoyl]amino]acetyl]amino]-2,2-difluoro-5-methyl-3-oxo-N-(2,2,2-trifluoroethyl)hexanamide | 720.2 |
| 59 | IIIa, Vc | white semisolid | (4S)-4-[[(2S)-2-[3-(3,4-dichlorophenyl)propanoylamino]-2-phenylacetyl]amino]-2,2-difluoro-5-methyl-3-oxo-N-(2,2,2-trifluoroethyl)hexanamide | 610.1 |
| 60 | IIIa, Vi | white solid | (4S)-4-[[(2S)-2-[[3-(4-bromophenyl)-3-phenylpropanoyl]amino]-3-phenylpropanoyl]amino]-2,2-difluoro-5-methyl-3-oxo-N-(2,2,2-trifluoroethyl)hexanamide | 710.2 |

TABLE 1-continued

| Ex | Int. | Aspect | Structure and Name | [MH]+ |
|---|---|---|---|---|
| 61 | IIIa, Vj | white solid | (4S)-4-[[(2S)-2-[[3-(4-bromophenyl)-3-phenylpropanoyl]amino]-3-(4-chlorophenyl)propanoyl]amino]-2,2-difluoro-5-methyl-3-oxo-N-(2,2,2-trifluoroethyl)hexanamide | 744.2 |
| 71 | IIIa, Vk | white foam | (4S)-4-[[(2S)-2-[[3-(3,4-dichlorophenyl)-3-phenoxypropanoyl]amino]-3-phenylpropanoyl]amino]-2,2-difluoro-5-methyl-3-oxo-N-(2,2,2-trifluoroethyl)hexanamide | 716.2 |
| 73 | IIIa, Vl | white foam | (4S)-4-[[(2S)-2-[[3-(4-chlorophenoxy)-3-(3,4-dichlorophenyl)propanoyl]amino]-3-phenylpropanoyl]amino]-2,2-difluoro-5-methyl-3-oxo-N-(2,2,2-trifluoroethyl)hexanamide | 750.1 |
| 76 | IIIa, Vo | white foam | (4S)-4-[[(2S)-2-[[3-(3,5-difluorophenyl)-3-(4-methoxyphenyl)propanoyl]amino]-3-phenylpropanoyl]amino]-2,2-difluoro-5-methyl-3-oxo-N-(2,2,2-trifluoroethyl)hexanamide | 698.2 |

TABLE 1-continued

| Ex | Int. | Aspect | Structure and Name | [MH]+ |
|----|------|--------|--------------------|-------|
| 82 | IIIa, Va | white solid | 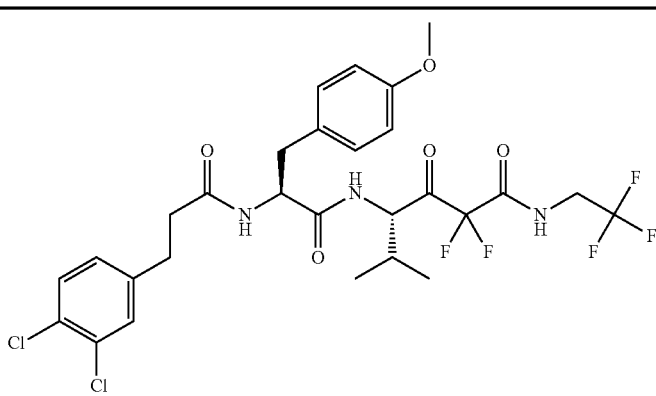<br>(4S)-4-[[(2S)-2-[3-(3,4-dichlorophenyl)propanoylamino]-3-(4-methoxyphenyl)propanoyl]amino]-2,2-difluoro-5-methyl-3-oxo-N-(2,2,2-trifluoroethyl)hexanamide | 654.1 |

Examples of Table 2 were prepared by analogy to example 2.

TABLE 2

| Ex | Int. | Aspect | Structure and Name | [MH]+ |
|----|------|--------|--------------------|-------|
| 62 | VIa | white semi-solid | 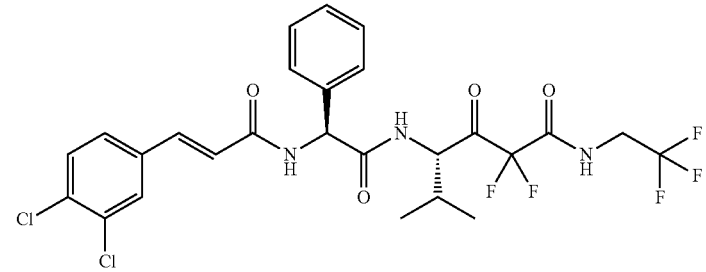 [SMILES: CC(C)[C@H](NC(=O)[C@@H](NC(=O)/C=C/c1ccc(Cl)c(Cl)c1)c1ccccc1)C(=O)C(F)(F)C(=O)NCC(F)(F)F]<br>(4S)-4-[[(2S)-2-[[(E)-(3,4-dichlorophenyl)prop-2-enoyl]amino]-2-phenylacetyl]amino]-2,2-difluoro-5-methyl-3-oxo-N-(2,2,2-trifluoroethyl)hexanamide | 608.1 |
| 63 | VIa | white solid | 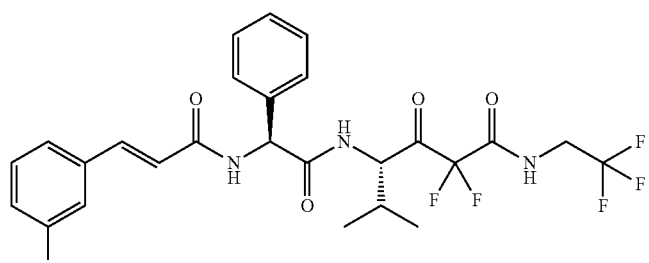<br>(4S)-4-[[(2S)-2-[[(E)-3-(3-chlorophenyl)prop-2-enoyl]amino]-2-phenylacetyl]amino]-2,2-difluoro-5-methyl-3-oxo-N-(2,2,2,-trifluoroethyl)hexanamide | 574.1 |

TABLE 2-continued

| Ex | Int. | Aspect | Structure and Name | [MH]+ |
|---|---|---|---|---|
| 64 | VIa | white solid | 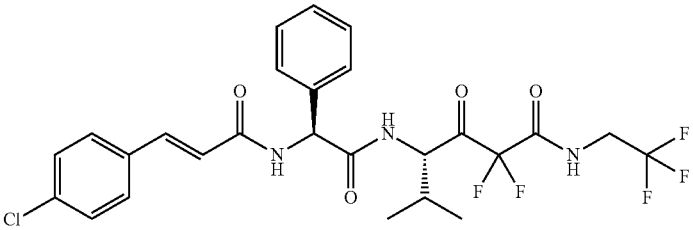 [SMILES: CC(C)[C@H](NC(=O)[C@@H](NC(=O)/C=C/c1ccc(Cl)cc1)c1ccccc1)C(=O)C(F)(F)C(=O)NCC(F)(F)F]<br>(4S)-4-[[(2S)-2-[[(E)-3-(4-chlorophenyl)prop-2-enoyl]amino]-2-phenylacetyl]amino]-2,2-difluoro-5-methyl-3-oxo-N-(2,2,2-trifluoroethyl)hexanamide | 574.1 |
| 65 | VIa, Id | white semi-solid | 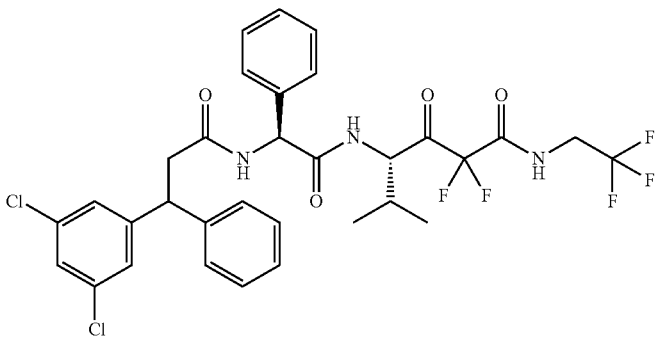 [SMILES: CC(C)[C@H](NC(=O)[C@@H](NC(=O)CC(c1ccccc1)c1cc(Cl)cc(Cl)c1)c1ccccc1)C(=O)C(F)(F)C(=O)NCC(F)(F)F]<br>(4S)-4-[[(2S)-2-[[3-(3,5-dichlorophenyl)-3-phenylpropanoyl]amino]-2-phenylacetyl]amino]-2,2-difluoro-5-methyl-3-oxo-N-(2,2,2-trifluoroethyl)hexanamide | 686.1 |
| 66 | VIb | white solid | 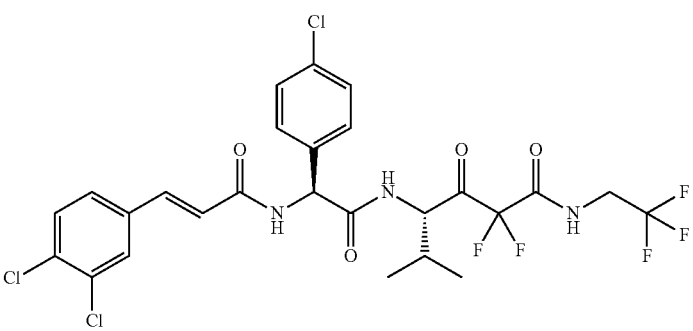 [SMILES: CC(C)[C@H](NC(=O)[C@@H](NC(=O)/C=C/c1ccc(Cl)c(Cl)c1)c1ccc(Cl)cc1)C(=O)C(F)(F)C(=O)NCC(F)(F)F]<br>(4S)-4-[[(2S)-2-(4-chlorophenyl)-2-[[(E)-3-(3,4-dichlorophenyl)prop-2-enoyl]amino]acetyl]amino]-2,2-difluoro-5-methyl-3-oxo-N-(2,2,2-trifluoroethyl)hexanamide | 642.1 |
| 67 | VIb | white solid | 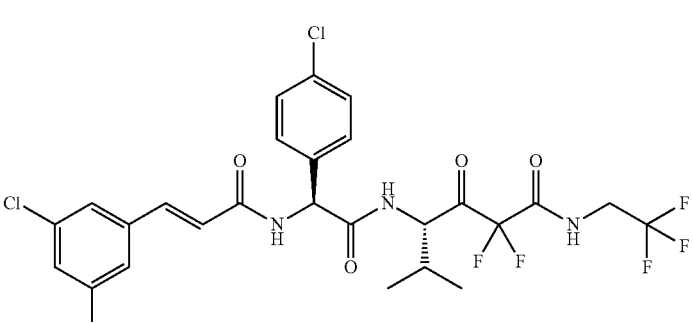<br>(4S)-4-[[(2S)-2-(4-chlorophenyl)-2-[[(E)-3-(3,5-dichlorophenyl)prop-2-enoyl]amino]acetyl]amino]-2,2-difluoro-5-methyl-3-oxo-N-(2,2,2-trifluoroethyl)hexanamide | 642.1 |

TABLE 2-continued

| Ex | Int. | Aspect | Structure and Name | [MH]+ |
|---|---|---|---|---|
| 68 | VIb | white solid | (4S)-4-[[(2S)-2-(4-chlorophenyl)-2-[[(E)-3-(3-chlorophenyl)prop-2-enoyl]amino]acetyl]amino]-2,2-difluoro-5-methyl-3-oxo-N-(2,2,2-trifluoroethyl)hexanamide | 608.1 |
| 69 | VIb | white solid | (4S)-4-[[(2S)-2-(4-chlorophenyl)-2-[[(E)-3-(4-chlorophenyl)prop-2-enoyl]amino]acetyl]amino]-2,2-difluoro-5-methyl-3-oxo-N-(2,2,2-trifluoroethyl)hexanamide | 608.1 |
| 70 | VIa, IIa | white solid | (4S)-4-[[(2S)-2-[[3-(3,4-dichlorophenyl)-3-phenoxypropanoyl]amino]-2-phenylacetyl]amino]-2,2-difluoro-5-methyl-3-oxo-N-(2,2,2-trifluoroethyl)hexanamide | 702.2 |
| 72 | VIa, IIb | white solid | (4S)-4-[[(2S)-2-[[3-(4-chlorophenoxy)-3-(3,4-dichlorophenyl)propanoyl]amino]-2-phenylacetyl]amino]-2,2-difluoro-5-methyl-3-oxo-N-(2,2,2-trifluoroethyl)hexanamide | 736.1 |

TABLE 2-continued

| Ex | Int. | Aspect | Structure and Name | [MH]+ |
|---|---|---|---|---|
| 74 | VIa, (+) – VII | white semi-solid | (4S)-4-[[(2S)-2-[[(3S)-3-(3,5-dichlorophenyl)-3-phenylpropanoyl]amino]-2-phenylacetyl]amino]-2,2-difluoro-5-methyl-3-oxo-N-(2,2,2-trifluoroethyl)hexanamide* | 686.1 |
| 75 | VIa, If | white foam | (4S)-4-[[(2S)-2-[[3-(3,5-difluorophenyl)-3-(4-methoxyphenyl)propanoyl]amino]-2-phenylacetyl]amino]-2,2-difluoro-5-methyl-3-oxo-N-(2,2,2-trifluoroethyl)hexanamide | 684.2 |
| 77 | VIb, (+) – VII | white solid | (4S)-4-[[(2S)-2-(4-chlorophenyl)-2-[[(3S)-3-(3,5-dichlorophenyl)-3-phenylpropanoyl]amino]acetyl]amino]-2,2-difluoro-5-methyl-3-oxo-N-(2,2,2-trifluoroethyl)hexanamide* | 720.1 |

TABLE 2-continued

| Ex | Int. | Aspect | Structure and Name | [MH]+ |
|---|---|---|---|---|
| 78 | VIa, (−)−VII | white semi-solid | (4S)-4-[[(2S)-2-[[(3R)-3-(3,5-dichlorophenyl)-3-phenylpropanoyl]amino]-2-phenylacetyl]amino]-2,2-difluoro-5-methyl-3-oxo-N-(2,2,2-trifluoroethyl)hexanamide* | 686.2 |
| 79 | VIb, (−)−VII | white semi-solid | (4S)-4-[[(2S)-2-(4-chlorophenyl)-2-[[(3R)-3-(3,5-dichlorophenyl)-3-phenylpropanoyl]amino]acetyl]amino]-2,2-difluoro-5-methyl-3-oxo-N-(2,2,2-trifluoroethyl)hexanamide | 720.2 |
| 80 | VIb, IIc | white foam | (4S)-4-[[(2S)-2-[[(3S)-3-(3-chlorophenoxy)-3-phenylpropanoyl]amino]-2-(4-chlorophenyl)acetyl]amino]-2,2-difluoro-5-methyl-3-oxo-N-(2,2,2-trifluoroethyl)hexanamide | 702.1 |

TABLE 2-continued

| Ex | Int. | Aspect | Structure and Name | [MH]+ |
|---|---|---|---|---|
| 81 | VIa, IIc | white foam | 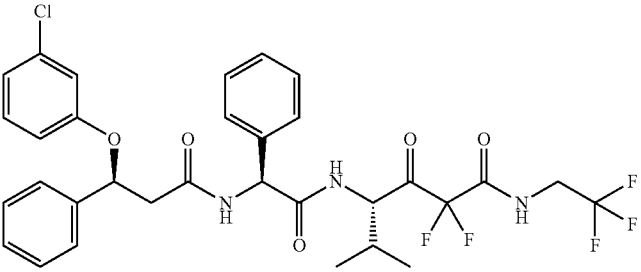 [SMILES: CC(C)[C@H](NC(=O)[C@@H](NC(=O)C[C@H](Oc1cccc(Cl)c1)c1ccccc1)c1ccccc1)C(=O)C(F)(F)C(=O)NCC(F)(F)F]<br>(4S)-4-[[(2S)-2-[[(3S)-3-(3-chlorophenoxy)-3-phenylpropanoyl]amino]-2-phenylacetyl]amino]-2,2-difluoro-5-methyl-3-oxo-N-(2,2,2-trifluoroethyl)hexanamide | 668.2 |
| 84 | VIa, Ig | white solid | 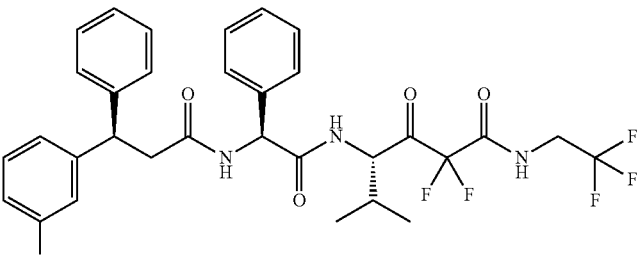<br>(4S)-4-[[(2S)-2-[[3-(3-chlorophenyl)-3-phenylpropanoyl]amino]-2-phenylacetyl]amino]-2,2-difluoro-5-methyl-3-oxo-N-(2,2,2-trifluoroethyl)hexanamide | 652.2 |
| 85 | VIb, Ig | white solid | 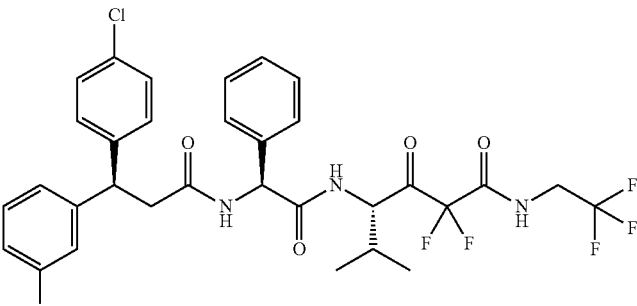<br>(4S)-4-[[(2S)-2-(4-chlorophenyl)-2-[[3-(3-chlorophenyl)-3-phenylpropanoyl]amino]acetyl]amino]-2,2-difluoro-5-methyl-3-oxo-N-(2,2,2-trifluoroethyl)hexanamide | 686.1 |

The asterisk (*) at the diphenyl-methine chiral centre of examples 74, 77, 78 and 79 denotes a chiral center which can have either a R or S configuration. The diphenyl-methine chiral centre of examples 74, 77, 78 and 79 is not present as a racemic mixture of this centre.

Example 83

(4S)-4-[[(2S)-2-[[2-(3,5-Dichlorophenoxy)acetyl]amino]-2-(4-methoxyphenyl)acetyl]amino]-2,2-difluoro-5-methyl-3-oxo-N-(2,2,2-trifluoroethyl)hexanamide

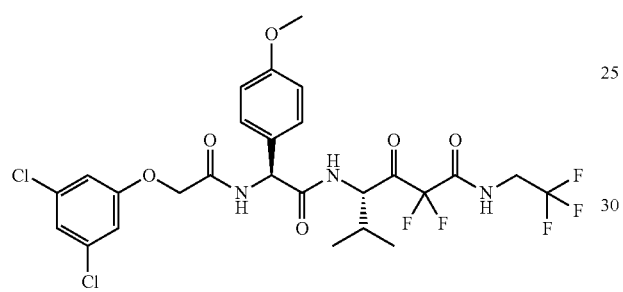

A] (3R,4 S)-4-[[(2S)-2-[[2-(3,5-Dichlorophenoxy)acetyl]amino]-2-(4-methoxyphenyl)acetyl]amino]-2,2-difluoro-3-hydroxy-5-methyl-N-(2,2,2-trifluoroethyl)hexanamide

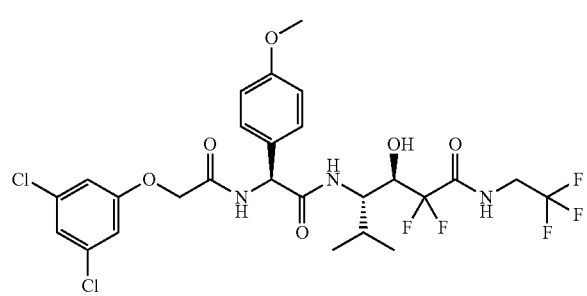 [SMILES: COc1ccc([C@H](NC(=O)COc2cc(Cl)cc(Cl)c2)C(=O)N[C@@H](C(C)C)[C@@H](O)C(F)(F)C(=O)NCC(F)(F)F)cc1]

To a mixture of 2-(3,5-dichlorophenoxy)acetic acid (40.7 mg, 184 Eq: 1) and N,N-diisopropylethylamine (119 mg, 161 µl, 920 µmol, Eq: 5) in DMF (4 ml) were added at 0° C. (4S)-4-((S)-2-amino-2-(4-methoxyphenyl)acetamido)-2,2-difluoro-3-hydroxy-5-methyl-N-(2,2,2-trifluoroethyl)hexanamide hydrochloride (Intermediate VIc, 87.9 mg, 184 µmol, Eq: 1) and HATU (84 mg, 221 µmol, Eq: 1.2) and the reaction allowed to proceed for 2 hr at rt. The reaction mixture was quenched with sat. NaHCO₃ and extracted with EtOAc (2×25 mL). The organic layers were washed subsequently with 1N KHSO₄ and with H₂O/NaCl sol. The organic layers were combined, dried over Na₂SO₄ and concentrated in vacuo. Purification by flash chromatography (silica gel, 20 g, 15% to 80% EtOAc in heptane) yielded 64 mg of the title compound as white foam; MS: 644.1 (M+H)⁺.

B] (4S)-4-[[(2S)-2-[[2-(3,5-Dichlorophenoxy)acetyl]amino]-2-(4-methoxyphenyl)acetyl]amino]-2,2-difluoro-5-methyl-3-oxo-N-(2,2,2-trifluoroethyl)hexanamide

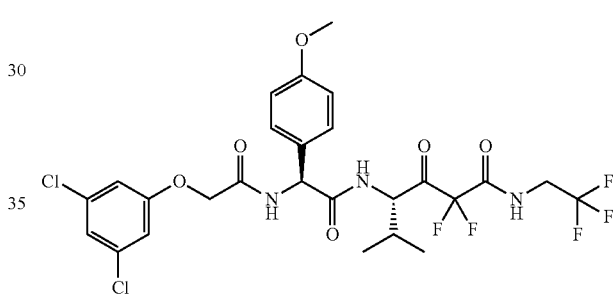

In a 10 mL round-bottomed flask, the above prepared (4S)-4-((S)-2-(2-(3,5-dichlorophenoxy)acetamido)-2-(4-methoxyphenyl)acetamido)-2,2-difluoro-3-hydroxy-5-methyl-N-(2,2,2-trifluoroethyl)hexanamide (62 mg, 96.2 µmol, Eq: 1) was combined with Dichloromethane (4 ml) to give a colorless solution. Dess-Martin periodinane 15% in dichloromethane (408 mg, 300 µl, 144 µmol, Eq: 1.5) was added at 0° C. and the reaction mixture was stirred 2 hr at rt. Work up: The reaction mixture was treated with sat. NaHCO₃ and extracted with DCM (2×20 mL). The organic layers were washed with brine, dried (Na₂SO₄) and evaporated. The crude material was purified by flash chromatography (silica gel, 10 g, 33% to 50% EtOAc in heptane) to afford 49 mg of the title product as white solid; MS: 642.1 (M+H)⁺.

Examples of Table 3 were prepared by analogy to example 83.

TABLE 3

| Ex | Int. | Aspect | Structure and Name | [MH]+ |
|---|---|---|---|---|
| 86 | (E)-3-(4-chlorophenyl)prop-2-enoic acid, IVc | white solid | (4S)-4-[[(2S)-2-[[(E)-3-(4-chlorophenyl)prop-2-enoyl]amino]-2-(4-methoxyphenyl)acetyl]amino]-2,2-difluoro-5-methyl-3-oxo-N-(2,2,2-trifluoroethyl)hexanamide | 604.1 |
| 87 | VIc, Ic | white solid | (4S)-4-[[(2S)-2-[[3-(3,4-dichlorophenyl)-3-phenylpropanoyl]amino]-2-(4-methoxyphenyl)acetyl]amino]-2,2-difluoro-5-methyl-3-oxo-N-(2,2,2-trifluoroethyl)hexanamide | 716.2 |
| 88 | VIa, IId | white solid | (4S)-4-[[(2S)-2-[[3-(3-chlorophenoxy)-3-(3,4-dichlorophenyl)propanoyl]amino]-2-phenylacetyl]amino]-2,2-difluoro-5-methyl-3-oxo-N-(2,2,2-trifluoroethyl)hexanamide | 736.1 |

TABLE 3-continued

| Ex | Int. | Aspect | Structure and Name | [MH]+ |
|---|---|---|---|---|
| 89 | VIb, IId | Off-white solid | (4S)-4-[[(2S)-2-[[3-(3-chlorophenoxy)-3-(3,4-dichlorophenyl)propanoyl]amino]-2-(4-chlorophenyl)acetyl]amino]-2,2-difluoro-5-methyl-3-oxo-N-(2,2,2-trifluoroethyl)hexanamide | 770.0 |
| 90 | VIa, IIe | white foam | (4S)-4-[[(2S)-2-[[(3R)-3-(3-chlorophenoxy)-3-phenylpropanoyl]amino]-2-phenylacetyl]amino]-2,2-difluoro-5-methyl-3-oxo-N-(2,2,2-trifluoroethyl)hexanamide | 668.2 |
| 91 | VIb, IIe | white foam | (4S)-4-[[(2S)-2-[[(3R)-3-(3-chlorophenoxy)-3-phenylpropanoyl]amino]-2-(4-chlorophenyl)acetyl]amino]-2,2-difluoro-5-methyl-3-oxo-N-(2,2,2-trifluoroethyl)hexanamide | 702.2 |
| 92 | VIb, IIf | off-white solid | (4S)-4-[[(2S)-2-[[(3S)-3-(4-chlorophenoxy)-3-(3,4-dichlorophenyl)propanoyl]amino]-2-(4-chlorophenyl)acetyl]amino]-2,2-difluoro-5-methyl-3-oxo-N-(2,2,2-trifluoroethyl)hexanamide | 770.0 |

TABLE 3-continued

| Ex | Int. | Aspect | Structure and Name | [MH]+ |
|---|---|---|---|---|
| 93 | VId, IIb | light-yellow oil | (4S)-4-[[(2S)-2-[[3-(4-chlorophenoxy)-3-(3,4-dichlorophenyl)propanoyl]amino]-2-phenylacetyl]amino]-2,2-difluoro-5-methyl-N-(2-morpholin-4-ylethyl)-3-oxohexanamide | 767.3 |
| 94 | VId, (E)-3-(3,4-di-chloro-phenyl)prop-2-enoic acid | colorless oil | (4S)-4-[[(2S)-2-[[(E)-3-(3,4-dichlorophenyl)prop-2-enoyl]amino]-2-phenylacetyl]amino]-2,2-difluoro-5-methyl-N-(2-morpholin-4-ylethyl)-3-oxohexanamide | 639.2 |
| 95 | VIe, 2-(3,5-di-chloro-phenyl)sulfanyl acetic acid | white solid | (4S)-4-[[(2S)-2-[[2-(3,5-dichlorophenyl)sulfanylacetyl]amino]-3-phenylpropanoyl]amino]-2,2-difluoro-5-methyl-3-oxo-N-(2,2,2-trifluoroethyl)hexanamide | 642.1 |
| 96 | VIa, IIg | colorless oil | (4S)-4-[[(2S)-2-[[3-(3-chlorophenoxy)-3-(5-chloropyridin-3-yl)propanoyl]amino]-2-phenylacetyl]amino]-2,2-difluoro-5-methyl-3-oxo-N-(2,2,2-trifluoroethyl)hexanamide | 703.2 |

TABLE 3-continued

| Ex | Int. | Aspect | Structure and Name | [MH]+ |
|---|---|---|---|---|
| 97 | VIa, IIh | off-white solid | (4S)-4-[[(2S)-2-[[3-(3-chlorophenyl)-3-pyridin-3-yloxypropanoyl]amino]-2-phenylacetyl]amino]-2,2-difluoro-5-methyl-3-oxo-N-(2,2,2-trifluoroethyl)hexanamide | 669.3 |
| 98 | VIc, IIi | | (4S)-4-[[(2S)-2-[[3-(3-chlorophenyl)-3-(5-chloropyridin-3-yl)oxypropanoyl]amino]-2-(4-methoxyphenyl)acetyl]amino]-2,2-difluoro-5-methyl-3-oxo-N-(2,2,2-trifluoroethyl)hexanamide | 733.4 |

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

We claim:
1. A compound of formula (I)

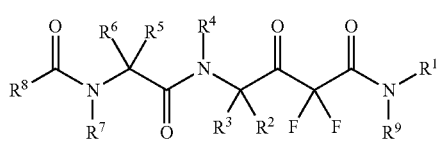

wherein:
$R^1$ is alkyl, optionally substituted cycloalkyl, haloalkyl, optionally substituted heterocycloalkylalkyl optionally substituted arylalkyl or optionally substituted heteroarylalkyl, wherein each moiety is optionally substituted by one to three substituents independently selected from halogen, alkyl, haloalkyl, cycloalkyl, cyano, hydroxyl, alkoxy, haloalkoxy or phenyl;
$R^2$, $R^3$ $R^4$, $R^6$, $R^7$ and $R^9$ are independently selected from hydrogen, alkyl or cycloalkyl;

R⁵ is optionally substituted aryl, optionally substituted arylalkyl, optionally substituted heteroaryl or optionally substituted heteroarylalkyl, wherein each moiety is optionally substituted by one to three substituents independently selected from halogen, alkyl, haloalkyl, cycloalkyl, cyano, hydroxyl, alkoxy, haloalkoxy or phenyl;

R⁸ is optionally substituted adamantylalkyl, optionally substituted cycloalkyl, optionally substituted cycloalkylalkyl, optionally substituted dicycloalkylalkyl, optionally substituted aryl, optionally substituted arylalkyl, optionally substituted arylalkenyl, optionally substituted diarylalkyl, optionally substituted aryloxyalkyl, optionally substituted diaryloxyalkyl, optionally substituted arylaryloxyalkyl, optionally substituted heteroarylaryloxyalkyl, optionally substituted heteroaryl, optionally substituted heteroarylalkyl, optionally substituted heteroarylalkenyl, optionally substituted arylheteroarylalkyl, optionally substituted arylheteroaryloxyalkyl or optionally substituted aryloxyheteroarylalkyl, wherein each moiety is optionally substituted by one to three substituents independently from selected halogen, alkyl, haloalkyl, cycloalkyl, cyano, hydroxyl, alkoxy, haloalkoxy or phenyl;

wherein a heterocycloalkyl moiety is a ring system of 4 to 9 ring atoms, comprising 1, 2, or 3 ring heteroatoms selected from N, O and S, the remaining ring atoms being carbon, heteroaryl moiety is a ring system of 5 or ring atoms, comprising 1, 2, 3 or 4 heteroatoms selected from N, O and S; the remaining ring atoms being carbon and an aryl moiety is a monovalent aromatic carbocyclic mono- or bicyclic ring system comprising 6 to 10 carbon ring atoms;

or, a pharmaceutically acceptable salt thereof.

2. The compound according to claim 1, wherein R¹ is alkyl, haloalkyl, optionally substituted heterocycloalkylalkyl or optionally substituted phenylalkyl, wherein each moiety is optionally substituted by one to three substituents independently selected from halogen, alkyl, haloalkyl, cycloalkyl, cyano, hydroxyl, alkoxy, haloalkoxy or phenyl.

3. The compound according to claim 2, wherein R¹ is haloalkyl.

4. The compound according to claim 2, wherein R¹ is optionally substituted heterocycloalkylalkyl or optionally substituted phenylalkyl.

5. The compound according to claim 2, wherein R⁹ is hydrogen.

6. The compound according to claim 2, wherein R² is alkyl.

7. The compound according to claim 2, wherein R³ is hydrogen.

8. The compound according to claim 2, wherein R⁴ is hydrogen.

9. The compound according to claim 2, wherein R⁵ is optionally substituted phenyl or optionally substituted phenylalkyl wherein each moiety is optionally substituted by one to three substituents independently selected from halogen, alkyl, haloalkyl, cycloalkyl, cyano, hydroxyl, alkoxy, haloalkoxy or phenyl.

10. The compound according to claim 9, wherein each moiety is optionally substituted by one to three substituents independently selected from halogen or alkoxy.

11. The compound according to claim 10, wherein each moiety is optionally substituted by one to three halogens.

12. The compound according to claim 2, wherein R⁶ is hydrogen.

13. The compound according to claim 2, wherein R⁷ is hydrogen.

14. The compound according to claim 2, wherein R⁸ is optionally substituted phenylalkyl, optionally substituted phenylalkenyl, optionally substituted diphenylalkyl, optionally substituted phenoxyalkyl, optionally substituted pyridinylphenoxyalkyl, optionally substituted phenylpyridinyloxyalkyl or optionally substituted phenylphenoxyalkyl wherein each moiety is optionally substituted by one to three substituents independently selected from halogen, alkyl, haloalkyl, cycloalkyl, cyano, hydroxyl, alkoxy, haloalkoxy or phenyl.

15. The compound according to claim 14, wherein R⁸ is optionally substituted phenylalkyl, optionally substituted phenylalkenyl, optionally substituted diphenylalkyl, optionally substituted phenoxyalkyl or optionally substituted phenylphenoxyalkyl.

16. The compound according to claim 15, wherein R⁸ is optionally substituted phenoxyalkyl or optionally substituted phenylphenoxyalkyl.

17. The compound according to claim 15, wherein R⁸ is phenoxyalkyl or phenylphenoxyalkyl optionally substituted with one to three halogens.

18. The compound according to claim 1, wherein the compound is of formula (Ia)

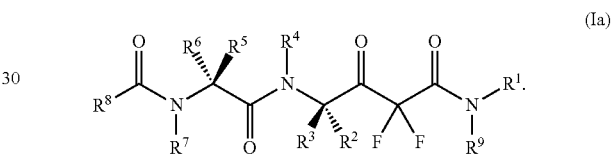

(Ia)

19. The compound according to claim 18, wherein

R¹ is haloalkyl;

R² is alkyl;

R³ R⁴, R⁶, R⁷ and R⁹ are hydrogen;

R⁵ is optionally substituted phenyl or optionally substituted phenylalkyl, wherein each moiety is optionally substituted by one to three independently selected halogens;

R⁸ is optionally substituted phenoxyalkyl or optionally substituted phenylphenoxyalkyl, wherein each moiety is optionally substituted by one to three independently selected halogens;

or, pharmaceutically acceptable salt thereof.

20. The compound according to claim 1 which compound is selected from the group consisting of:

(4 S)-4-[[(2 S)-2-[3-(3-chlorophenyl)propanoyl amino]-3-phenylpropanoyl]amino]-2,2-difluoro-5-methyl-N-(2-morpholin-4-ylethyl)-3-oxohexanamide;

(S)-4-((S)-2-((E)-3-(3,5-dichlorophenyl)acrylamido)-2-phenylacetamido)-2,2-difluoro-5-methyl-3-oxo-N-(2,2,2-trifluoroethyl)hexanamide;

(S)-4-((S)-2-(3-(3-chlorophenyl)propanamido)-3-phenylpropanamido)-2,2-difluoro-5-methyl-3-oxo-N-phenethylhexanamide;

(S)-4-((S)-2-(3-(3-chlorophenyl)propanamido)-3-phenylpropanamido)-2,2-difluoro-5-methyl-3-oxo-N-(3,3,3-trifluoropropyl)hexanamide;

(S)-4-((S)-2-(3-(3,4-dichlorophenyl)propanamido)-3-phenylpropanamido)-2,2-difluoro-5-methyl-3-oxo-N-(2,2,2-trifluoroethyl)hexanamide;

(S)-4-((S)-2-(2-(3-chlorophenoxy)acetamido)-3-phenylpropanamido)-2,2-difluoro-5-methyl-3-oxo-N-(2,2,2-trifluoroethyl)hexanamide;

(S)-4-((S)-2-(2-(3,4-dichlorophenoxy)acetamido)-3-phenylpropanamido)-2,2-difluoro-5-methyl-3-oxo-N-(2,2,2-trifluoroethyl)hexanamide;

(S)-4-((S)-2-(3-(3,5-dichlorophenyl)propanamido)-3-phenylpropanamido)-2,2-difluoro-5-methyl-3-oxo-N-(2,2,2-trifluoroethyl)hexanamide;

(S)-4-((S)-2-(2-(3,5-dichlorophenoxy)acetamido)-3-phenylpropanamido)-2,2-difluoro-5-methyl-3-oxo-N-(2,2,2-trifluoroethyl)hexanamide;

(S)-4-((S)-2-(3-(3-chlorophenyl)propanamido)-3-phenylpropanamido)-2,2-difluoro-5-methyl-3-oxo-N-(2,2,2-trifluoroethyl)hexanamide;

(S)-4-((S)-2-(2-(3,4-dichlorophenoxy)acetamido)-3-phenylpropanamido)-2,2-difluoro-5-methyl-N-(2-morpholinoethyl)-3-oxohexanamide;

(S)-4-((S)-2-(2-(3-chlorophenoxy)acetamido)-3-phenylpropanamido)-2,2-difluoro-5-methyl-N-(2-morpholinoethyl)-3-oxohexanamide;

(S)-4-((S)-2-(2-(3,5-dichlorophenoxy)acetamido)-3-phenylpropanamido)-2,2-difluoro-5-methyl-N-(2-morpholinoethyl)-3-oxohexanamide;

(S)-4-((S)-2-(3-(3,5-dichlorophenyl)propanamido)-3-phenylpropanamido)-2,2-difluoro-5-methyl-N-(2-morpholinoethyl)-3-oxohexanamide;

(S)-4-((S)-2-(3-(3,4-dichlorophenyl)propanamido)-3-phenylpropanamido)-2,2-difluoro-5-methyl-N-(2-morpholinoethyl)-3-oxohexanamide;

(S)-4-((S)-2-(3-(3,4-dichlorophenyl)propanamido)-3-phenylpropanamido)-2,2-difluoro-5-methyl-3-oxo-N-phenethylhexanamide;

(S)-4-((S)-2-(2-(3-chlorophenoxy)acetamido)-3-phenylpropanamido)-2,2-difluoro-5-methyl-3-oxo-N-phenethylhexanamide;

(S)-4-((S)-2-(3-(3,4-dichlorophenyl)propanamido)-3-phenylpropanamido)-2,2-difluoro-5-methyl-3-oxo-N-(3,3,3-trifluoropropyl)hexanamide;

(S)-4-((S)-2-(2-(3,5-dichlorophenoxy)acetamido)-3-phenylpropanamido)-2,2-difluoro-5-methyl-3-oxo-N-(3,3,3-trifluoropropyl)hexanamide;

(S)-4-((S)-2-(2-(3-chlorophenoxy)acetamido)-3-phenylpropanamido)-2,2-difluoro-5-methyl-3-oxo-N-(3,3,3-trifluoropropyl)hexanamide;

(S)-4-((S)-2-(3-(3,5-dichlorophenyl)propanamido)-3-phenylpropanamido)-2,2-difluoro-5-methyl-3-oxo-N-(3,3,3-trifluoropropyl)hexanamide;

(S)-4-((S)-2-(2-(3,4-dichlorophenoxy)acetamido)-3-phenylpropanamido)-2,2-difluoro-5-methyl-3-oxo-N-(3,3,3-trifluoropropyl)hexanamide;

(S)-4-((S)-3-(4-chlorophenyl)-2-(3-(3,4-dichlorophenyl)propanamido)propanamido)-2,2-difluoro-5-methyl-3-oxo-N-phenethylhexanamide;

(S)-4-((S)-2-(3-(3,4-dichlorophenyl)propanamido)-3-(3,4-dimethoxyphenyl)propanamido)-2,2-difluoro-5-methyl-3-oxo-N-phenethylhexanamide;

(S)-4-((S)-2-(3-(3,4-dichlorophenyl)propanamido)-3-(3,4-dimethoxyphenyl)propanamido)-2,2-difluoro-5-methyl-3-oxo-N-(2,2,2-trifluoroethyl)hexanamide;

(S)-4-((S)-3-(3,4-dichlorophenyl)-2-(3-(3,4-di chlorophenyl)propanamido)propanamido)-2,2-difluoro-5-methyl-3-oxo-N-phenethylhexanamide;

(S)-4-((S)-3-(4-chlorophenyl)-2-(2-(3,5-dichlorophenoxy)acetamido)propanamido)-2,2-difluoro-5-methyl-3-oxo-N-(2,2,2-trifluoroethyl)hexanamide;

(S)-4-((S)-2-(2-(3,5-dichlorophenoxy)acetamido)-3-(3,4-dichlorophenyl)propanamido)-2,2-difluoro-5-methyl-3-oxo-N-(2,2,2-trifluoroethyl)hexanamide;

(S)-4-((S)-2-(2-(3,5-dichlorophenoxy)acetamido)-3-phenylpropanamido)-N-ethyl-2,2-difluoro-5-methyl-3-oxohexanamide;

(S)-4-((S)-2-(2-(3,5-dichlorophenoxy)acetamido)-3-phenylpropanamido)-2,2-difluoro-N-isobutyl-5-methyl-3-oxohexanamide;

(S)-4-((S)-2-(2-(3,5-dichlorophenoxy)acetamido)-3-(3,4-dichlorophenyl)propanamido)-N-ethyl-2,2-difluoro-5-methyl-3-oxohexanamide;

(S)-4-((S)-2-(2-(3,5-dichlorophenoxy)acetamido)-3-(3,4-dichlorophenyl)propanamido)-2,2-difluoro-N-isobutyl-5-methyl-3-oxohexanamide;

(S)-4-((S)-2-(2-(3,5-dichlorophenoxy)acetamido)-3-(3,4-difluorophenyl)propanamido)-2,2-difluoro-N-isobutyl-5-methyl-3-oxohexanamide;

(S)-4-((S)-3-(4-chlorophenyl)-2-(2-(3,5-dichlorophenoxy)acetamido)propanamido)-2,2-difluoro-5-methyl-3-oxo-N-(3,3,3-trifluoropropyl)hexanamide;

(S)-4-((S)-2-(2-(3,5-dichlorophenoxy)acetamido)-3-(3,4-dichlorophenyl)propanamido)-2,2-difluoro-5-methyl-3-oxo-N-(3,3,3-trifluoropropyl)hexanamide;

(S)-4-((S)-2-(2-(3,5-dichlorophenoxy)acetamido)-3-(3,4-difluorophenyl)propanamido)-2,2-difluoro-5-methyl-3-oxo-N-(3,3,3-trifluoropropyl)hexanamide;

(S)-4-((S)-2-(2-(3,5-dichlorophenoxy)acetamido)-3-(3,4-dimethoxyphenyl)propanamido)-2,2-difluoro-5-methyl-3-oxo-N-(3,3,3-trifluoropropyl)hexanamide;

(S)-4-((S)-2-(2-(3,5-dichlorophenoxy)acetamido)-3-phenylpropanamido)-2,2-difluoro-5-methyl-3-oxo-N-propylhexanamide;

(S)-4-((S)-2-(2-(3,5-dichlorophenoxy)acetamido)-3-phenylpropanamido)-2,2-difluoro-5-methyl-N-neopentyl-3-oxohexanamide;

(4S)-4-((2 S)-2-(3-(3,4-dichlorophenyl)-3-phenylpropanamido)-3-phenylpropanamido)-2,2-difluoro-5-methyl-3-oxo-N-(2,2,2-trifluoroethyl)hexanamide;

(S)-4-((S)-3-(4-chlorophenyl)-2-(2-(3,5-dichlorophenoxy)acetamido)propanamido)-2,2-difluoro-5-methyl-3-oxo-N-propylhexanamide;

(S)-4-((S)-2-(2-(3,5-dichlorophenoxy)acetamido)-3-(3,4-difluorophenyl)propanamido)-2,2-difluoro-5-methyl-N-neopentyl-3-oxohexanamide;

(S)-4-((S)-2-(2-(3,5-dichlorophenoxy)acetamido)-3-(3,4-difluorophenyl)propanamido)-2,2-difluoro-5-methyl-3-oxo-N-(2,2,2-trifluoroethyl)hexanamide;

(S)-4-((S)-2-(2-(3,5-dichlorophenoxy)acetamido)-3-(3,4-dimethoxyphenyl)propanamido)-2,2-difluoro-5-methyl-3-oxo-N-(2,2,2-trifluoroethyl)hexanamide;

(4S)-4-((2S)-2-(3-(3,4-dichlorophenyl)-3-(4-methoxyphenyl)propanamido)-3-phenylpropanamido)-2,2-difluoro-5-methyl-3-oxo-N-(2,2,2-trifluoroethyl)hexanamide;

(S)-4-((S)-2-((E)-3-(3,4-dichlorophenyl)acrylamido)-3-phenylpropanamido)-2,2-difluoro-5-methyl-3-oxo-N-propylhexanamide;

(S)-4-((S)-2-((E)-3-(3,4-dichlorophenyl)acrylamido)-3-phenylpropanamido)-2,2-difluoro-5-methyl-N-neopentyl-3-oxohexanamide;

(S)-4-((S)-2-((E)-3-(3,4-dichlorophenyl)acrylamido)-3-phenylpropanamido)-2,2-difluoro-5-methyl-3-oxo-N-(2,2,2-trifluoroethyl)hexanamide;

(S)-4-((S)-2-((E)-3-(3,5-dichlorophenyl)acrylamido)-3-phenylpropanamido)-2,2-difluoro-5-methyl-3-oxo-N-(2,2,2-trifluoroethyl)hexanamide;

(S)-4-((S)-2-(4-chlorophenyl)-2-(2-(3,5-dichlorophenoxy)acetamido)acetamido)-2,2-difluoro-5-methyl-3-oxo-N-(2,2,2-trifluoroethyl)hexanamide;

(S)-4-((S)-2-(3,3-diphenylpropanamido)-3-phenylpropanamido)-2,2-difluoro-5-methyl-3-oxo-N-(2,2,2-trifluoroethyl)hexanamide;
(4S)-4-((2S)-2-(3-(3,5-dichlorophenyl)-3-(4-methoxyphenyl)propanamido)-3-phenylpropanamido)-2,2-difluoro-5-methyl-3-oxo-N-(2,2,2-trifluoroethyl)hexanamide;
(4S)-4-((2S)-3-(4-chlorophenyl)-2-(3-(3,4-dichlorophenyl)-3-phenylpropanamido)propanamido)-2,2-difluoro-5-methyl-3-oxo-N-(2,2,2-trifluoroethyl)hexanamide;
(4S)-4-((2S)-2-(3-(3,4-dichlorophenyl)-3-phenylpropanamido)-3-(4-methoxyphenyl)propanamido)-2,2-difluoro-5-methyl-3-oxo-N-(2,2,2-trifluoroethyl)hexanamide;
(4#S!)-4-[[(2#S!)-2-[[2-(3,5-dichlorophenoxy)acetyl]amino]-2-phenylacetyl]amino]-2,2-difluoro-5-methyl-3-oxo-#N!-(2,2,2-trifluoroethyl)hexanamide;
(S)-4-((S)-2-(2-(3,5-dichlorophenoxy)acetamido)-2-(4-fluorophenyl)acetamido)-2,2-difluoro-5-methyl-3-oxo-N-(2,2,2-trifluoroethyl)hexanamide;
(4S)-4-((2S)-2-(3-(3,4-dichlorophenyl)-3-phenylpropanamido)-2-phenylacetamido)-2,2-difluoro-5-methyl-3-oxo-N-(2,2,2-trifluoroethyl)hexanamide;
(4S)-4-((2S)-2-(4-chlorophenyl)-2-(3-(3,4-dichlorophenyl)-3-phenylpropanamido)acetamido)-2,2-difluoro-5-methyl-3-oxo-N-(2,2,2-trifluoroethyl)hexanamide;
(S)-4-((S)-2-(3-(3,4-dichlorophenyl)propanamido)-2-phenylacetamido)-2,2-difluoro-5-methyl-3-oxo-N-(2,2,2-trifluoroethyl)hexanamide;
(4S)-4-((2S)-2-(3-(4-bromophenyl)-3-phenylpropanamido)-3-phenylpropanamido)-2,2-difluoro-5-methyl-3-oxo-N-(2,2,2-trifluoroethyl)hexanamide;
(4S)-4-((2S)-2-(3-(4-bromophenyl)-3-phenylpropanamido)-3-(4-chlorophenyl)propanamido)-2,2-difluoro-5-methyl-3-oxo-N-(2,2,2-trifluoroethyl)hexanamide;
(S)-4-((S)-2-((E)-3-(3,4-dichlorophenyl)acrylamido)-2-phenylacetamido)-2,2-difluoro-5-methyl-3-oxo-N-(2,2,2-trifluoroethyl)hexanamide;
(S)-4-((S)-2-((E)-3-(3-chlorophenyl)acrylamido)-2-phenylacetamido)-2,2-difluoro-5-methyl-3-oxo-N-(2,2,2-trifluoroethyl)hexanamide;
(S)-4-((S)-2-((E)-3-(4-chlorophenyl)acrylamido)-2-phenylacetamido)-2,2-difluoro-5-methyl-3-oxo-N-(2,2,2-trifluoroethyl)hexanamide;
(4S)-4-((2S)-2-(3-(3,5-dichlorophenyl)-3-phenylpropanamido)-2-phenylacetamido)-2,2-difluoro-5-methyl-3-oxo-N-(2,2,2-trifluoroethyl)hexanamide;
(S)-4-((S)-2-(4-chlorophenyl)-2-((E)-3-(3,4-dichlorophenyl)acrylamido)acetamido)-2,2-difluoro-5-methyl-3-oxo-N-(2,2,2-trifluoroethyl)hexanamide;
(S)-4-((S)-2-(4-chlorophenyl)-2-((E)-3-(3,5-dichlorophenyl)acrylamido)acetamido)-2,2-difluoro-5-methyl-3-oxo-N-(2,2,2-trifluoroethyl)hexanamide;
(S)-4-((S)-2-(4-chlorophenyl)-2-((E)-3-(3-chlorophenyl)acrylamido)acetamido)-2,2-difluoro-5-methyl-3-oxo-N-(2,2,2-trifluoroethyl)hexanamide;
(S)-4-((S)-2-(4-chlorophenyl)-2-((E)-3-(4-chlorophenyl)acrylamido)acetamido)-2,2-difluoro-5-methyl-3-oxo-N-(2,2,2-trifluoroethyl)hexanamide;
(4S)-4-((2 S)-2-(3-(3,4-dichlorophenyl)-3-phenoxypropanamido)-2-phenylacetamido)-2,2-difluoro-5-methyl-3-oxo-N-(2,2,2-trifluoroethyl)hexanamide;
(4S)-4-((2 S)-2-(3-(3,4-dichlorophenyl)-3-phenoxypropanamido)-3-phenylpropanamido)-2,2-difluoro-5-methyl-3-oxo-N-(2,2,2-trifluoroethyl)hexanamide;
(4S)-4-((2 S)-2-(3-(4-chlorophenoxy)-3-(3,4-dichlorophenyl)propanamido)-2-phenyl acetamido)-2,2-difluoro-5-methyl-3-oxo-N-(2,2,2-trifluoroethyl)hexanamide;
(4S)-4-((2S)-2-(3-(4-chlorophenoxy)-3-(3,4-dichlorophenyl)propanamido)-3-phenylpropanamido)-2,2-difluoro-5-methyl-3-oxo-N-(2,2,2-trifluoroethyl)hexanamide;
(S)-4-((S)-2-((S)-3-(3,5-dichlorophenyl)-3-phenylpropanamido)-2-phenylacetamido)-2,2-difluoro-5-methyl-3-oxo-N-(2,2,2-trifluoroethyl)hexanamide;
(4S)-4-((2 S)-2-(3-(3,5-difluorophenyl)-3-(4-methoxyphenyl)propanamido)-2-phenyl acetamido)-2,2-difluoro-5-methyl-3-oxo-N-(2,2,2-trifluoroethyl)hexanamide;
(4S)-4-((2 S)-2-(3-(3,5-difluorophenyl)-3-(4-methoxyphenyl)propanamido)-3-phenylpropanamido)-2,2-difluoro-5-methyl-3-oxo-N-(2,2,2-trifluoroethyl)hexanamide;
(S)-4-((S)-2-(4-chlorophenyl)-2-((S)-3-(3,5-dichlorophenyl)-3-phenylpropanamido)acetamido)-2,2-difluoro-5-methyl-3-oxo-N-(2,2,2-trifluoroethyl)hexanamide;
(S)-4-((S)-2-((R)-3-(3,5-dichlorophenyl)-3-phenylpropanamido)-2-phenylacetamido)-2,2-difluoro-5-methyl-3-oxo-N-(2,2,2-trifluoroethyl)hexanamide; and,
(S)-4-((S)-2-(4-chlorophenyl)-2-((R)-3-(3,5-dichlorophenyl)-3-phenylpropanamido)acetamido)-2,2-difluoro-5-methyl-3-oxo-N-(2,2,2-trifluoroethyl)hexanamide; or,
a pharmaceutically acceptable salt thereof.

21. The compound according to claim 1, which compound is selected from the group consisting of:
(4S)-4-[[(2S)-2-[[(3 S)-3-(3-chlorophenoxy)-3-phenylpropanoyl]amino]-2-(4-chlorophenyl)acetyl]amino]-2,2-difluoro-5-methyl-3-oxo-N-(2,2,2-trifluoroethyl)hexanamide;
(4S)-4-[[(2S)-2-[[(3 S)-3-(3-chlorophenoxy)-3-phenylpropanoyl]amino]-2-phenyl acetyl]amino]-2,2-difluoro-5-methyl-3-oxo-N-(2,2,2-trifluoroethyl)hexanamide;
(4S)-4-[[(2S)-2-[3-(3,4-dichlorophenyl)propanoylamino]-3-(4-methoxyphenyl)propanoyl]amino]-2,2-difluoro-5-methyl-3-oxo-N-(2,2,2-trifluoroethyl)hexanamide;
(4S)-4-[[(2S)-2-[[2-(3,5-dichlorophenoxy)acetyl]amino]-2-(4-methoxyphenyl)acetyl]amino]-2,2-difluoro-5-methyl-3-oxo-N-(2,2,2-trifluoroethyl)hexanamide;
(4S)-4-[[(2S)-2-[[3-(3-chlorophenyl)-3-phenylpropanoyl]amino]-2-phenyl acetyl]amino]-2,2-difluoro-5-methyl-3-oxo-N-(2,2,2-trifluoroethyl)hexanamide;
(4S)-4-[[(2S)-2-(4-chlorophenyl)-2-[[3-(3-chlorophenyl)-3-phenylpropanoyl]amino]acetyl]amino]-2,2-difluoro-5-methyl-3-oxo-N-(2,2,2-trifluoroethyl)hexanamide;
(4S)-4-[[(2S)-2-[[(E)-3-(4-chlorophenyl)prop-2-enoyl]amino]-2-(4-methoxyphenyl)acetyl]amino]-2,2-difluoro-5-methyl-3-oxo-N-(2,2,2-trifluoroethyl)hexanamide;
(4S)-4-[[(2S)-2-[[3-(3,4-dichlorophenyl)-3-phenylpropanoyl]amino]-2-(4-methoxyphenyl)acetyl]amino]-2,2-difluoro-5-methyl-3-oxo-N-(2,2,2-trifluoroethyl)hexanamide;
(4S)-4-[[(2S)-2-[[3-(3-chlorophenoxy)-3-(3,4-dichlorophenyl)propanoyl]amino]-2-phenyl acetyl]amino]-2,2-difluoro-5-methyl-3-oxo-N-(2,2,2-trifluoroethyl)hexanamide;

(4S)-4-[[(2S)-2-[[3-(3-chlorophenoxy)-3-(3,4-dichlorophenyl)propanoyl]amino]-2-(4-chlorophenyl)acetyl]amino]-2,2-difluoro-5-methyl-3-oxo-N-(2,2,2-trifluoroethyl)hexanamide;

(4S)-4-[[(2S)-2-[[(3R)-3-(3-chlorophenoxy)-3-phenylpropanoyl]amino]-2-phenyl acetyl]amino]-2,2-difluoro-5-methyl-3-oxo-N-(2,2,2-trifluoroethyl)hexanamide;

(4S)-4-[[(2S)-2-[[(3R)-3-(3-chlorophenoxy)-3-phenylpropanoyl]amino]-2-(4-chlorophenyl)acetyl]amino]-2,2-difluoro-5-methyl-3-oxo-N-(2,2,2-trifluoroethyl)hexanamide;

(4S)-4-[[(2S)-2-[[(3 S)-3-(4-chlorophenoxy)-3-(3,4-dichlorophenyl)propanoyl]amino]-2-(4-chlorophenyl)acetyl]amino]-2,2-difluoro-5-methyl-3-oxo-N-(2,2,2-trifluoroethyl)hexanamide;

(4S)-4-[[(2S)-2-[[3-(4-chlorophenoxy)-3-(3,4-dichlorophenyl)propanoyl]amino]-2-phenyl acetyl]amino]-2,2-difluoro-5-methyl-N-(2-morpholin-4-yl ethyl)-3-oxohexanamide;

(4S)-4-[[(2S)-2-[[(E)-3-(3,4-dichlorophenyl)prop-2-enoyl]amino]-2-phenylacetyl]amino]-2,2-difluoro-5-methyl-N-(2-morpholin-4-ylethyl)-3-oxohexanamide;

(4S)-4-[[(2 S)-2-[[2-(3,5-dichlorophenyl)sulfanylacetyl]amino]-3-phenylpropanoyl]amino]-2,2-difluoro-5-methyl-3-oxo-N-(2,2,2-trifluoroethyl)hexanamide;

(4S)-4-[[(2S)-2-[[3-(3-chlorophenoxy)-3-(5-chloropyridin-3-yl)propanoyl]amino]-2-phenyl acetyl]amino]-2,2-difluoro-5-methyl-3-oxo-N-(2,2,2-trifluoroethyl)hexanamide;

(4 S)-4-[[(2 S)-2-[[3-(3-chlorophenyl)-3-pyridin-3-yl)oxypropanoyl]amino]-2-phenylacetyl]amino]-2,2-difluoro-5-methyl-3-oxo-N-(2,2,2-trifluoroethyl)hexanamide; and, (4S)-4-[[(2S)-2-[[3-(3-chlorophenyl)-3-(5-chloropyridin-3-yl)oxypropanoyl]amino]-2-(4-methoxyphenyl)acetyl]amino]-2,2-difluoro-5-methyl-3-oxo-N-(2,2,2-trifluoroethyl)hexanamide; or, a pharmaceutically acceptable salt thereof.

22. The compound according to claim 1, which compound is selected from the group consisting of:

(4S)-4-[[(2S)-2-[[2-(3,5-dichlorophenoxy)acetyl]amino]-3-phenylpropanoyl]amino]-2,2-difluoro-5-methyl-3-oxo-N-(2,2,2-trifluoroethyl)hexanamide;

(4S)-4-[[(2S)-3-(4-chlorophenyl)-2-[[2-(3,5-dichlorophenoxy)acetyl]amino]propanoyl]amino]-2,2-difluoro-5-methyl-3-oxo-N-(2,2,2-trifluoroethyl)hexanamide;

(4S)-4-[[(2S)-2-(4-chlorophenyl)-2-[[2-(3,5-dichlorophenoxy)acetyl]amino]acetyl]amino]-2,2-difluoro-5-methyl-3-oxo-N-(2,2,2-trifluoroethyl)hexanamide;

(4S)-4-[[(2S)-2-[[2-(3,5-dichlorophenoxy)acetyl]amino]-2-phenylacetyl]amino]-2,2-difluoro-5-methyl-3-oxo-N-(2,2,2-trifluoroethyl)hexanamide;

(4S)-4-[[(2S)-2-[[3-(3,4-dichlorophenyl)-3-phenoxypropanoyl]amino]-3-phenylpropanoyl]amino]-2,2-difluoro-5-methyl-3-oxo-N-(2,2,2-trifluoroethyl)hexanamide;

(4S)-4-[[(2S)-2-[[3-(4-chlorophenoxy)-3-(3,4-dichlorophenyl)propanoyl]amino]-3-phenylpropanoyl]amino]-2,2-difluoro-5-methyl-3-oxo-N-(2,2,2-trifluoroethyl)hexanamide; and, (4S)-4-[[(2S)-2-[[3-(4-chlorophenoxy)-3-(3,4-dichlorophenyl)propanoyl]amino]-2-phenylacetyl]amino]-2,2-difluoro-5-methyl-3-oxo-N-(2,2,2-trifluoroethyl)hexanamide; or, a pharmaceutically acceptable salt thereof.

23. A process to prepare a compound according to claim 1 said process comprising the steps of:

a) reacting a compound of formula (III) with a compound of formula (IV)

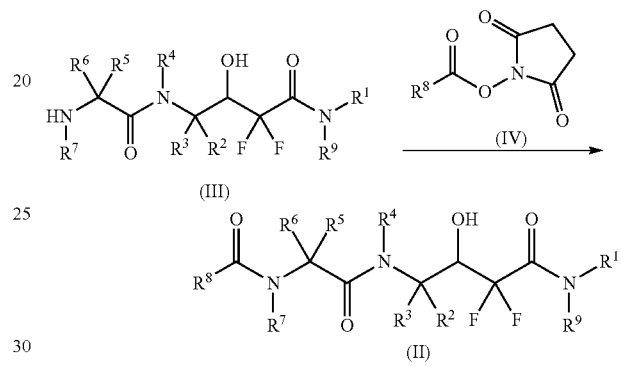

to afford a compound of formula (II) and then, b) oxidizing the compound of formula (II) to afford a compound of formula (I)

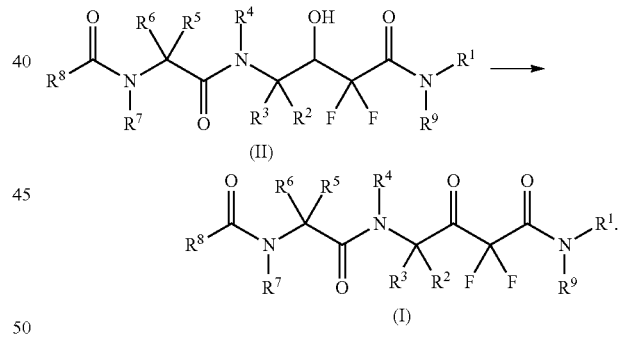

24. A pharmaceutical composition comprising a compound according to claim 1 and at least one pharmaceutically acceptable excipient, carrier of diluent.

* * * * *